United States Patent
Corral et al.

(10) Patent No.: US 10,907,174 B2
(45) Date of Patent: *Feb. 2, 2021

(54) MEANS AND METHODS TO INDUCE APOMIXIS IN PLANTS

(71) Applicant: Leibniz-Institut für Pflanzengenetik und Kulturpflanzenforschung Gatersleben (IPK), Gatersleben (DE)

(72) Inventors: José M. Corral, Quedlinburg (DE); Timothy Sharbel, Saskatoon (CA)

(73) Assignee: LEIBNIZ-INSTITUT FÜR PFLANZENGENETIK UND KULTURPFLANZENFORSCHUNG GATERSLEBEN (IPK), Gatersleben (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,957

(22) Filed: Oct. 3, 2018

(65) Prior Publication Data
US 2019/0211353 A1    Jul. 11, 2019

Related U.S. Application Data

(63) Continuation of application No. 14/123,069, filed as application No. PCT/EP2012/059808 on May 25, 2012, now Pat. No. 10,131,919.

(30) Foreign Application Priority Data

May 30, 2011 (EP) ..................... 1168075

(51) Int. Cl.
*C12N 15/82* (2006.01)

(52) U.S. Cl.
CPC ..... *C12N 15/8287* (2013.01); *C12N 15/8233* (2013.01)

(58) Field of Classification Search
None
See application file for complete search history.

(56) References Cited

U.S. PATENT DOCUMENTS

| | | | |
|---|---|---|---|
| 7,541,514 B2 | 6/2009 | Carman | |
| 10,131,919 B2* | 11/2018 | Corral | C12N 9/22 |
| 2002/0069433 A1 | 6/2002 | Schmidt et al. | |
| 2008/0155712 A1 | 6/2008 | Savidan et al. | |
| 2009/0094717 A1* | 4/2009 | Troukhan | C07K 14/415 800/290 |
| 2010/0257621 A1 | 10/2010 | Ketkar et al. | |
| 2012/0144529 A1* | 6/2012 | Sanz Molinero | C07K 14/415 800/287 |
| 2015/0299727 A1 | 10/2015 | Sharbel et al. | |

FOREIGN PATENT DOCUMENTS

| CN | 1248296 A | 3/2000 |
|---|---|---|
| CN | 1391435 A | 1/2003 |
| WO | 9836090 A1 | 8/1998 |
| WO | 9935258 A1 | 7/1999 |
| WO | 0132001 A1 | 5/2001 |
| WO | 2011/020746 A1 | 2/2011 |
| WO | 2011/055352 A1 | 5/2011 |
| WO | 2012/163818 A1 | 12/2012 |
| WO | 2015/061355 A1 | 4/2015 |

OTHER PUBLICATIONS

Accession No. CAN66660 dated Feb. 5, 2008.
Accession No. NP_177579 dated Jan. 22, 2014.
Accession No. XP_002514727 dated Feb. 25, 2016.
Accession No. XP_002888974 dated Jun. 11, 2010.
Accession No. XP_003524710 dated Nov. 25, 2015.
Corral et al., "A Conserved Apomixis-Specific Polymorphism Is Correlated with Exclusive Exonuclease Expression in Premeiotic Ovules of Apomictic *Boechera* Species", Plant Physiology, Dec. 2013, pp. 1660-1672, vol. 163; Published online Oct. 25, 2013. doi: 10.1104/pp.113222430 <https://dx.doi.org/10.1104%2Fpp.113.222430>.
Culligan et al., "ATR and ATM Play Both Distinct and Additive Roles in Response to Ionizing Radiation", The Plant Journal, 2006, pp. 947-961, vol. 48, Blackwell Publishing Ltd.
Data Appendix submitted in EP Application EP12725353.2 on Oct. 19, 2015.
Grossniklaus, "From Sexuality to Apomixis: Molecular and Genetic Approaches", The Flowering of Apomixis: From Mechanisms to Genetic Engineering, 2001, pp. 168-211, Chapter 12.
Haiying et al., "Protemic Analysis of Sugar Beet Apomictic Monosomic Addition Line M14", Journal of Proteomics, Dec. 1, 2009, pp. 297-308, vol. 73, No. 2.
Hand et al., "The Genetic Control of Apomixis: Asexual Seed Formation", Genetics, Jun. 1, 2014, pp. 441-450, vol. 197, Issue 2.
Hsiao et al., "Flow an Exonuclease Decides Where to Stop in Trimming of Nucleic Acids: Crystal Structures of RNase T-Product Complexes", Nucleic Acids Research, 2012, pp. 8144-8154, Vlk, 40, No. 16.
International Preliminary Report on Patentability for PCT/EP2012/059808 dated Dec. 12, 2013.
International Search Report and Written Opinion of the ISA for PCT/EP2012/059808, ISA/EP, Rijswijk, NL, dated Sep. 25, 2012.
Kawaoka et al., "Functional Analysis of Tobacco LIM Protein Ntliml Involved in Lignin Biosynthesis", The Plant Journal, May 1, 2000, pp. 289-301, vol. 22, No. 4.

(Continued)

*Primary Examiner* — Ashley K Buran
(74) *Attorney, Agent, or Firm* — Thompson Cobum LLP

(57) ABSTRACT

The present invention relates to nucleic acid molecules for use in inducing apomixis in a plant, transgenic cells, in particular transgenic plant cells, comprising said nucleic acid molecule, transgenic plants, in particular plant seeds, comprising said nucleic acid molecule, methods for inducing apomixis in a plant, methods for the production of apomictic plants and uses thereof.

20 Claims, No Drawings

Specification includes a Sequence Listing.

(56) References Cited

OTHER PUBLICATIONS

Laubinger et al., "Global Effects of the Small RNA Biogenesis Machinery on the *Arabidopsis thaliana* Transcriptome", Proceedings of the National Academy of Science, Oct. 12, 2010, pp. 17466-17473, vol. 107, No. 41.
Le et al., "Global analysis of gene activity during *Arabidopsis* seed development and identification of seed-specific transcription factors", PNAS, May 4, 2010, pp. 8063-8070, vol. 107, No. 18.
Lipman et al., "Rapid and Sensitive Protein Similarity Searches", Science, Mar. 1985, pp. 1435-1441, vol. 227.
Martinelli et al., "Gene regulation in parthenocarpic tomato fruit", Journal of Experimental Botany, 2009, pp. 3873-3890, vol. 60 No. 13.
Martinez, "An Efficient Method for Finding Repeats in Molecular Sequences", Nucleic Acids Research, 1983, pp. 4629-4634, vol. 11, No. 13.
Mau et al., "The Conserved Chimeric Transcript UPGRADE2 is Associated with Unreduced Pollen Formation and Is Exclusively Found in Apomictic *Boechera* Species", Plant Physiology, Dec. 2013, pp. 1640-1659, vol. 163.
Moser et al., "The Proofreading Domain of *Escherichia coli* DNA Polymerase I and Other DNA and/or RNA Exonuclease Domains", Nucleic Acids Research, 1997, pp. 5110-5118, vol. 25, No. 24.
Nain et al., "Cloning of an ovule specific promoter from *Arabidopsis thaliana* and expression of beta-glucuronidase", Indian Journal of Experimental Biology, Apr. 2008, pp. 207-11, vol. 46 No. 4, abstract only.
Needleman et al., "A General Method Applicable to the Search for Similarities in the Amino Acid Sequence of Two Proteins", Journal of Molecular Biology, 1970, pp. 443-453, vol. 48.
Nguyen et al., "*Arabidopsis thaliana* Putative Exonuclease (At1g74390) mRNA", XP002658227, Oct. 24, 2002, retrieved from EBI Database Accession No. BT000288, whole document, Elsevier Science Publishers, Amsterbam, NL.
NSF-Funded Seed Project of Goldberg & Harada Laboratories, retrieved from http://seedgenenetwork.net/project on Jun. 14, 2016.
Peiffer et al., "A Spatial Dissection of the *Arabidopsis* Floral Transcriptome by MPSS", BMC Plant Biology, Apr. 21, 2008, pp. 1-16, vol. 8, No. 43.
Peiffer, "A Spatial Dissection of the *Arabidopsis* Floral Transcriptome by MPSS", Thesis, 2007, 79 pages, University of Delaware.
Pellino et al., "Selection of Reference Genes for Quantitative Real-time PCR Expression Studies of Microdissected Reproductive Tissues in Apomictic and Sexual Boechera", BMC Research Notes, Aug. 19, 2011, p. 303, vol. 4, No. 1.

Perez-Espana et al., "CYP85A1 is required for the initiation of femal gametogenesis in *Arabidopsis thaliana*", Plant Signaling and Behavior, Mar. 2001, pp. 321-326, vol. 6 No. 3.
Rodrigues et al., "Identification of Differentially Expressed cDNA Sequences in Ovaries of Sexual and Apomictic Plants of Brachiaria Brizanthan", Plant Molecular Biology, Dec. 1, 2003, pp. 745-757, vol. 53, No. 6.
Rose et al., "Consensus-degenerate Hybrid Oligonucleotide Primers for Amplification of Distantly Related Sequences", Nucleic Acid Research, 1998, pp. 1628-1635, vol. 26 No. 7.
Schallau et al., "Identification and Genetic Analysis of the Aposory Locus in *Hypericum perforatum* L.", The Plant Journal, Jun. 26, 2010, pp. 773-784, vol. 62, No. 5.
Schranz et al., "Asexual Reproduction in a Close Relative of *Arabidopsis*: A Genetic Investigation of Apomixis in Boechera", New Phytologist, 2006, pp. 425-438, vol. 171.
Sharbel et al., "Apomictic and Sexual Ovules of Boechera Display Heterochronic Global Gene Expression Patterns", The Plant Cell, Mar. 2010, pp. 655-671, vol. 22.
Sharbel et al., "Molecular Signatures of Apomictic and Sexual Ovules in the Boechera Holboellii Complex", The Plant Journal, 2009, pp. 870-882, vol. 58.
Spillane, et al., "Apomixis Technology Development-Virgin Births in Farmers' Fields?", Nature Biotechnology, Jun. 2004, pp. 687-691, vol. 22, No. 6.
Theologis et al., "Sequence and Analysis of Chromosome 1 of the Plant *Arabidopsis thaliana*", Nature, Dec. 14, 2000, pp. 816-820, vol. 408.
Wilbur et al., "Rapid Similarity Searches of Nucleic Acid and Protein Data Banks", Proceedings of the National Academy of Sciences USA, Feb. 1983, pp. 726-730, vol. 80.
Windsor et al., "Partial Shotgun Sequencing of the Boechera stricta Genome Reveals Extensive Microsynteny and Promoter Conservation with *Arabidopsis*", Plant Physiology, Apr. 2006, pp. 1169-1182, vol. 140.
Zou et al., "Exoribonuclease Superfamilies: Structural Analysis and Phylogenetic Distribution", Nucleic Acid Research, 2001, pp. 1017-1026, vol. 29 No. 5.
Hill et al., "Functional Analysis of Conserved Histidines in ADP-Glucose Pyrophosphorylase from *Escherichia coli*", Biochemical and Biophysical Research Communications, Mar. 17, 1998, pp. 573-577, vol. 244, Issue 2.
Lazar et al., "Transforming Growth Factor a: Mutation of Aspartic Acid 47 and Leucine 48 Results in Different Biological Activities", Molecular and Cellular Biology, Mar. 1988, pp. 1247-1252, vol. 8, No. 3.
Canadian examination report for Canadian application No. 2,837,785 dated Mar. 11, 2019.

* cited by examiner

SEQUENCE LISTING

```
<160> NUMBER OF SEQ ID NOS: 65

<210> SEQ ID NO 1
<211> LENGTH: 165
<212> TYPE: PRT
<213> ORGANISM: Boechera
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid
```

```
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (123)..(124)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid

<400> SEQUENCE: 1

Val Phe Phe Asp Leu Glu Thr Ala Val Xaa Thr Xaa Ser Gly Gln Pro
1               5                   10                  15

Xaa Ala Ile Leu Glu Phe Gly Ala Ile Leu Val Cys Pro Met Lys Leu
            20                  25                  30

Xaa Glu Leu Tyr Ser Tyr Xaa Thr Leu Xaa Arg Pro Thr Asp Leu Ser
        35                  40                  45

Leu Ile Xaa Thr Leu Thr Lys Arg Arg Ser Gly Ile Thr Arg Asp Gly
    50                  55                  60

Val Leu Ser Ala Pro Thr Phe Ser Glu Ile Ala Asp Glu Xaa Tyr Asp
65                  70                  75                  80

Ile Xaa Xaa Gly Arg Ile Trp Xaa Gly His Asn Ile Lys Arg Phe Asp
                85                  90                  95

Cys Val Arg Xaa Xaa Asp Ala Phe Ala Xaa Ile Gly Xaa Xaa Pro Xaa
                100                 105                 110

Glu Xaa Lys Xaa Xaa Ile Asp Xaa Leu Ser Xaa Xaa Ser Gln Lys Phe
            115                 120                 125

Gly Lys Xaa Ala Gly Asp Xaa Lys Met Ala Xaa Xaa Ala Thr Tyr Phe
        130                 135                 140

Xaa Leu Gly Asp Gln Ala His Arg Ser Leu Asp Asp Val Arg Met Asn
```

```
                 145                 150                 155                 160

Leu Glu Val Xaa Lys
                165

<210> SEQ ID NO 2
<211> LENGTH: 165
<212> TYPE: PRT
<213> ORGANISM: Boechera
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid

<400> SEQUENCE: 2

Val Phe Phe Asp Leu Glu Thr Ala Val Pro Thr Lys Ser Gly Gln Pro
1               5                   10                  15

Xaa Ala Ile Leu Glu Phe Gly Ala Ile Leu Val Cys Pro Met Lys Leu
            20                  25                  30

Val Glu Leu Tyr Ser Tyr Ser Thr Leu Val Arg Pro Thr Asp Leu Ser
        35                  40                  45

Leu Ile Ser Thr Leu Thr Lys Arg Arg Ser Gly Ile Thr Arg Asp Gly
    50                  55                  60

Val Leu Ser Ala Pro Thr Phe Ser Glu Ile Ala Asp Glu Val Tyr Asp
65                  70                  75                  80

Ile Leu Xaa Gly Arg Ile Trp Xaa Gly His Asn Ile Lys Arg Phe Asp
                85                  90                  95

Cys Val Arg Ile Xaa Asp Ala Phe Ala Xaa Ile Gly Leu Xaa Pro Pro
            100                 105                 110

Glu Pro Lys Ala Thr Ile Asp Ser Leu Ser Leu Xaa Ser Gln Lys Phe
        115                 120                 125

Gly Lys Arg Ala Gly Asp Met Lys Met Ala Ser Xaa Ala Thr Tyr Phe
    130                 135                 140
```

```
Xaa Leu Gly Asp Gln Ala His Arg Ser Leu Asp Asp Val Arg Met Asn
145                 150                 155                 160

Leu Glu Val Xaa Lys
                165

<210> SEQ ID NO 3
<211> LENGTH: 165
<212> TYPE: PRT
<213> ORGANISM: Boechera
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (123)..(124)
<223> OTHER INFORMATION: Xaa can be any naturally occurring amino acid
<220> FEATURE:
<221> NAME/KEY: misc_feature
<222> LOCATION: (131)..(131)
```

```
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid

<400> SEQUENCE: 3

Val Phe Phe Asp Leu Glu Thr Ala Val Xaa Thr Xaa Ser Gly Gln Pro
 1               5                  10                  15

Phe Ala Ile Leu Glu Phe Gly Ala Ile Leu Val Cys Pro Met Lys Leu
             20                  25                  30

Xaa Glu Leu Tyr Ser Tyr Xaa Thr Leu Xaa Arg Pro Thr Asp Leu Ser
         35                  40                  45

Leu Ile Xaa Thr Leu Thr Lys Arg Arg Ser Gly Ile Thr Arg Asp Gly
     50                  55                  60

Val Leu Ser Ala Pro Thr Phe Ser Glu Ile Ala Asp Glu Xaa Tyr Asp
 65                  70                  75                  80

Ile Xaa His Gly Arg Ile Trp Ala Gly His Asn Ile Lys Arg Phe Asp
             85                  90                  95

Cys Val Arg Xaa Xaa Asp Ala Phe Ala Xaa Ile Gly Xaa Xaa Pro Xaa
            100                 105                 110

Glu Xaa Lys Xaa Xaa Ile Asp Xaa Leu Ser Xaa Xaa Ser Gln Lys Phe
        115                 120                 125

Gly Lys Xaa Ala Gly Asp Xaa Lys Met Ala Xaa Xaa Ala Thr Tyr Phe
    130                 135                 140

Xaa Leu Gly Asp Gln Ala His Arg Ser Leu Asp Asp Val Arg Met Asn
145                 150                 155                 160

Leu Glu Val Xaa Lys
                165

<210> SEQ ID NO 4
<211> LENGTH: 506
<212> TYPE: PRT
<213> ORGANISM: Boechera
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
```

```
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(130)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (136)..(137)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
```

-continued

```
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (195)..(197)
<223> OTHER INFORMATION: Xaa can be any naturally occurring amino acid
<220> FEATURE:
<221> NAME/KEY: misc_feature
<222> LOCATION: (200)..(202)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (258)..(259)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (303)..(303)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (330)..(331)
```

-continued

```
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (341)..(342)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (351)..(352)
<223> OTHER INFORMATION: Xaa can be any naturally occurring amino acid
<220> FEATURE:
<221> NAME/KEY: misc_feature
<222> LOCATION: (354)..(354)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (360)..(361)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (397)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (420)..(420)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
```

-continued

<222> LOCATION: (444)..(444)
<223> OTHER INFORMATION: Xaa can be any naturally occurring amino acid
<220> FEATURE:
<221> NAME/KEY: misc_feature
<222> LOCATION: (448)..(448)
<223> OTHER INFORMATION: Xaa can be any naturally occurring amino acid
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid

<400> SEQUENCE: 4

Met Ala Ser Thr Leu Gly Xaa Asp Xaa Arg Xaa Glu Ile Val Phe Phe
1 5 10 15

Asp Leu Glu Thr Ala Val Xaa Thr Xaa Ser Gly Gln Pro Xaa Ala Ile
20 25 30

Leu Glu Phe Gly Ala Ile Leu Val Cys Pro Met Lys Leu Xaa Glu Leu
35 40 45

Tyr Ser Tyr Xaa Thr Leu Xaa Arg Pro Thr Asp Leu Ser Leu Ile Xaa
50 55 60

Thr Leu Thr Lys Arg Arg Ser Gly Ile Thr Arg Asp Gly Val Leu Ser
65 70 75 80

Ala Pro Thr Phe Ser Glu Ile Ala Asp Glu Xaa Tyr Asp Ile Xaa Xaa
85 90 95

Gly Arg Ile Trp Xaa Gly His Asn Ile Lys Arg Phe Asp Cys Val Arg
100 105 110

Xaa Xaa Asp Ala Phe Ala Xaa Ile Gly Xaa Xaa Pro Xaa Glu Xaa Lys
115 120 125

Xaa Xaa Ile Asp Xaa Leu Ser Xaa Xaa Ser Gln Lys Phe Gly Lys Xaa
130 135 140

Ala Gly Asp Xaa Lys Met Ala Xaa Xaa Ala Thr Tyr Phe Xaa Leu Gly
145 150 155 160

Asp Gln Ala His Arg Ser Leu Asp Asp Val Arg Met Asn Leu Glu Val
165 170 175

Xaa Lys Xaa Cys Xaa Thr Xaa Leu Phe Leu Glu Ser Ser Val Pro Asp
180 185 190

Ile Leu Xaa Xaa Xaa Ser Trp Xaa Xaa Xaa Arg Lys Ser Xaa Xaa Thr
195 200 205

Arg Ser Asn Glu Lys Ser Leu Pro Xaa Gly Val Arg Glu Ser Pro Thr
210                 215                 220

Ser Ser Ser Xaa Ser Pro Xaa Xaa Asp Pro Ser Ser Ser Val Xaa
225                 230                 235                 240

Ala Thr Xaa Val Lys Asn His Pro Ile Ile Ser Leu Leu Thr Glu Cys
                245                 250                 255

Ser Xaa Xaa Asp Thr Ser Ser Xaa Glu Ile Asp Pro Ser Asp Ile Thr
            260                 265                 270

Thr Leu Ile Ser Lys Leu His Ile Gly Thr Leu Lys Xaa Asp Ala Ala
                275                 280                 285

Asp Glu Ala Lys Thr Val Arg Asp Ala Ala Xaa Glu Ala Lys Xaa Val
290                 295                 300

Arg Gln Gln Gly Glu Ser Thr Asp Pro Asn Ala Lys Asp Glu Ser Phe
305                 310                 315                 320

Xaa Gly Val Asn Glu Val Ser Xaa Ser Xaa Xaa Arg Ala Ser Leu Xaa
                325                 330                 335

Pro Leu Tyr Arg Xaa Xaa Leu Arg Met Glu Leu Xaa His Asn Xaa Xaa
                340                 345                 350

Pro Xaa His Leu Xaa Trp Tyr Xaa Xaa Lys Ile Arg Phe Gly Ile Ser
        355                 360                 365

Arg Lys Xaa Val Asp His Val Gly Arg Pro Lys Met Asn Ile Val Val
370                 375                 380

Asp Ile Xaa Pro Asp Leu Cys Lys Ile Leu Asp Ala Xaa Xaa Ala Xaa
385                 390                 395                 400

Ala His Asn Leu Leu Ile Asp Ser Ser Thr Xaa Ser Xaa Xaa Arg Pro
                405                 410                 415

Thr Val Met Xaa Lys Xaa Gly Phe Xaa Asn Tyr Pro Thr Ala Xaa Leu
                420                 425                 430

Gln Ile Ser Ser Glu Ser Asn Xaa Thr Xaa Val Xaa Gln Lys Glu Xaa
                435                 440                 445

Pro Leu Gly Thr Asn Gln Lys Leu Asp Phe Ser Ser Asp Asn Phe Glu
450                 455                 460

Lys Leu Glu Ser Ala Leu Xaa Pro Gly Xaa Leu Val Asp Xaa Phe Phe
465                 470                 475                 480

Ser Xaa Glu Xaa Tyr Asp Tyr Xaa Lys Met Val Gly Ile Xaa Leu Ala
            485                 490                 495

Ala Arg Lys Leu Val Ile Xaa Leu Lys Lys
            500                 505

<210> SEQ ID NO 5
<211> LENGTH: 506
<212> TYPE: PRT
<213> ORGANISM: Boechera
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

```
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (195)..(197)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (303)..(303)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid
<220> FEATURE:
<221> NAME/KEY: misc_feature
<222> LOCATION: (341)..(342)
```

```
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (352)..(352)
<223> OTHER INFORMATION: Xaa can be any naturally occurring amino acid
<220> FEATURE:
<221> NAME/KEY: misc_feature
<222> LOCATION: (354)..(354)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (414)..(414)
<223> OTHER INFORMATION: Xaa can be any naturally occurring amino acid
<220> FEATURE:
<221> NAME/KEY: misc_feature
<222> LOCATION: (420)..(420)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid

<400> SEQUENCE: 5

Met Ala Ser Thr Leu Gly Gly Asp Xaa Arg Asn Glu Ile Val Phe Phe
1               5                   10                  15

Asp Leu Glu Thr Ala Val Pro Thr Lys Ser Gly Gln Pro Xaa Ala Ile
            20                  25                  30

Leu Glu Phe Gly Ala Ile Leu Val Cys Pro Met Lys Leu Val Glu Leu
        35                  40                  45

Tyr Ser Tyr Ser Thr Leu Val Arg Pro Thr Asp Leu Ser Leu Ile Ser
    50                  55                  60

Thr Leu Thr Lys Arg Arg Ser Gly Ile Thr Arg Asp Gly Val Leu Ser
65                  70                  75                  80
```

```
Ala Pro Thr Phe Ser Glu Ile Ala Asp Glu Val Tyr Asp Ile Leu Xaa
                85                  90                  95

Gly Arg Ile Trp Xaa Gly His Asn Ile Lys Arg Phe Asp Cys Val Arg
            100                 105                 110

Ile Xaa Asp Ala Phe Ala Xaa Ile Gly Leu Xaa Pro Pro Glu Pro Lys
        115                 120                 125

Ala Thr Ile Asp Ser Leu Ser Leu Xaa Ser Gln Lys Phe Gly Lys Arg
    130                 135                 140

Ala Gly Asp Met Lys Met Ala Ser Xaa Ala Thr Tyr Phe Xaa Leu Gly
145                 150                 155                 160

Asp Gln Ala His Arg Ser Leu Asp Asp Val Arg Met Asn Leu Glu Val
            165                 170                 175

Xaa Lys Xaa Cys Ser Thr Val Leu Phe Leu Glu Ser Val Pro Asp
        180                 185                 190

Ile Leu Xaa Xaa Xaa Ser Trp Xaa Xaa Pro Arg Lys Ser Pro Xaa Thr
        195                 200                 205

Arg Ser Asn Glu Lys Ser Leu Pro Xaa Gly Val Arg Glu Ser Pro Thr
    210                 215                 220

Ser Ser Ser Xaa Ser Pro Xaa Thr Asp Pro Ser Ser Ser Val Asp
225                 230                 235                 240

Ala Thr Xaa Val Lys Asn His Pro Ile Ile Ser Leu Leu Thr Glu Cys
            245                 250                 255

Ser Xaa Ser Asp Thr Ser Ser Cys Glu Ile Asp Pro Ser Asp Ile Thr
        260                 265                 270

Thr Leu Ile Ser Lys Leu His Ile Gly Thr Leu Lys Xaa Asp Ala Ala
        275                 280                 285

Asp Glu Ala Lys Thr Val Arg Asp Ala Ala Asp Glu Ala Lys Xaa Val
    290                 295                 300

Arg Gln Gln Gly Glu Ser Thr Asp Pro Asn Ala Lys Asp Glu Ser Phe
305                 310                 315                 320

Leu Gly Val Asn Glu Val Ser Val Ser Xaa Ile Arg Ala Ser Leu Ile
            325                 330                 335

Pro Leu Tyr Arg Xaa Xaa Leu Arg Met Glu Leu Xaa His Asn Asp Xaa
            340                 345                 350

Pro Xaa His Leu Cys Trp Tyr Ser Leu Lys Ile Arg Phe Gly Ile Ser
        355                 360                 365

Arg Lys Tyr Val Asp His Val Gly Arg Pro Lys Met Asn Ile Val Val
    370                 375                 380

Asp Ile Xaa Pro Asp Leu Cys Lys Ile Leu Asp Ala Xaa Asp Ala Ala
385                 390                 395                 400

Ala His Asn Leu Leu Ile Asp Ser Ser Thr Xaa Ser Asp Xaa Arg Pro
            405                 410                 415

Thr Val Met Xaa Lys Xaa Gly Phe Xaa Asn Tyr Pro Thr Ala Arg Leu
            420                 425                 430

Gln Ile Ser Ser Glu Ser Asn Gly Thr Gln Val Xaa Gln Lys Glu Glu
    435                 440                 445

Pro Leu Gly Thr Asn Gln Lys Leu Asp Phe Ser Ser Asp Asn Phe Glu
450                 455                 460

Lys Leu Glu Ser Ala Leu Leu Pro Gly Thr Leu Val Asp Xaa Phe Phe
465                 470                 475                 480

Ser Xaa Glu Xaa Tyr Asp Tyr Lys Lys Met Val Gly Ile Xaa Leu Ala
            485                 490                 495

Ala Arg Lys Leu Val Ile Gln Leu Lys Lys
```

```
                500             505

<210> SEQ ID NO 6
<211> LENGTH: 506
<212> TYPE: PRT
<213> ORGANISM: Boechera
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(130)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
```

```
<220> FEATURE:
<221> NAME/KEY: misc_feature
<222> LOCATION: (136)..(137)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (200)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (303)..(303)
```

```
-continued

<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (341)..(342)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (360)..(361)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (397)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(414)
<223> OTHER INFORMATION: Xaa can be any naturally occurring amino acid
<220> FEATURE:
<221> NAME/KEY: misc_feature
<222> LOCATION: (420)..(420)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
```

```
<222> LOCATION: (444)..(444)
<223> OTHER INFORMATION: Xaa can be any naturally occurring amino acid
<220> FEATURE:
<221> NAME/KEY: misc_feature
<222> LOCATION: (448)..(448)
<223> OTHER INFORMATION: Xaa can be any naturally occurring amino acid
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid

<400> SEQUENCE: 6

Met Ala Ser Thr Leu Gly Xaa Asp Xaa Arg Xaa Glu Ile Val Phe Phe
1               5                   10                  15

Asp Leu Glu Thr Ala Val Xaa Thr Xaa Ser Gly Gln Pro Phe Ala Ile
            20                  25                  30

Leu Glu Phe Gly Ala Ile Leu Val Cys Pro Met Lys Leu Xaa Glu Leu
        35                  40                  45

Tyr Ser Tyr Xaa Thr Leu Xaa Arg Pro Thr Asp Leu Ser Leu Ile Xaa
    50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Xaa Tyr Asp Ile Xaa His
                85                  90                  95

Gly Arg Ile Trp Ala Gly His Asn Ile Lys Arg Phe Asp Cys Val Arg
            100                 105                 110

Xaa Xaa Asp Ala Phe Ala Xaa Ile Gly Xaa Xaa Pro Xaa Glu Xaa Lys
        115                 120                 125

Xaa Xaa Ile Asp Xaa Leu Ser Xaa Xaa Ser Gln Lys Phe Gly Lys Xaa
    130                 135                 140

Ala Gly Asp Xaa Lys Met Ala Xaa Xaa Ala Thr Tyr Phe Xaa Leu Gly
145                 150                 155                 160

Asp Gln Ala His Arg Ser Leu Asp Asp Val Arg Met Asn Leu Glu Val
                165                 170                 175

Xaa Lys Xaa Cys Xaa Thr Xaa Leu Phe Leu Glu Ser Ser Val Pro Asp
            180                 185                 190

Ile Leu Xaa Xaa Met Ser Trp Xaa Xaa Xaa Arg Lys Ser Xaa Arg Thr
        195                 200                 205

Arg Ser Asn Glu Lys Ser Leu Pro Asn Gly Val Arg Glu Ser Pro Thr
    210                 215                 220
```

```
Ser Ser Ser Ser Ser Pro Lys Xaa Asp Pro Ser Ser Ser Val Xaa
225                 230                 235                 240

Ala Thr Xaa Val Lys Asn His Pro Ile Ile Ser Leu Leu Thr Glu Cys
                245                 250                 255

Ser Glu Xaa Asp Thr Ser Ser Xaa Glu Ile Asp Pro Ser Asp Ile Thr
                260                 265                 270

Thr Leu Ile Ser Lys Leu His Ile Gly Thr Leu Lys Xaa Asp Ala Ala
            275                 280                 285

Asp Glu Ala Lys Thr Val Arg Asp Ala Ala Xaa Glu Ala Lys Xaa Val
            290                 295                 300

Arg Gln Gln Gly Glu Ser Thr Asp Pro Asn Ala Lys Asp Glu Ser Phe
305                 310                 315                 320

Xaa Gly Val Asn Glu Val Ser Xaa Ser Ser Xaa Arg Ala Ser Leu Xaa
                325                 330                 335

Pro Leu Tyr Arg Xaa Xaa Leu Arg Met Glu Leu Xaa His Asn Xaa Thr
                340                 345                 350

Pro Leu His Leu Xaa Trp Tyr Xaa Xaa Lys Ile Arg Phe Gly Ile Ser
            355                 360                 365

Arg Lys Xaa Val Asp His Val Gly Arg Pro Lys Met Asn Ile Val Val
370                 375                 380

Asp Ile Pro Pro Asp Leu Cys Lys Ile Leu Asp Ala Xaa Xaa Ala Xaa
385                 390                 395                 400

Ala His Asn Leu Leu Ile Asp Ser Ser Thr Xaa Ser Xaa Xaa Arg Pro
                405                 410                 415

Thr Val Met Xaa Lys Xaa Gly Phe Ala Asn Tyr Pro Thr Ala Xaa Leu
            420                 425                 430

Gln Ile Ser Ser Glu Ser Asn Xaa Thr Xaa Val Xaa Gln Lys Glu Xaa
                435                 440                 445

Pro Leu Gly Thr Asn Gln Lys Leu Asp Phe Ser Ser Asp Asn Phe Glu
450                 455                 460

Lys Leu Glu Ser Ala Leu Xaa Pro Gly Xaa Leu Val Asp Xaa Phe Phe
465                 470                 475                 480

Ser Xaa Glu Xaa Tyr Asp Tyr Xaa Lys Met Val Gly Ile Arg Leu Ala
                485                 490                 495

Ala Arg Lys Leu Val Ile Xaa Leu Lys Lys
                500                 505
```

```
<210> SEQ ID NO 7
<211> LENGTH: 496
<212> TYPE: PRT
<213> ORGANISM: Boechera
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
```

```
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(130)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (136)..(137)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (158)..(158)
```

-continued

```
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (195)..(197)
<223> OTHER INFORMATION: Xaa can be any naturally occurring amino acid
<220> FEATURE:
<221> NAME/KEY: misc_feature
<222> LOCATION: (200)..(202)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (258)..(259)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
```

```
<222> LOCATION: (320)..(321)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (341)..(342)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (387)..(388)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (403)..(404)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
```

```
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid

<400> SEQUENCE: 7

Met Ala Ser Thr Leu Gly Xaa Asp Xaa Arg Xaa Glu Ile Val Phe
1               5                   10                  15

Asp Leu Glu Thr Ala Val Xaa Thr Xaa Ser Gly Gln Pro Xaa Ala Ile
            20                  25                  30

Leu Glu Phe Gly Ala Ile Leu Val Cys Pro Met Lys Leu Xaa Glu Leu
        35                  40                  45

Tyr Ser Tyr Xaa Thr Leu Xaa Arg Pro Thr Asp Leu Ser Leu Ile Xaa
    50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Xaa Tyr Asp Ile Xaa Xaa
                85                  90                  95

Gly Arg Ile Trp Xaa Gly His Asn Ile Lys Arg Phe Asp Cys Val Arg
            100                 105                 110

Xaa Xaa Asp Ala Phe Ala Xaa Ile Gly Xaa Xaa Pro Xaa Glu Xaa Lys
        115                 120                 125

Xaa Xaa Ile Asp Xaa Leu Ser Xaa Xaa Ser Gln Lys Phe Gly Lys Xaa
    130                 135                 140

Ala Gly Asp Xaa Lys Met Ala Xaa Xaa Ala Thr Tyr Phe Xaa Leu Gly
145                 150                 155                 160

Asp Gln Ala His Arg Ser Leu Asp Asp Val Arg Met Asn Leu Glu Val
                165                 170                 175

Xaa Lys Xaa Cys Xaa Thr Xaa Leu Phe Leu Glu Ser Ser Val Pro Asp
            180                 185                 190

Ile Leu Xaa Xaa Xaa Ser Trp Xaa Xaa Xaa Arg Lys Ser Xaa Xaa Thr
```

```
            195                 200                 205
Arg Ser Asn Glu Lys Ser Leu Pro Xaa Gly Val Arg Glu Ser Pro Thr
210                 215                 220

Ser Ser Ser Xaa Ser Pro Xaa Xaa Asp Pro Ser Ser Ser Ser Val Xaa
225                 230                 235                 240

Ala Thr Xaa Val Lys Asn His Pro Ile Ile Ser Leu Leu Thr Glu Cys
                245                 250                 255

Ser Xaa Xaa Asp Thr Ser Ser Xaa Glu Ile Asp Pro Ser Asp Ile Thr
            260                 265                 270

Thr Leu Ile Ser Lys Leu His Ile Gly Thr Leu Lys Xaa Asp Ala Ala
        275                 280                 285

Xaa Glu Ala Lys Xaa Val Arg Gln Gln Gly Glu Ser Thr Asp Pro Asn
290                 295                 300

Ala Lys Asp Glu Ser Phe Xaa Gly Val Asn Glu Val Ser Xaa Ser Xaa
305                 310                 315                 320

Xaa Arg Ala Ser Leu Xaa Pro Leu Tyr Arg Xaa Xaa Leu Arg Met Glu
                325                 330                 335

Leu Xaa His Asn Xaa Xaa Pro Xaa His Leu Xaa Trp Tyr Xaa Xaa Lys
            340                 345                 350

Ile Arg Phe Gly Ile Ser Arg Lys Xaa Val Asp His Val Gly Arg Pro
        355                 360                 365

Lys Met Asn Ile Val Val Asp Ile Xaa Pro Asp Leu Cys Lys Ile Leu
370                 375                 380

Asp Ala Xaa Xaa Ala Xaa Ala His Asn Leu Leu Ile Asp Ser Ser Thr
385                 390                 395                 400

Xaa Ser Xaa Xaa Arg Pro Thr Val Met Xaa Lys Xaa Gly Phe Xaa Asn
                405                 410                 415

Tyr Pro Thr Ala Xaa Leu Gln Ile Ser Ser Glu Ser Asn Xaa Thr Xaa
            420                 425                 430

Val Xaa Gln Lys Glu Xaa Pro Leu Gly Thr Asn Gln Lys Leu Asp Phe
        435                 440                 445

Ser Ser Asp Asn Phe Glu Lys Leu Glu Ser Ala Leu Xaa Pro Gly Xaa
450                 455                 460

Leu Val Asp Xaa Phe Phe Ser Xaa Glu Xaa Tyr Asp Tyr Xaa Lys Met
465                 470                 475                 480

Val Gly Ile Xaa Leu Ala Ala Arg Lys Leu Val Ile Xaa Leu Lys Lys
                485                 490                 495

<210> SEQ ID NO 8
<211> LENGTH: 496
<212> TYPE: PRT
<213> ORGANISM: Boechera
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
```

```
<222> LOCATION: (114)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (195)..(197)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
```

<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid

<400> SEQUENCE: 8

```
Met Ala Ser Thr Leu Gly Gly Asp Xaa Arg Asn Glu Ile Val Phe Phe
1               5                   10                  15

Asp Leu Glu Thr Ala Val Pro Thr Lys Ser Gly Gln Pro Xaa Ala Ile
            20                  25                  30

Leu Glu Phe Gly Ala Ile Leu Val Cys Pro Met Lys Leu Val Glu Leu
        35                  40                  45

Tyr Ser Tyr Ser Thr Leu Val Arg Pro Thr Asp Leu Ser Leu Ile Ser
    50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu Xaa
                85                  90                  95
```

```
Gly Arg Ile Trp Xaa Gly His Asn Ile Lys Arg Phe Asp Cys Val Arg
            100                 105                 110

Ile Xaa Asp Ala Phe Ala Xaa Ile Gly Leu Xaa Pro Pro Glu Pro Lys
        115                 120                 125

Ala Thr Ile Asp Ser Leu Ser Leu Xaa Ser Gln Lys Phe Gly Lys Arg
        130                 135                 140

Ala Gly Asp Met Lys Met Ala Ser Xaa Ala Thr Tyr Phe Xaa Leu Gly
145                 150                 155                 160

Asp Gln Ala His Arg Ser Leu Asp Asp Val Arg Met Asn Leu Glu Val
                165                 170                 175

Xaa Lys Xaa Cys Ser Thr Val Leu Phe Leu Glu Ser Val Pro Asp
        180                 185                 190

Ile Leu Xaa Xaa Xaa Ser Trp Xaa Xaa Pro Arg Lys Ser Pro Xaa Thr
        195                 200                 205

Arg Ser Asn Glu Lys Ser Leu Pro Xaa Gly Val Arg Glu Ser Pro Thr
        210                 215                 220

Ser Ser Ser Xaa Ser Pro Xaa Thr Asp Pro Ser Ser Ser Ser Val Asp
225                 230                 235                 240

Ala Thr Xaa Val Lys Asn His Pro Ile Ile Ser Leu Leu Thr Glu Cys
        245                 250                 255

Ser Xaa Ser Asp Thr Ser Ser Cys Glu Ile Asp Pro Ser Asp Ile Thr
        260                 265                 270

Thr Leu Ile Ser Lys Leu His Ile Gly Thr Leu Lys Xaa Asp Ala Ala
        275                 280                 285

Asp Glu Ala Lys Xaa Val Arg Gln Gln Gly Glu Ser Thr Asp Pro Asn
290                 295                 300

Ala Lys Asp Glu Ser Phe Leu Gly Val Asn Glu Val Ser Val Ser Xaa
305                 310                 315                 320

Ile Arg Ala Ser Leu Ile Pro Leu Tyr Arg Xaa Xaa Leu Arg Met Glu
        325                 330                 335

Leu Xaa His Asn Asp Xaa Pro Xaa His Leu Cys Trp Tyr Ser Leu Lys
        340                 345                 350

Ile Arg Phe Gly Ile Ser Arg Lys Tyr Val Asp His Val Gly Arg Pro
        355                 360                 365

Lys Met Asn Ile Val Val Asp Ile Xaa Pro Asp Leu Cys Lys Ile Leu
        370                 375                 380

Asp Ala Xaa Asp Ala Ala His Asn Leu Leu Ile Asp Ser Ser Thr
385                 390                 395                 400

Xaa Ser Asp Xaa Arg Pro Thr Val Met Xaa Lys Xaa Gly Phe Xaa Asn
        405                 410                 415

Tyr Pro Thr Ala Arg Leu Gln Ile Ser Ser Glu Ser Asn Gly Thr Gln
        420                 425                 430

Val Xaa Gln Lys Glu Glu Pro Leu Gly Thr Asn Gln Lys Leu Asp Phe
        435                 440                 445

Ser Ser Asp Asn Phe Glu Lys Leu Glu Ser Ala Leu Leu Pro Gly Thr
        450                 455                 460

Leu Val Asp Xaa Phe Phe Ser Xaa Glu Xaa Tyr Asp Tyr Lys Lys Met
465                 470                 475                 480

Val Gly Ile Xaa Leu Ala Ala Arg Lys Leu Val Ile Gln Leu Lys Lys
        485                 490                 495

<210> SEQ ID NO 9
<211> LENGTH: 496
```

```
<212> TYPE: PRT
<213> ORGANISM: Boechera
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(130)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (136)..(137)
<223> OTHER INFORMATION: Xaa can be any naturally occurring amino acid
<220> FEATURE:
```

```
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (200)..(202)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
```

```
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (331)..(332)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (387)..(388)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (403)..(404)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (438)..(438)
```

```
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid

<400> SEQUENCE: 9

Met Ala Ser Thr Leu Gly Xaa Asp Xaa Arg Xaa Glu Ile Val Phe Phe
1               5                   10                  15

Asp Leu Glu Thr Ala Val Xaa Thr Xaa Ser Gly Gln Pro Phe Ala Ile
            20                  25                  30

Leu Glu Phe Gly Ala Ile Leu Val Cys Pro Met Lys Leu Xaa Glu Leu
        35                  40                  45

Tyr Ser Tyr Xaa Thr Leu Xaa Arg Pro Thr Asp Leu Ser Leu Ile Xaa
    50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Xaa Tyr Asp Ile Xaa His
                85                  90                  95

Gly Arg Ile Trp Ala Gly His Asn Ile Lys Arg Phe Asp Cys Val Arg
            100                 105                 110

Xaa Xaa Asp Ala Phe Ala Xaa Ile Gly Xaa Xaa Pro Xaa Glu Xaa Lys
        115                 120                 125

Xaa Xaa Ile Asp Xaa Leu Ser Xaa Xaa Ser Gln Lys Phe Gly Lys Xaa
    130                 135                 140

Ala Gly Asp Xaa Lys Met Ala Xaa Xaa Ala Thr Tyr Phe Xaa Leu Gly
145                 150                 155                 160

Asp Gln Ala His Arg Ser Leu Asp Asp Val Arg Met Asn Leu Glu Val
                165                 170                 175

Xaa Lys Xaa Cys Xaa Thr Xaa Leu Phe Leu Glu Ser Ser Val Pro Asp
            180                 185                 190

Ile Leu Xaa Xaa Met Ser Trp Xaa Xaa Xaa Arg Lys Ser Xaa Arg Thr
        195                 200                 205

Arg Ser Asn Glu Lys Ser Leu Pro Asn Gly Val Arg Glu Ser Pro Thr
    210                 215                 220

Ser Ser Ser Ser Pro Lys Xaa Asp Pro Ser Ser Ser Val Xaa
225                 230                 235                 240

Ala Thr Xaa Val Lys Asn His Pro Ile Ile Ser Leu Leu Thr Glu Cys
                245                 250                 255
```

```
Ser Glu Xaa Asp Thr Ser Ser Xaa Glu Ile Asp Pro Ser Asp Ile Thr
            260                 265                 270

Thr Leu Ile Ser Lys Leu His Ile Gly Thr Leu Lys Xaa Asp Ala Ala
            275                 280                 285

Xaa Glu Ala Lys Xaa Val Arg Gln Gln Gly Glu Ser Thr Asp Pro Asn
290                 295                 300

Ala Lys Asp Glu Ser Phe Xaa Gly Val Asn Glu Val Ser Xaa Ser Ser
305                 310                 315                 320

Xaa Arg Ala Ser Leu Xaa Pro Leu Tyr Arg Xaa Xaa Leu Arg Met Glu
                325                 330                 335

Leu Xaa His Asn Xaa Thr Pro Leu His Leu Xaa Trp Tyr Xaa Xaa Lys
            340                 345                 350

Ile Arg Phe Gly Ile Ser Arg Lys Xaa Val Asp His Val Gly Arg Pro
            355                 360                 365

Lys Met Asn Ile Val Val Asp Ile Pro Pro Asp Leu Cys Lys Ile Leu
            370                 375                 380

Asp Ala Xaa Xaa Ala Xaa Ala His Asn Leu Leu Ile Asp Ser Ser Thr
385                 390                 395                 400

Xaa Ser Xaa Xaa Arg Pro Thr Val Met Xaa Lys Xaa Gly Phe Ala Asn
                405                 410                 415

Tyr Pro Thr Ala Xaa Leu Gln Ile Ser Ser Glu Ser Asn Xaa Thr Xaa
            420                 425                 430

Val Xaa Gln Lys Glu Xaa Pro Leu Gly Thr Asn Gln Lys Leu Asp Phe
        435                 440                 445

Ser Ser Asp Asn Phe Glu Lys Leu Glu Ser Ala Leu Xaa Pro Gly Xaa
450                 455                 460

Leu Val Asp Xaa Phe Phe Ser Xaa Glu Xaa Tyr Asp Tyr Xaa Lys Met
465                 470                 475                 480

Val Gly Ile Arg Leu Ala Ala Arg Lys Leu Val Ile Xaa Leu Lys Lys
            485                 490                 495

<210> SEQ ID NO 10
<211> LENGTH: 165
<212> TYPE: PRT
<213> ORGANISM: Boechera

<400> SEQUENCE: 10

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
            20                  25                  30

Val Glu Leu Tyr Ser Tyr Ser Thr Leu Val Arg Pro Thr Asp Leu Ser
            35                  40                  45

Leu Ile Ser Thr Leu Thr Lys Arg Arg Ser Gly Ile Thr Arg Asp Gly
        50                  55                  60

Val Leu Ser Ala Pro Thr Phe Ser Glu Ile Ala Asp Glu Val Tyr Asp
65                  70                  75                  80

Ile Leu His Gly Arg Ile Trp Val Gly His Asn Ile Lys Arg Phe Asp
            85                  90                  95

Cys Val Arg Ile Arg Asp Ala Phe Ala Glu Ile Gly Leu Pro Pro Pro
            100                 105                 110

Glu Pro Lys Ala Thr Ile Asp Ser Leu Ser Leu Leu Ser Gln Lys Phe
        115                 120                 125

Gly Lys Arg Ala Gly Asp Met Lys Met Ala Ser His Ala Thr Tyr Phe
```

```
                130                 135                 140
Gly Leu Gly Asp Gln Ala His Arg Ser Leu Asp Asp Val Arg Met Asn
145                 150                 155                 160

Leu Glu Val Ile Lys
                165

<210> SEQ ID NO 11
<211> LENGTH: 165
<212> TYPE: PRT
<213> ORGANISM: Boechera

<400> SEQUENCE: 11

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
                20                  25                  30

Val Glu Leu Tyr Ser Tyr Ser Thr Leu Val Arg Pro Thr Asp Leu Ser
            35                  40                  45

Leu Ile Ser Thr Leu Thr Lys Arg Arg Ser Gly Ile Thr Arg Asp Gly
        50                  55                  60

Val Leu Ser Ala Pro Thr Phe Ser Glu Ile Ala Asp Glu Val Tyr Asp
65                  70                  75                  80

Ile Leu His Gly Arg Ile Trp Ala Gly His Asn Ile Lys Arg Phe Asp
                85                  90                  95

Cys Val Arg Ile Arg Asp Ala Phe Ala Glu Ile Gly Leu Pro Pro Pro
            100                 105                 110

Glu Pro Lys Ala Thr Ile Asp Ser Leu Ser Leu Leu Ser Gln Lys Phe
        115                 120                 125

Gly Lys Arg Ala Gly Asp Met Lys Met Ala Ser Leu Ala Thr Tyr Phe
    130                 135                 140

Gly Leu Gly Asp Gln Ala His Arg Ser Leu Asp Asp Val Arg Met Asn
145                 150                 155                 160

Leu Glu Val Ile Lys
                165

<210> SEQ ID NO 12
<211> LENGTH: 165
<212> TYPE: PRT
<213> ORGANISM: Boechera

<400> SEQUENCE: 12

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
                20                  25                  30

Val Glu Leu Tyr Ser Tyr Ser Thr Leu Val Arg Pro Thr Asp Leu Ser
            35                  40                  45

Leu Ile Ser Thr Leu Thr Lys Arg Arg Ser Gly Ile Thr Arg Asp Gly
        50                  55                  60

Val Leu Ser Ala Pro Thr Phe Ser Glu Ile Ala Asp Glu Val Tyr Asp
65                  70                  75                  80

Ile Leu His Gly Arg Ile Trp Ala Gly His Asn Ile Lys Arg Phe Asp
                85                  90                  95

Cys Val Arg Ile Arg Asp Ala Phe Ala Glu Ile Gly Leu Pro Pro Pro
            100                 105                 110

Glu Pro Lys Ala Thr Ile Asp Ser Leu Ser Leu Leu Ser Gln Lys Phe
        115                 120                 125
```

```
            115                 120                 125
Gly Lys Arg Ala Gly Asp Met Lys Met Ala Ser Leu Ala Thr Tyr Phe
        130                 135                 140
Gly Leu Gly Asp Gln Ala His Arg Ser Leu Asp Asp Val Arg Met Asn
145                 150                 155                 160
Leu Glu Val Ile Lys
            165

<210> SEQ ID NO 13
<211> LENGTH: 496
<212> TYPE: PRT
<213> ORGANISM: Boechera

<400> SEQUENCE: 13

Met Ala Ser Thr Leu Gly Gly Asp Glu Arg Asn Glu Ile Val Phe Phe
1               5                   10                  15
Asp Leu Glu Thr Ala Val Pro Thr Lys Ser Gly Gln Pro Phe Ala Ile
            20                  25                  30
Leu Glu Phe Gly Ala Ile Leu Val Cys Pro Met Lys Leu Val Glu Leu
        35                  40                  45
Tyr Ser Tyr Ser Thr Leu Val Arg Pro Thr Asp Leu Ser Leu Ile Ser
    50                  55                  60
Thr Leu Thr Lys Arg Arg Ser Gly Ile Thr Arg Asp Gly Val Leu Ser
65                  70                  75                  80
Ala Pro Thr Phe Ser Glu Ile Ala Asp Glu Val Tyr Asp Ile Leu His
                85                  90                  95
Gly Arg Ile Trp Val Gly His Asn Ile Lys Arg Phe Asp Cys Val Arg
            100                 105                 110
Ile Arg Asp Ala Phe Ala Glu Ile Gly Leu Pro Pro Pro Glu Pro Lys
        115                 120                 125
Ala Thr Ile Asp Ser Leu Ser Leu Leu Ser Gln Lys Phe Gly Lys Arg
    130                 135                 140
Ala Gly Asp Met Lys Met Ala Ser His Ala Thr Tyr Phe Gly Leu Gly
145                 150                 155                 160
Asp Gln Ala His Arg Ser Leu Asp Asp Val Arg Met Asn Leu Glu Val
                165                 170                 175
Ile Lys His Cys Ser Thr Val Leu Phe Leu Glu Ser Ser Val Pro Asp
            180                 185                 190
Ile Leu Thr Asp Met Ser Trp Leu Phe Pro Arg Lys Ser Pro Arg Thr
        195                 200                 205
Arg Ser Asn Glu Lys Ser Leu Pro Asn Gly Val Arg Glu Ser Pro Thr
    210                 215                 220
Ser Ser Ser Ser Ser Pro Lys Thr Asp Pro Ser Ser Ser Val Asp
225                 230                 235                 240
Ala Thr Ala Val Lys Asn His Pro Ile Ile Ser Leu Leu Thr Glu Cys
                245                 250                 255
Ser Glu Ser Asp Thr Ser Ser Cys Glu Ile Asp Pro Ser Asp Ile Thr
            260                 265                 270
Thr Leu Ile Ser Lys Leu His Ile Gly Thr Leu Lys Thr Asp Ala Ala
        275                 280                 285
Asp Glu Ala Lys Thr Val Arg Gln Gln Gly Glu Ser Thr Asp Pro Asn
    290                 295                 300
Ala Lys Asp Glu Ser Phe Leu Gly Val Asn Glu Val Ser Val Ser Ser
305                 310                 315                 320
```

```
Ile Arg Ala Ser Leu Ile Pro Leu Tyr Arg Arg Ser Leu Arg Met Glu
            325                 330                 335

Leu Phe His Asn Asp Thr Pro Leu His Leu Cys Trp Tyr Ser Leu Lys
            340                 345                 350

Ile Arg Phe Gly Ile Ser Arg Lys Tyr Val Asp His Val Gly Arg Pro
            355                 360                 365

Lys Met Asn Ile Val Val Asp Ile Pro Pro Asp Leu Cys Lys Ile Leu
            370                 375                 380

Asp Ala Ser Asp Ala Ala His Asn Leu Leu Ile Asp Ser Ser Thr
385                 390                 395                 400

Ser Ser Asp Trp Arg Pro Thr Val Met Arg Lys Lys Gly Phe Ala Asn
            405                 410                 415

Tyr Pro Thr Ala Arg Leu Gln Ile Ser Ser Glu Ser Asn Gly Thr Gln
            420                 425                 430

Val His Gln Lys Glu Glu Pro Leu Gly Thr Asn Gln Lys Leu Asp Phe
            435                 440                 445

Ser Ser Asp Asn Phe Glu Lys Leu Glu Ser Ala Leu Leu Pro Gly Thr
            450                 455                 460

Leu Val Asp Ala Phe Phe Ser Leu Glu Pro Tyr Asp Tyr Lys Lys Met
465                 470                 475                 480

Val Gly Ile Arg Leu Ala Ala Arg Lys Leu Val Ile His Leu Lys Lys
            485                 490                 495

<210> SEQ ID NO 14
<211> LENGTH: 496
<212> TYPE: PRT
<213> ORGANISM: Boechera

<400> SEQUENCE: 14

Met Ala Ser Thr Leu Gly Gly Asp Glu Arg Asn Glu Ile Val Phe Phe
1               5                   10                  15

Asp Leu Glu Thr Ala Val Pro Thr Lys Ser Gly Gln Pro Phe Ala Ile
            20                  25                  30

Leu Glu Phe Gly Ala Ile Leu Val Cys Pro Met Lys Leu Val Glu Leu
            35                  40                  45

Tyr Ser Tyr Ser Thr Leu Val Arg Pro Thr Asp Leu Ser Leu Ile Ser
        50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu His
            85                  90                  95

Gly Arg Ile Trp Ala Gly His Asn Ile Lys Arg Phe Asp Cys Val Arg
            100                 105                 110

Ile Arg Asp Ala Phe Ala Glu Ile Gly Leu Pro Pro Glu Pro Lys
            115                 120                 125

Ala Thr Ile Asp Ser Leu Ser Leu Leu Ser Gln Lys Phe Gly Lys Arg
            130                 135                 140

Ala Gly Asp Met Lys Met Ala Ser Leu Ala Thr Tyr Phe Gly Leu Gly
145                 150                 155                 160

Asp Gln Ala His Arg Ser Leu Asp Asp Val Arg Met Asn Leu Glu Val
            165                 170                 175

Ile Lys His Cys Ser Thr Val Leu Phe Leu Glu Ser Val Pro Asp
            180                 185                 190

Ile Leu Thr Asp Met Ser Trp Leu Phe Pro Arg Lys Ser Pro Arg Thr
            195                 200                 205
```

Arg Ser Asn Glu Lys Ser Leu Pro Asn Gly Val Arg Glu Ser Pro Thr
210                 215                 220

Ser Ser Ser Ser Ser Pro Gln Thr Asp Pro Ser Ser Ser Ser Val Asp
225                 230                 235                 240

Ala Thr Ala Val Lys Asn His Pro Ile Ile Ser Leu Leu Thr Glu Cys
                245                 250                 255

Ser Glu Ser Asp Thr Ser Ser Cys Glu Ile Asp Pro Ser Asp Ile Thr
                260                 265                 270

Thr Leu Ile Ser Lys Leu His Ile Gly Thr Leu Lys Thr Asp Ala Ala
                275                 280                 285

Asp Glu Ala Lys Thr Val Arg Gln Gln Gly Ser Thr Asp Pro Asn
290                 295                 300

Ala Lys Asp Glu Ser Phe Leu Gly Val Asn Glu Val Ser Val Ser Ser
305                 310                 315                 320

Ile Arg Ala Ser Leu Ile Pro Leu Tyr Arg Arg Ser Leu Arg Met Glu
                325                 330                 335

Leu Phe His Asn Asp Thr Pro Leu His Leu Cys Trp Tyr Ser Leu Lys
                340                 345                 350

Ile Arg Phe Gly Ile Ser Arg Lys Tyr Val Asp His Val Gly Arg Pro
                355                 360                 365

Lys Met Asn Ile Val Val Asp Ile Pro Pro Asp Leu Cys Lys Ile Leu
                370                 375                 380

Asp Ala Ser Asp Ala Ala His Asn Leu Leu Ile Asp Ser Ser Thr
385                 390                 395                 400

Ser Ser Asp Trp Arg Pro Thr Val Met Arg Lys Lys Gly Phe Ala Asn
                405                 410                 415

Tyr Pro Thr Ala Arg Leu Gln Ile Ser Ser Glu Ser Asn Gly Thr Gln
                420                 425                 430

Val Tyr Gln Lys Glu Glu Pro Leu Gly Thr Asn Gln Lys Leu Asp Phe
                435                 440                 445

Ser Ser Asp Asn Phe Glu Lys Leu Glu Ser Ala Leu Leu Pro Gly Thr
450                 455                 460

Leu Val Asp Val Phe Phe Ser Val Glu Pro Tyr Asp Tyr Lys Lys Met
465                 470                 475                 480

Val Gly Ile Arg Leu Ala Ala Arg Lys Leu Val Ile Gln Leu Lys Lys
                485                 490                 495

<210> SEQ ID NO 15
<211> LENGTH: 496
<212> TYPE: PRT
<213> ORGANISM: Boechera

<400> SEQUENCE: 15

Met Ala Ser Thr Leu Gly Gly Asp Glu Arg Asn Glu Ile Val Phe Phe
1               5                   10                  15

Asp Leu Glu Thr Ala Val Pro Thr Lys Ser Gly Gln Pro Phe Ala Ile
                20                  25                  30

Leu Glu Phe Gly Ala Ile Leu Val Cys Pro Met Lys Leu Val Glu Leu
                35                  40                  45

Tyr Ser Tyr Ser Thr Leu Val Arg Pro Thr Asp Leu Ser Leu Ile Ser
                50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu His

```
            85                  90                  95
Gly Arg Ile Trp Ala Gly His Asn Ile Lys Arg Phe Asp Cys Val Arg
            100                 105                 110

Ile Arg Asp Ala Phe Ala Glu Ile Gly Leu Pro Pro Glu Pro Lys
            115                 120                 125

Ala Thr Ile Asp Ser Leu Ser Leu Leu Ser Gln Lys Phe Gly Lys Arg
            130                 135                 140

Ala Gly Asp Met Lys Met Ala Ser Leu Ala Thr Tyr Phe Gly Leu Gly
145                 150                 155                 160

Asp Gln Ala His Arg Ser Leu Asp Asp Val Arg Met Asn Leu Glu Val
            165                 170                 175

Ile Lys His Cys Ala Thr Val Leu Phe Leu Glu Ser Ser Val Pro Asp
            180                 185                 190

Ile Leu Thr Asp Met Ser Trp Leu Phe Pro Arg Lys Ser Pro Arg Thr
            195                 200                 205

Arg Ser Asn Glu Lys Ser Leu Pro Asn Gly Val Arg Glu Ser Pro Thr
            210                 215                 220

Ser Ser Ser Ser Ser Pro Lys Thr Asp Pro Ser Ser Ser Ser Val Asp
225                 230                 235                 240

Ala Thr Ala Val Lys Asn His Pro Ile Ile Ser Leu Leu Thr Glu Cys
            245                 250                 255

Ser Glu Ser Asp Thr Ser Ser Cys Glu Ile Asp Pro Ser Asp Ile Thr
            260                 265                 270

Thr Leu Ile Ser Lys Leu His Ile Gly Thr Leu Lys Arg Asp Ala Ala
            275                 280                 285

Asp Glu Ala Lys Ile Val Arg Gln Gln Gly Glu Ser Thr Asp Pro Asn
            290                 295                 300

Ala Lys Asp Glu Ser Phe Leu Gly Val Asn Glu Val Ser Val Ser Ser
305                 310                 315                 320

Ile Arg Ala Ser Leu Ile Pro Leu Tyr Arg Gly Ser Leu Arg Met Glu
            325                 330                 335

Leu Phe His Asn Asp Thr Pro Leu His Leu Cys Trp Tyr Ser Leu Lys
            340                 345                 350

Ile Arg Phe Gly Ile Ser Arg Lys Tyr Val Asp His Val Gly Arg Pro
            355                 360                 365

Lys Met Asn Ile Val Val Asp Ile Pro Pro Asp Leu Cys Lys Ile Leu
            370                 375                 380

Asp Ala Tyr Asp Ala Ala Ala His Asn Leu Leu Ile Asp Ser Ser Thr
385                 390                 395                 400

Ser Ser Asp Trp Arg Pro Thr Val Met Arg Lys Glu Gly Phe Ala Asn
            405                 410                 415

Tyr Pro Thr Ala Arg Leu Gln Ile Ser Ser Glu Ser Asn Gly Thr Gln
            420                 425                 430

Val Tyr Gln Lys Glu Pro Leu Gly Thr Asn Gln Lys Leu Asp Phe
            435                 440                 445

Ser Ser Asp Asn Phe Glu Lys Leu Glu Ser Ala Leu Leu Pro Gly Thr
            450                 455                 460

Leu Val Asp Ala Phe Phe Ser Pro Glu Ser Tyr Asp Tyr Lys Lys Met
465                 470                 475                 480

Val Gly Ile Arg Leu Ala Ala Arg Lys Leu Val Ile His Leu Lys Lys
            485                 490                 495

<210> SEQ ID NO 16
```

```
<211> LENGTH: 165
<212> TYPE: PRT
<213> ORGANISM: Boechera

<400> SEQUENCE: 16

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
            20                  25                  30

Val Glu Leu Tyr Ser Tyr Ser Thr Leu Val Arg Pro Thr Asp Leu Ser
        35                  40                  45

Leu Ile Ser Thr Leu Thr Lys Arg Arg Ser Gly Ile Thr Arg Asp Gly
    50                  55                  60

Val Leu Ser Ala Pro Thr Phe Ser Glu Ile Ala Asp Glu Val Tyr Asp
65                  70                  75                  80

Ile Leu His Gly Arg Ile Trp Ala Gly His Asn Ile Lys Arg Phe Asp
                85                  90                  95

Cys Val Arg Ile Arg Asp Ala Phe Ala Gly Ile Gly Val Ser Pro Pro
                100                 105                 110

Glu Pro Lys Ala Thr Ile Asp Ser Leu Ser Leu Leu Ser Gln Lys Phe
            115                 120                 125

Gly Lys Arg Ala Gly Asp Met Lys Met Ala Ser Leu Ala Thr Tyr Phe
    130                 135                 140

Gly Leu Gly Asp Gln Ala His Arg Ser Leu Asp Asp Val Arg Met Asn
145                 150                 155                 160

Leu Glu Val Val Lys
            165

<210> SEQ ID NO 17
<211> LENGTH: 165
<212> TYPE: PRT
<213> ORGANISM: Boechera

<400> SEQUENCE: 17

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
            20                  25                  30

Val Glu Leu Tyr Ser Tyr Ser Thr Leu Val Arg Pro Thr Asp Leu Ser
        35                  40                  45

Leu Ile Ser Thr Leu Thr Lys Arg Arg Ser Gly Ile Thr Arg Asp Gly
    50                  55                  60

Val Leu Ser Ala Pro Thr Phe Ser Glu Ile Ala Asp Glu Val Tyr Asp
65                  70                  75                  80

Ile Leu His Gly Arg Ile Trp Ala Gly His Asn Ile Lys Arg Phe Asp
                85                  90                  95

Cys Val Arg Ile Arg Asp Ala Phe Ala Gly Ile Gly Leu Ser Pro Pro
                100                 105                 110

Glu Pro Lys Ala Thr Ile Asp Ser Leu Ser Leu Leu Ser Gln Lys Phe
            115                 120                 125

Gly Lys Arg Ala Gly Asp Met Lys Met Ala Ser Leu Ala Thr Tyr Phe
    130                 135                 140

Gly Leu Gly Asp Gln Ala His Arg Ser Leu Asp Asp Val Arg Met Asn
145                 150                 155                 160

Leu Glu Val Val Lys
            165
```

```
<210> SEQ ID NO 18
<211> LENGTH: 165
<212> TYPE: PRT
<213> ORGANISM: Boechera

<400> SEQUENCE: 18

Val Phe Phe Asp Leu Glu Thr Ala Val Pro Thr Lys Ser Gly Gln Pro
1               5                   10                  15

Phe Ala Ile Leu Glu Phe Gly Ala Ile Leu Val Cys Pro Met Lys Leu
            20                  25                  30

Val Glu Leu Tyr Ser Tyr Ser Thr Leu Val Arg Pro Thr Asp Leu Ser
        35                  40                  45

Leu Ile Ser Thr Leu Thr Lys Arg Arg Ser Gly Ile Thr Arg Asp Gly
    50                  55                  60

Val Leu Ser Ala Pro Thr Phe Ser Glu Ile Ala Asp Glu Val Tyr Asp
65                  70                  75                  80

Ile Leu His Gly Arg Ile Trp Ala Gly His Asn Ile Lys Arg Phe Asp
                85                  90                  95

Cys Val Arg Ile Arg Asp Ala Phe Ala Gly Ile Gly Leu Ser Pro Pro
            100                 105                 110

Glu Pro Lys Ala Thr Ile Asp Ser Leu Ser Leu Ser Gln Lys Phe
        115                 120                 125

Gly Lys Arg Ala Gly Asp Met Lys Met Ala Ser Leu Ala Thr Tyr Phe
    130                 135                 140

Gly Leu Gly Asp Gln Ala His Arg Ser Leu Asp Asp Val Arg Met Asn
145                 150                 155                 160

Leu Glu Val Val Lys
                165

<210> SEQ ID NO 19
<211> LENGTH: 506
<212> TYPE: PRT
<213> ORGANISM: Boechera

<400> SEQUENCE: 19

Met Ala Ser Thr Leu Gly Gly Asp Glu Arg Cys Glu Ile Val Phe Phe
1               5                   10                  15

Asp Leu Glu Thr Ala Val Pro Thr Lys Ser Gly Gln Pro Phe Ala Ile
            20                  25                  30

Leu Glu Phe Gly Ala Ile Leu Val Cys Pro Met Lys Leu Val Glu Leu
        35                  40                  45

Tyr Ser Tyr Ser Thr Leu Val Arg Pro Thr Asp Leu Ser Leu Ile Ser
    50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu His
                85                  90                  95

Gly Arg Ile Trp Ala Gly His Asn Ile Lys Arg Phe Asp Cys Val Arg
            100                 105                 110

Ile Arg Asp Ala Phe Ala Gly Ile Gly Val Ser Pro Pro Glu Pro Lys
        115                 120                 125

Ala Thr Ile Asp Ser Leu Ser Leu Ser Gln Lys Phe Gly Lys Arg
    130                 135                 140

Ala Gly Asp Met Lys Met Ala Ser Leu Ala Thr Tyr Phe Gly Leu Gly
145                 150                 155                 160
```

Asp Gln Ala His Arg Ser Leu Asp Asp Val Arg Met Asn Leu Glu Val
            165                 170                 175

Val Lys Tyr Cys Ala Thr Val Leu Phe Leu Glu Ser Val Pro Asp
        180                 185                 190

Ile Leu Lys Asp Met Ser Trp Phe Ser Pro Arg Lys Ser Pro Arg Thr
            195                 200                 205

Arg Ser Asn Glu Lys Ser Leu Pro Asn Gly Val Arg Glu Ser Pro Thr
        210                 215                 220

Ser Ser Ser Ser Ser Pro Lys Thr Asp Pro Ser Ser Ser Ser Val Asp
225                 230                 235                 240

Ala Thr Thr Val Lys Asn His Pro Ile Ile Ser Leu Leu Thr Glu Cys
            245                 250                 255

Ser Glu Ser Asp Thr Ser Ser Cys Glu Ile Asp Pro Ser Asp Ile Thr
        260                 265                 270

Thr Leu Ile Ser Lys Leu His Ile Gly Thr Leu Lys Arg Asp Ala Ala
            275                 280                 285

Asp Glu Ala Lys Thr Val Arg Asp Ala Ala Asp Glu Ala Lys Thr Val
        290                 295                 300

Arg Gln Gln Gly Glu Ser Thr Asp Pro Asn Ala Lys Asp Glu Ser Phe
305                 310                 315                 320

Leu Gly Val Asn Glu Val Ser Val Ser Ser Ile Arg Ala Ser Leu Ile
            325                 330                 335

Pro Leu Tyr Arg Gly Ser Leu Arg Met Glu Leu Phe His Asn Asp Thr
        340                 345                 350

Pro Leu His Leu Cys Trp Tyr Ser Leu Lys Ile Arg Phe Gly Ile Ser
            355                 360                 365

Arg Lys Tyr Val Asp His Val Gly Arg Pro Lys Met Asn Ile Val Val
        370                 375                 380

Asp Ile Pro Pro Asp Leu Cys Lys Ile Leu Asp Ala Ser Asp Ala Ala
385                 390                 395                 400

Ala His Asn Leu Leu Ile Asp Ser Ser Thr Ser Ser Asp Trp Arg Pro
            405                 410                 415

Thr Val Met Arg Lys Glu Gly Phe Ala Asn Tyr Pro Thr Ala Arg Leu
        420                 425                 430

Gln Ile Ser Ser Glu Ser Asn Gly Thr Gln Val His Gln Lys Glu Glu
            435                 440                 445

Pro Leu Gly Thr Asn Gln Lys Leu Asp Phe Ser Ser Asp Asn Phe Glu
        450                 455                 460

Lys Leu Glu Ser Ala Leu Leu Pro Gly Thr Leu Val Asp Ala Phe Phe
465                 470                 475                 480

Ser Leu Glu Pro Tyr Asp Tyr Lys Lys Met Val Gly Ile Arg Leu Ala
            485                 490                 495

Ala Arg Lys Leu Val Ile His Leu Lys Lys
            500                 505

<210> SEQ ID NO 20
<211> LENGTH: 496
<212> TYPE: PRT
<213> ORGANISM: Boechera

<400> SEQUENCE: 20

Met Ala Ser Thr Leu Gly Gly Asp Glu Arg Cys Glu Ile Val Phe Phe
1               5                   10                  15

Asp Leu Glu Thr Ala Val Pro Thr Lys Ser Gly Gln Pro Phe Ala Ile

```
                20                  25                  30
Leu Glu Phe Gly Ala Ile Leu Val Cys Pro Met Lys Leu Val Glu Leu
            35                  40                  45

Tyr Ser Tyr Ser Thr Leu Val Arg Pro Thr Asp Leu Ser Leu Ile Ser
            50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu His
                85                  90                  95

Gly Arg Ile Trp Ala Gly His Asn Ile Lys Arg Phe Asp Cys Val Arg
            100                 105                 110

Ile Arg Asp Ala Phe Ala Gly Ile Gly Leu Ser Pro Glu Pro Lys
            115                 120                 125

Ala Thr Ile Asp Ser Leu Ser Leu Leu Ser Gln Lys Phe Gly Lys Arg
            130                 135                 140

Ala Gly Asp Met Lys Met Ala Ser Leu Ala Thr Tyr Phe Gly Leu Gly
145                 150                 155                 160

Asp Gln Ala His Arg Ser Leu Asp Asp Val Arg Met Asn Leu Glu Val
                165                 170                 175

Val Lys Tyr Cys Ala Thr Val Leu Phe Leu Glu Ser Ser Val Pro Asp
            180                 185                 190

Ile Leu Lys Asp Met Ser Trp Phe Ser Pro Arg Lys Ser Pro Arg Thr
            195                 200                 205

Arg Ser Asn Glu Lys Ser Leu Pro Asn Gly Val Arg Glu Ser Pro Thr
            210                 215                 220

Ser Ser Ser Ser Ser Pro Lys Thr Asp Pro Ser Ser Ser Ser Val Asp
225                 230                 235                 240

Ala Thr Thr Val Lys Asn His Pro Ile Ile Ser Leu Leu Thr Glu Cys
                245                 250                 255

Ser Glu Ser Asp Thr Ser Ser Cys Glu Ile Asp Pro Ser Asp Ile Thr
            260                 265                 270

Thr Leu Ile Ser Lys Leu His Ile Gly Thr Leu Lys Arg Asp Ala Ala
            275                 280                 285

Asp Glu Ala Lys Ile Val Arg Gln Gln Gly Glu Ser Thr Asp Pro Asn
            290                 295                 300

Ala Lys Asp Glu Ser Phe Leu Gly Val Asn Glu Val Ser Val Ser Ser
305                 310                 315                 320

Ile Arg Ala Ser Leu Ile Pro Leu Tyr Arg Gly Ser Leu Arg Met Glu
                325                 330                 335

Leu Leu His Asn Asp Thr Pro Leu His Leu Cys Trp Tyr Ser Leu Lys
            340                 345                 350

Ile Arg Phe Gly Ile Ser Arg Lys Tyr Val Asp His Val Gly Arg Pro
            355                 360                 365

Lys Met Asn Ile Val Val Asp Ile Pro Pro Asp Leu Cys Lys Ile Leu
            370                 375                 380

Asp Ala Tyr Asp Ala Ala His Asn Leu Leu Ile Asp Ser Ser Thr
385                 390                 395                 400

Ser Ser Asp Trp Arg Pro Thr Val Met Arg Lys Glu Gly Phe Ala Asn
                405                 410                 415

Tyr Pro Thr Ala Arg Leu Gln Ile Ser Ser Glu Ser Asn Gly Thr Gln
            420                 425                 430

Val Tyr Gln Lys Glu Glu Pro Leu Gly Thr Asn Gln Lys Leu Asp Phe
            435                 440                 445
```

```
Ser Ser Asp Asn Phe Glu Lys Leu Glu Ser Ala Leu Leu Pro Gly Thr
    450                 455                 460

Leu Val Asp Ala Phe Phe Ser Leu Glu Ser Tyr Asp Tyr Lys Lys Met
465                 470                 475                 480

Val Gly Ile Arg Leu Ala Ala Arg Lys Leu Val Ile His Leu Lys Lys
                485                 490                 495
```

<210> SEQ ID NO 21
<211> LENGTH: 496
<212> TYPE: PRT
<213> ORGANISM: Boechera

<400> SEQUENCE: 21

```
Met Ala Ser Thr Leu Gly Gly Asp Gly Arg Cys Glu Ile Val Phe Phe
1               5                   10                  15

Asp Leu Glu Thr Ala Val Pro Thr Lys Ser Gly Gln Pro Phe Ala Ile
                20                  25                  30

Leu Glu Phe Gly Ala Ile Leu Val Cys Pro Met Lys Leu Val Glu Leu
            35                  40                  45

Tyr Ser Tyr Ser Thr Leu Val Arg Pro Thr Asp Leu Ser Leu Ile Ser
        50                  55                  60

Thr Leu Thr Lys Arg Arg Ser Gly Ile Thr Arg Asp Gly Val Leu Ser
65                  70                  75                  80

Ala Pro Thr Phe Ser Glu Ile Ala Asp Glu Val Tyr Asp Ile Leu His
                85                  90                  95

Gly Arg Ile Trp Ala Gly His Asn Ile Lys Arg Phe Asp Cys Val Arg
            100                 105                 110

Ile Arg Asp Ala Phe Ala Gly Ile Gly Leu Ser Pro Pro Glu Pro Lys
        115                 120                 125

Ala Thr Ile Asp Ser Leu Ser Leu Leu Ser Gln Lys Phe Gly Lys Arg
130                 135                 140

Ala Gly Asp Met Lys Met Ala Ser Leu Ala Thr Tyr Phe Gly Leu Gly
145                 150                 155                 160

Asp Gln Ala His Arg Ser Leu Asp Asp Val Arg Met Asn Leu Glu Val
                165                 170                 175

Val Lys Tyr Cys Ala Thr Val Leu Phe Leu Glu Ser Ser Val Pro Asp
            180                 185                 190

Ile Leu Lys Asp Met Ser Trp Phe Ser Pro Arg Lys Ser Pro Arg Thr
        195                 200                 205

Arg Ser Asn Glu Lys Ser Leu Pro Asn Gly Val Arg Glu Ser Pro Thr
210                 215                 220

Ser Ser Ser Ser Ser Pro Lys Thr Asp Pro Ser Ser Ser Ser Val Asp
225                 230                 235                 240

Ala Thr Thr Val Lys Asn His Pro Ile Ile Ser Leu Leu Thr Glu Cys
                245                 250                 255

Ser Glu Ser Asp Thr Ser Ser Cys Glu Ile Asp Pro Ser Asp Ile Thr
            260                 265                 270

Thr Leu Ile Ser Lys Leu His Ile Gly Thr Leu Lys Arg Asp Ala Ala
        275                 280                 285

Asp Glu Ala Lys Thr Val Arg Gln Gln Gly Ser Thr Asp Pro Asn
290                 295                 300

Ala Lys Asp Glu Ser Phe Leu Gly Val Asn Glu Val Ser Val Ser Ser
305                 310                 315                 320

Ile Arg Ala Ser Leu Ile Pro Leu Tyr Arg Gly Gly Leu Arg Met Glu
```

```
                            325                 330                 335
Leu Phe His Asn Asp Thr Pro Leu His Leu Arg Trp Tyr Ser Leu Lys
        340                 345                 350

Ile Arg Phe Gly Ile Ser Arg Lys Tyr Val Asp His Val Gly Arg Pro
        355                 360                 365

Lys Met Asn Ile Val Val Asp Ile Pro Pro Asp Leu Cys Lys Ile Leu
        370                 375                 380

Asp Ala Ser Asp Ala Ala Ala His Asn Leu Leu Ile Asp Ser Ser Thr
385                 390                 395                 400

Ser Ser Asp Trp Arg Pro Thr Val Met Arg Lys Glu Gly Phe Ala Asn
            405                 410                 415

Tyr Pro Thr Ala Arg Leu Gln Ile Ser Ser Glu Ser Asn Gly Thr Gln
            420                 425                 430

Val His Gln Lys Glu Glu Pro Leu Gly Thr Asn Gln Lys Leu Asp Phe
            435                 440                 445

Ser Ser Asp Asn Phe Glu Lys Leu Glu Ser Ala Leu Leu Pro Gly Thr
450                 455                 460

Leu Val Asp Ala Phe Phe Ser Leu Glu Pro Tyr Asp Tyr Lys Lys Met
465                 470                 475                 480

Val Gly Ile Arg Leu Ala Ala Arg Lys Leu Val Ile His Leu Lys Lys
            485                 490                 495
```

<210> SEQ ID NO 22
<211> LENGTH: 2423
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature

```
<222> LOCATION: (89)..(89)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (303)..(304)
<223> OTHER INFORMATION: n is a, c, g, or t
<220> FEATURE:
<221> NAME/KEY: misc_feature
<222> LOCATION: (312)..(317)
<223> OTHER INFORMATION: n is a, c, g, or t
<220> FEATURE:
<221> NAME/KEY: misc_feature
<222> LOCATION: (320)..(321)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
```

-continued

```
<221> NAME/KEY: misc_feature
<222> LOCATION: (325)..(326)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (385)..(386)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (457)..(458)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (491)..(493)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
```

-continued

```
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (658)..(662)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (708)..(708)
```

```
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (726)..(727)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
```

```
<222> LOCATION: (915)..(915)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (934)..(934)
<223> OTHER INFORMATION: n is a, c, g, or t
<220> FEATURE:
<221> NAME/KEY: misc_feature
<222> LOCATION: (939)..(940)
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t
<220> FEATURE:
<221> NAME/KEY: misc_feature
<222> LOCATION: (976)..(977)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1049)..(1050)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
```

-continued

```
<221> NAME/KEY: misc_feature
<222> LOCATION: (1109)..(1109)
<223> OTHER INFORMATION: n is a, c, g, or t
<220> FEATURE:
<221> NAME/KEY: misc_feature
<222> LOCATION: (1111)..(1112)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1127)..(1127)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1142)..(1142)
<223> OTHER INFORMATION: n is a, c, g, or t
<220> FEATURE:
<221> NAME/KEY: misc_feature
<222> LOCATION: (1144)..(1144)
<223> OTHER INFORMATION: n is a, c, g, or t
<220> FEATURE:
<221> NAME/KEY: misc_feature
<222> LOCATION: (1173)..(1174)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1216)..(1216)
<223> OTHER INFORMATION: n is a, c, g, or t
<220> FEATURE:
<221> NAME/KEY: misc_feature
<222> LOCATION: (1219)..(1219)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1252)..(1252)
<223> OTHER INFORMATION: n is a, c, g, or t
<220> FEATURE:
<221> NAME/KEY: misc_feature
<222> LOCATION: (1298)..(1298)
<223> OTHER INFORMATION: n is a, c, g, or t
<220> FEATURE:
<221> NAME/KEY: misc_feature
<222> LOCATION: (1301)..(1302)
<223> OTHER INFORMATION: n is a, c, g, or t
```

```
-continued

<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1420)..(1420)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1433)..(1433)
<223> OTHER INFORMATION: n is a, c, g, or t
<220> FEATURE:
<221> NAME/KEY: misc_feature
<222> LOCATION: (1446)..(1446)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t
<220> FEATURE:
<221> NAME/KEY: misc_feature
<222> LOCATION: (1500)..(1500)
<223> OTHER INFORMATION: n is a, c, g, or t
<220> FEATURE:
<221> NAME/KEY: misc_feature
<222> LOCATION: (1507)..(1507)
<223> OTHER INFORMATION: n is a, c, g, or t
<220> FEATURE:
<221> NAME/KEY: misc_feature
<222> LOCATION: (1514)..(1516)
<223> OTHER INFORMATION: n is a, c, g, or t
<220> FEATURE:
<221> NAME/KEY: misc_feature
<222> LOCATION: (1531)..(1531)
<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1546)..(1546)
<223> OTHER INFORMATION: n is a, c, g, or t
<220> FEATURE:
<221> NAME/KEY: misc_feature
<222> LOCATION: (1549)..(1549)
<223> OTHER INFORMATION: n is a, c, g, or t
<220> FEATURE:
<221> NAME/KEY: misc_feature
<222> LOCATION: (1567)..(1567)
<223> OTHER INFORMATION: n is a, c, g, or t
<220> FEATURE:
<221> NAME/KEY: misc_feature
<222> LOCATION: (1575)..(1575)
```

-continued

```
<223> OTHER INFORMATION: n is a, c, g, or t
<220> FEATURE:
<221> NAME/KEY: misc_feature
<222> LOCATION: (1578)..(1579)
<223> OTHER INFORMATION: n is a, c, g, or t
<220> FEATURE:
<221> NAME/KEY: misc_feature
<222> LOCATION: (1586)..(1586)
<223> OTHER INFORMATION: n is a, c, g, or t
<220> FEATURE:
<221> NAME/KEY: misc_feature
<222> LOCATION: (1594)..(1594)
<223> OTHER INFORMATION: n is a, c, g, or t
<220> FEATURE:
<221> NAME/KEY: misc_feature
<222> LOCATION: (1596)..(1596)
<223> OTHER INFORMATION: n is a, c, g, or t
<220> FEATURE:
<221> NAME/KEY: misc_feature
<222> LOCATION: (1604)..(1604)
<223> OTHER INFORMATION: n is a, c, g, or t
<220> FEATURE:
<221> NAME/KEY: misc_feature
<222> LOCATION: (1606)..(1606)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1637)..(1637)
<223> OTHER INFORMATION: n is a, c, g, or t
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (1674)..(1674)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1685)..(1685)
<223> OTHER INFORMATION: n is a, c, g, or t
<220> FEATURE:
<221> NAME/KEY: misc_feature
<222> LOCATION: (1715)..(1717)
<223> OTHER INFORMATION: n is a, c, g, or t
<220> FEATURE:
<221> NAME/KEY: misc_feature
<222> LOCATION: (1723)..(1723)
<223> OTHER INFORMATION: n is a, c, g, or t
<220> FEATURE:
<221> NAME/KEY: misc_feature
<222> LOCATION: (1757)..(1758)
<223> OTHER INFORMATION: n is a, c, g, or t
<220> FEATURE:
<221> NAME/KEY: misc_feature
<222> LOCATION: (1764)..(1765)
<223> OTHER INFORMATION: n is a, c, g, or t
<220> FEATURE:
<221> NAME/KEY: misc_feature
<222> LOCATION: (1776)..(1776)
<223> OTHER INFORMATION: n is a, c, g, or t
<220> FEATURE:
<221> NAME/KEY: misc_feature
<222> LOCATION: (1784)..(1784)
<223> OTHER INFORMATION: n is a, c, g, or t
<220> FEATURE:
<221> NAME/KEY: misc_feature
<222> LOCATION: (1789)..(1789)
<223> OTHER INFORMATION: n is a, c, g, or t
<220> FEATURE:
<221> NAME/KEY: misc_feature
```

```
<222> LOCATION: (1799)..(1799)
<223> OTHER INFORMATION: n is a, c, g, or t
<220> FEATURE:
<221> NAME/KEY: misc_feature
<222> LOCATION: (1812)..(1812)
<223> OTHER INFORMATION: n is a, c, g, or t
<220> FEATURE:
<221> NAME/KEY: misc_feature
<222> LOCATION: (1816)..(1816)
<223> OTHER INFORMATION: n is a, c, g, or t
<220> FEATURE:
<221> NAME/KEY: misc_feature
<222> LOCATION: (1832)..(1832)
<223> OTHER INFORMATION: n is a, c, g, or t
<220> FEATURE:
<221> NAME/KEY: misc_feature
<222> LOCATION: (1835)..(1835)
<223> OTHER INFORMATION: n is a, c, g, or t
<220> FEATURE:
<221> NAME/KEY: misc_feature
<222> LOCATION: (1847)..(1847)
<223> OTHER INFORMATION: n is a, c, g, or t
<220> FEATURE:
<221> NAME/KEY: misc_feature
<222> LOCATION: (1860)..(1860)
<223> OTHER INFORMATION: n is a, c, g, or t
<220> FEATURE:
<221> NAME/KEY: misc_feature
<222> LOCATION: (1866)..(1866)
<223> OTHER INFORMATION: n is a, c, g, or t
<220> FEATURE:
<221> NAME/KEY: misc_feature
<222> LOCATION: (1871)..(1871)
<223> OTHER INFORMATION: n is a, c, g, or t
<220> FEATURE:
<221> NAME/KEY: misc_feature
<222> LOCATION: (1874)..(1874)
<223> OTHER INFORMATION: n is a, c, g, or t
<220> FEATURE:
<221> NAME/KEY: misc_feature
<222> LOCATION: (1888)..(1888)
<223> OTHER INFORMATION: n is a, c, g, or t
<220> FEATURE:
<221> NAME/KEY: misc_feature
<222> LOCATION: (1901)..(1901)
<223> OTHER INFORMATION: n is a, c, g, or t
<220> FEATURE:
<221> NAME/KEY: misc_feature
<222> LOCATION: (1908)..(1909)
<223> OTHER INFORMATION: n is a, c, g, or t
<220> FEATURE:
<221> NAME/KEY: misc_feature
<222> LOCATION: (1911)..(1911)
<223> OTHER INFORMATION: n is a, c, g, or t
<220> FEATURE:
<221> NAME/KEY: misc_feature
<222> LOCATION: (1918)..(1918)
<223> OTHER INFORMATION: n is a, c, g, or t
<220> FEATURE:
<221> NAME/KEY: misc_feature
<222> LOCATION: (1924)..(1924)
<223> OTHER INFORMATION: n is a, c, g, or t
<220> FEATURE:
<221> NAME/KEY: misc_feature
<222> LOCATION: (1946)..(1946)
<223> OTHER INFORMATION: n is a, c, g, or t
<220> FEATURE:
<221> NAME/KEY: misc_feature
<222> LOCATION: (1951)..(1952)
<223> OTHER INFORMATION: n is a, c, g, or t
<220> FEATURE:
<221> NAME/KEY: misc_feature
<222> LOCATION: (1964)..(1966)
<223> OTHER INFORMATION: n is a, c, g, or t
<220> FEATURE:
<221> NAME/KEY: misc_feature
<222> LOCATION: (1976)..(1977)
<223> OTHER INFORMATION: n is a, c, g, or t
<220> FEATURE:
```

-continued

```
<221> NAME/KEY: misc_feature
<222> LOCATION: (1999)..(1999)
<223> OTHER INFORMATION: n is a, c, g, or t
<220> FEATURE:
<221> NAME/KEY: misc_feature
<222> LOCATION: (2003)..(2003)
<223> OTHER INFORMATION: n is a, c, g, or t
<220> FEATURE:
<221> NAME/KEY: misc_feature
<222> LOCATION: (2008)..(2008)
<223> OTHER INFORMATION: n is a, c, g, or t
<220> FEATURE:
<221> NAME/KEY: misc_feature
<222> LOCATION: (2020)..(2020)
<223> OTHER INFORMATION: n is a, c, g, or t
<220> FEATURE:
<221> NAME/KEY: misc_feature
<222> LOCATION: (2037)..(2037)
<223> OTHER INFORMATION: n is a, c, g, or t
<220> FEATURE:
<221> NAME/KEY: misc_feature
<222> LOCATION: (2052)..(2052)
<223> OTHER INFORMATION: n is a, c, g, or t
<220> FEATURE:
<221> NAME/KEY: misc_feature
<222> LOCATION: (2064)..(2064)
<223> OTHER INFORMATION: n is a, c, g, or t
<220> FEATURE:
<221> NAME/KEY: misc_feature
<222> LOCATION: (2079)..(2079)
<223> OTHER INFORMATION: n is a, c, g, or t
<220> FEATURE:
<221> NAME/KEY: misc_feature
<222> LOCATION: (2088)..(2088)
<223> OTHER INFORMATION: n is a, c, g, or t
<220> FEATURE:
<221> NAME/KEY: misc_feature
<222> LOCATION: (2092)..(2092)
<223> OTHER INFORMATION: n is a, c, g, or t
<220> FEATURE:
<221> NAME/KEY: misc_feature
<222> LOCATION: (2103)..(2103)
<223> OTHER INFORMATION: n is a, c, g, or t
<220> FEATURE:
<221> NAME/KEY: misc_feature
<222> LOCATION: (2109)..(2111)
<223> OTHER INFORMATION: n is a, c, g, or t
<220> FEATURE:
<221> NAME/KEY: misc_feature
<222> LOCATION: (2120)..(2121)
<223> OTHER INFORMATION: n is a, c, g, or t
<220> FEATURE:
<221> NAME/KEY: misc_feature
<222> LOCATION: (2123)..(2123)
<223> OTHER INFORMATION: n is a, c, g, or t
<220> FEATURE:
<221> NAME/KEY: misc_feature
<222> LOCATION: (2125)..(2125)
<223> OTHER INFORMATION: n is a, c, g, or t
<220> FEATURE:
<221> NAME/KEY: misc_feature
<222> LOCATION: (2128)..(2128)
<223> OTHER INFORMATION: n is a, c, g, or t
<220> FEATURE:
<221> NAME/KEY: misc_feature
<222> LOCATION: (2131)..(2131)
<223> OTHER INFORMATION: n is a, c, g, or t
<220> FEATURE:
<221> NAME/KEY: misc_feature
<222> LOCATION: (2133)..(2133)
<223> OTHER INFORMATION: n is a, c, g, or t
<220> FEATURE:
<221> NAME/KEY: misc_feature
<222> LOCATION: (2135)..(2135)
<223> OTHER INFORMATION: n is a, c, g, or t
<220> FEATURE:
<221> NAME/KEY: misc_feature
<222> LOCATION: (2143)..(2143)
<223> OTHER INFORMATION: n is a, c, g, or t
```

-continued

```
<220> FEATURE:
<221> NAME/KEY: misc_feature
<222> LOCATION: (2155)..(2155)
<223> OTHER INFORMATION: n is a, c, g, or t
<220> FEATURE:
<221> NAME/KEY: misc_feature
<222> LOCATION: (2165)..(2165)
<223> OTHER INFORMATION: n is a, c, g, or t
<220> FEATURE:
<221> NAME/KEY: misc_feature
<222> LOCATION: (2172)..(2172)
<223> OTHER INFORMATION: n is a, c, g, or t
<220> FEATURE:
<221> NAME/KEY: misc_feature
<222> LOCATION: (2177)..(2177)
<223> OTHER INFORMATION: n is a, c, g, or t
<220> FEATURE:
<221> NAME/KEY: misc_feature
<222> LOCATION: (2190)..(2190)
<223> OTHER INFORMATION: n is a, c, g, or t
<220> FEATURE:
<221> NAME/KEY: misc_feature
<222> LOCATION: (2245)..(2245)
<223> OTHER INFORMATION: n is a, c, g, or t
<220> FEATURE:
<221> NAME/KEY: misc_feature
<222> LOCATION: (2257)..(2258)
<223> OTHER INFORMATION: n is a, c, g, or t
<220> FEATURE:
<221> NAME/KEY: misc_feature
<222> LOCATION: (2263)..(2263)
<223> OTHER INFORMATION: n is a, c, g, or t
<220> FEATURE:
<221> NAME/KEY: misc_feature
<222> LOCATION: (2267)..(2267)
<223> OTHER INFORMATION: n is a, c, g, or t
<220> FEATURE:
<221> NAME/KEY: misc_feature
<222> LOCATION: (2278)..(2281)
<223> OTHER INFORMATION: n is a, c, g, or t
<220> FEATURE:
<221> NAME/KEY: misc_feature
<222> LOCATION: (2291)..(2292)
<223> OTHER INFORMATION: n is a, c, g, or t
<220> FEATURE:
<221> NAME/KEY: misc_feature
<222> LOCATION: (2296)..(2297)
<223> OTHER INFORMATION: n is a, c, g, or t
<220> FEATURE:
<221> NAME/KEY: misc_feature
<222> LOCATION: (2310)..(2310)
<223> OTHER INFORMATION: n is a, c, g, or t
<220> FEATURE:
<221> NAME/KEY: misc_feature
<222> LOCATION: (2356)..(2356)
<223> OTHER INFORMATION: n is a, c, g, or t
<220> FEATURE:
<221> NAME/KEY: misc_feature
<222> LOCATION: (2392)..(2392)
<223> OTHER INFORMATION: n is a, c, g, or t
<220> FEATURE:
<221> NAME/KEY: misc_feature
<222> LOCATION: (2402)..(2402)
<223> OTHER INFORMATION: n is a, c, g, or t
<220> FEATURE:
<221> NAME/KEY: misc_feature
<222> LOCATION: (2406)..(2406)
<223> OTHER INFORMATION: n is a, c, g, or t
<220> FEATURE:
<221> NAME/KEY: misc_feature
<222> LOCATION: (2408)..(2408)
<223> OTHER INFORMATION: n is a, c, g, or t
<220> FEATURE:
<221> NAME/KEY: misc_feature
<222> LOCATION: (2415)..(2415)
<223> OTHER INFORMATION: n is a, c, g, or t
<220> FEATURE:
<221> NAME/KEY: misc_feature
<222> LOCATION: (2417)..(2417)
```

<223> OTHER INFORMATION: n is a, c, g, or t
<220> FEATURE:
<221> NAME/KEY: misc_feature
<222> LOCATION: (2419)..(2419)
<223> OTHER INFORMATION: n is a, c, g, or t
<220> FEATURE:
<221> NAME/KEY: misc_feature
<222> LOCATION: (2421)..(2423)
<223> OTHER INFORMATION: n is a, c, g, or t

<400> SEQUENCE: 22

| | | | | | |
|---|---|---|---|---|---|
| atggcttcga | ctctgggcng | cgatgngagn | nncgagatag | tgttttcga | tcttgagacn | 60 |
| gcngttncga | ccnaatcggg | ncanccntnt | gcgattttgg | agtttggngc | tatcttagtt | 120 |
| tgccctatga | agctagngga | gctctatagt | tacnccacnt | tggntcgacc | nacnganctt | 180 |
| tcnctcatct | ncacgctcac | gaagcgacga | agcggcatta | cgcgcgacgg | agttctctct | 240 |
| gcacctacnt | tctctgaaat | cgctgatgaa | ntctacgana | ttcnccncgg | taagggtttc | 300 |
| tcnttttttt | tnnnnnnctn | ncncnntctc | tctnacncga | agntanaagt | attgattttg | 360 |
| gtgtttctgt | aggacgaatt | tgggnnggac | ataacataaa | gagattcgat | tgtgtaagan | 420 |
| tangagatgc | atttgcagna | attggtntcn | ctccccnnga | gncnaaagnt | ncaattgatn | 480 |
| cactttcgtt | nnngtctcag | aagtttggga | agngagctgg | ngacntgaag | gtctctcttt | 540 |
| tttcgtcttc | ncgatgataa | atctcaaagc | cnatagcttn | cttgttatcn | ttatagatat | 600 |
| gaatttcnan | gtaacttcan | agattcatca | ctcatcanag | tngctaaaat | ttacnctnnn | 660 |
| nnaanaangt | agatggcntn | gcntgctacn | tatttcgngc | taggaganca | ngctcacagg | 720 |
| tnaaanngt | aaacgatacn | ntgtgcctt | taacgattcn | ccagttgtnt | caatatggga | 780 |
| ctaaacatgg | ntangattca | ncaggagctt | agatgatgtc | cggatgaatc | ttgaagtnnt | 840 |
| caagnactgt | ncaaccntct | tntttctggt | attgntgtct | tntcatttct | tgaataatga | 900 |
| tnaactcnta | anttnaaaag | gantagatta | nagnggttnn | gacatatctg | anttctgtct | 960 |
| ncngttntgn | aaaagnnggn | tcnatcttcc | ttncagacca | canctttgca | agccgtaaac | 1020 |
| atggnttgca | acttgcaagt | atagtttgnn | atatcactga | gtttaagtac | ttggtgtttg | 1080 |
| caggagtcna | gtgtnccnga | cattcttana | nncatnagct | ggttntnccn | aagaaaaagt | 1140 |
| cngngaacac | gaagtaatga | gaagtcactg | ccnnatggag | tcagagaaag | cccnacttct | 1200 |
| tcctcttcna | gccctaaanc | tganccgagt | tcgtcttctg | tanangcnac | anctgtcaaa | 1260 |
| aaccatccca | tcatttctct | tctgacggaa | tgctcagnaa | nngatacatc | tagttgngaa | 1320 |
| atagatccat | cngacataac | cactctaata | agtaaactac | atattggaac | tcttaagana | 1380 |
| gatgctgcgg | acgaagccaa | aactgtgaga | gangcngcgn | angaagccaa | nantgtaaga | 1440 |
| cagcanggtg | aatcaaccga | tcccaatgcc | aaagatgaat | cattttttngg | cgttaatgan | 1500 |
| gtatctntt | ctannntcag | ggcaagtctt | ntnccgttat | atcgtnggng | tctgagaatg | 1560 |
| gagctgnttc | acaangannc | ccctcnacat | ctcngntggt | atancntgaa | aattcggttt | 1620 |
| ggaataagnc | ggaagtntgt | ggatcatgta | ggtcgnccaa | agatgaatat | tgtngtngac | 1680 |
| atacntcctg | atttatgcaa | gatcttggac | gcatnnnatg | ctnctgcgca | taacttactg | 1740 |
| attgactcaa | gcacaanntc | agannggagg | cctacngtta | tgangaaana | aggctttgnc | 1800 |
| aactatccca | cngccngact | gcagtaagta | tncancactc | tctctgncct | tttacatacn | 1860 |
| agcatnaatc | nacnggagag | tctctaaanac | catctccaac | nctactcnnt | nttcaccncc | 1920 |
| aaantcatatt | ttggagttaa | atcccnccaa | nncttgcaaa | atannnatct | tcaaanntt | 1980 |
| tctccatatt | tggagattnt | ganttttnaa | gtcatgactn | cattttggag | ttgggtngga | 2040 | gaaaaacaca antccaaaat aganttactt cattttggng taaaaaantg angaaatggg    2100 ttngagatnn nctaacctcn ntnancantc ntntnttgtt ggnagaataa gctcngaatc    2160 caatngaacc cnggtanacc aaaaagaagn acctttggga accaatcaaa agctcgattt    2220 cagtagcgat aattttgaaa agctngagtc agcactnntt ccnggtnccc tggttgannn    2280 nttcttctca nncgannctt acgattatan gaaaatggta gggatacgtc tagcagccag    2340 aaagttggta atccanctga agaaatgatc tagccaagga aaaatcattc cnctgtctct    2400 tnctgntnag tcggngngna nnn                                           2423

```
<210> SEQ ID NO 23
<211> LENGTH: 1521
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
```

```
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (374)..(375)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
```

```
<222> LOCATION: (381)..(381)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (408)..(410)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (528)..(529)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
```

-continued

```
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
```

-continued

```
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (989)..(991)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1021)..(1021)
```

-continued

```
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1053)..(1054)
<223> OTHER INFORMATION: n is a, c, g, or t
<220> FEATURE:
<221> NAME/KEY: misc_feature
<222> LOCATION: (1061)..(1061)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
<222> LOCATION: (1081)..(1081)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1112)..(1112)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1190)..(1192)
<223> OTHER INFORMATION: n is a, c, g, or t
<220> FEATURE:
<221> NAME/KEY: misc_feature
<222> LOCATION: (1198)..(1198)
<223> OTHER INFORMATION: n is a, c, g, or t
<220> FEATURE:
<221> NAME/KEY: misc_feature
<222> LOCATION: (1232)..(1233)
<223> OTHER INFORMATION: n is a, c, g, or t
<220> FEATURE:
<221> NAME/KEY: misc_feature
<222> LOCATION: (1239)..(1240)
<223> OTHER INFORMATION: n is a, c, g, or t
<220> FEATURE:
<221> NAME/KEY: misc_feature
```

-continued

```
<222> LOCATION: (1251)..(1251)
<223> OTHER INFORMATION: n is a, c, g, or t
<220> FEATURE:
<221> NAME/KEY: misc_feature
<222> LOCATION: (1259)..(1259)
<223> OTHER INFORMATION: n is a, c, g, or t
<220> FEATURE:
<221> NAME/KEY: misc_feature
<222> LOCATION: (1264)..(1264)
<223> OTHER INFORMATION: n is a, c, g, or t
<220> FEATURE:
<221> NAME/KEY: misc_feature
<222> LOCATION: (1274)..(1274)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1291)..(1291)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1325)..(1325)
<223> OTHER INFORMATION: n is a, c, g, or t
<220> FEATURE:
<221> NAME/KEY: misc_feature
<222> LOCATION: (1330)..(1330)
<223> OTHER INFORMATION: n is a, c, g, or t
<220> FEATURE:
<221> NAME/KEY: misc_feature
<222> LOCATION: (1343)..(1343)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1410)..(1411)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1420)..(1420)
<223> OTHER INFORMATION: n is a, c, g, or t
<220> FEATURE:
<221> NAME/KEY: misc_feature
<222> LOCATION: (1431)..(1434)
<223> OTHER INFORMATION: n is a, c, g, or t
<220> FEATURE:
<221> NAME/KEY: misc_feature
<222> LOCATION: (1444)..(1445)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
<220> FEATURE:
<221> NAME/KEY: misc_feature
<222> LOCATION: (1463)..(1463)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
```

<400> SEQUENCE: 23

```
atggcttcga ctctgggcng cgatgngagn nncgagatag tgtttttcga tcttgagacn      60
gcngttncga ccnaatcggg ncanccntnt gcgattttgg agtttggngc tatcttagtt     120
tgccctatga agctagngga gctctatagt tacnccacnt tggntcgacc nacnganctt     180
tcnctcatct ncacgctcac gaagcgacga agcggcatta cgcgcgacgg agttctctct     240
gcacctacnt tctctgaaat cgctgatgaa ntctacgana ttcnccncgg acgaatttgg     300
gnnggacata acataaagag attcgattgt gtaagantan gagatgcatt tgcagnaatt     360
ggtntcnctc cccnngagnc naaagntnca attgatncac tttcgttnnn gtctcagaag     420
tttgggaagn gagctggnga cntgaagatg gcntngcntg ctacntattt cgngctagga     480
gancangctc acaggagctt agatgatgtc cggatgaatc ttgaagtnnt caagnactgt     540
ncaaccntct tntttctgga gtcnagtgtn ccngacattc ttananncat nagctggttn     600
tnccnaagaa aaagtcngng aacacgaagt aatgagaagt cactgccnna tggagtcaga     660
gaaagcccna cttcttcctc ttcnagccct naanctganc cgagttcgtc ttctgtanan     720
gcnacanctg tcaaaaacca tcccatcatt tctcttctga cggaatgctc agnaanngat     780
acatctagtt gngaaataga tccatcngac ataaccactc taataagtaa actacatatt     840
ggaactctta aganagatgc tgcggacgaa gccaaaactg tgagagangc ngcgnangaa     900
gccaanantg taagacagca nggtgaatca accgatccca atgccaaaga tgaatcattt     960
ttnggcgtta atgangtatc tntttctann ntcagggcaa gtcttntncc gttatatcgt    1020
ngggntctga gaatggagct gnttcacaan ganncccctc nacatctcng ntggtatanc    1080
ntgaaaattc ggtttggaat aagncggaag tntgtggatc atgtaggtcg nccaaagatg    1140
aatattgtng tngacatacn tcctgattta tgcaagatct tggacgcatn nnatgctnct    1200
gcgcataact tactgattga ctcaagcaca anntcagann ggaggcctac ngttatgang    1260
aaanaaggct ttgncaacta tcccacngcc ngactgcaaa taagctcnga atccaatnga    1320
acccnggtan accaaaaaga agnaccttg ggaaccaatc aaaagctcga tttcagtagc    1380
gataattttg aaaagctnga gtcagcactn nttccnggtn ccctggttga nnnnttcttc    1440
tcanncgann cttacgatta tangaaaatg gtagggatac gtctagcagc cagaaagttg    1500
gtaatccanc tgaagaaatg a                                              1521
```

<210> SEQ ID NO 24
<211> LENGTH: 2393
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t -continued

```
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
```

-continued

```
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (303)..(304)
<223> OTHER INFORMATION: n is a, c, g, or t
<220> FEATURE:
<221> NAME/KEY: misc_feature
<222> LOCATION: (312)..(317)
<223> OTHER INFORMATION: n is a, c, g, or t
<220> FEATURE:
<221> NAME/KEY: misc_feature
<222> LOCATION: (320)..(321)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (325)..(326)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (385)..(386)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (457)..(458)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
```

```
<222> LOCATION: (469)..(469)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (491)..(493)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (658)..(662)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
```

-continued

```
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (726)..(727)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (794)..(794)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (857)..(857)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
```

-continued

```
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (934)..(934)
<223> OTHER INFORMATION: n is a, c, g, or t
<220> FEATURE:
<221> NAME/KEY: misc_feature
<222> LOCATION: (939)..(940)
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t
<220> FEATURE:
<221> NAME/KEY: misc_feature
<222> LOCATION: (976)..(977)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (1003)..(1003)
```

```
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1049)..(1050)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1109)..(1109)
<223> OTHER INFORMATION: n is a, c, g, or t
<220> FEATURE:
<221> NAME/KEY: misc_feature
<222> LOCATION: (1111)..(1112)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1127)..(1127)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1142)..(1142)
<223> OTHER INFORMATION: n is a, c, g, or t
<220> FEATURE:
<221> NAME/KEY: misc_feature
<222> LOCATION: (1144)..(1144)
<223> OTHER INFORMATION: n is a, c, g, or t
<220> FEATURE:
<221> NAME/KEY: misc_feature
<222> LOCATION: (1173)..(1174)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1216)..(1216)
<223> OTHER INFORMATION: n is a, c, g, or t
<220> FEATURE:
<221> NAME/KEY: misc_feature
<222> LOCATION: (1219)..(1219)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
```

-continued

```
<222> LOCATION: (1243)..(1243)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1252)..(1252)
<223> OTHER INFORMATION: n is a, c, g, or t
<220> FEATURE:
<221> NAME/KEY: misc_feature
<222> LOCATION: (1298)..(1298)
<223> OTHER INFORMATION: n is a, c, g, or t
<220> FEATURE:
<221> NAME/KEY: misc_feature
<222> LOCATION: (1301)..(1302)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1379)..(1379)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1390)..(1390)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t
<220> FEATURE:
<221> NAME/KEY: misc_feature
<222> LOCATION: (1401)..(1401)
<223> OTHER INFORMATION: n is a, c, g, or t
<220> FEATURE:
<221> NAME/KEY: misc_feature
<222> LOCATION: (1403)..(1403)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t
<220> FEATURE:
<221> NAME/KEY: misc_feature
<222> LOCATION: (1470)..(1470)
<223> OTHER INFORMATION: n is a, c, g, or t
<220> FEATURE:
<221> NAME/KEY: misc_feature
<222> LOCATION: (1477)..(1477)
<223> OTHER INFORMATION: n is a, c, g, or t
<220> FEATURE:
<221> NAME/KEY: misc_feature
<222> LOCATION: (1484)..(1486)
<223> OTHER INFORMATION: n is a, c, g, or t
<220> FEATURE:
```

-continued

```
<221> NAME/KEY: misc_feature
<222> LOCATION: (1501)..(1501)
<223> OTHER INFORMATION: n is a, c, g, or t
<220> FEATURE:
<221> NAME/KEY: misc_feature
<222> LOCATION: (1503)..(1503)
<223> OTHER INFORMATION: n is a, c, g, or t
<220> FEATURE:
<221> NAME/KEY: misc_feature
<222> LOCATION: (1516)..(1516)
<223> OTHER INFORMATION: n is a, c, g, or t
<220> FEATURE:
<221> NAME/KEY: misc_feature
<222> LOCATION: (1519)..(1519)
<223> OTHER INFORMATION: n is a, c, g, or t
<220> FEATURE:
<221> NAME/KEY: misc_feature
<222> LOCATION: (1537)..(1537)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1548)..(1549)
<223> OTHER INFORMATION: n is a, c, g, or t
<220> FEATURE:
<221> NAME/KEY: misc_feature
<222> LOCATION: (1556)..(1556)
<223> OTHER INFORMATION: n is a, c, g, or t
<220> FEATURE:
<221> NAME/KEY: misc_feature
<222> LOCATION: (1564)..(1564)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1574)..(1574)
<223> OTHER INFORMATION: n is a, c, g, or t
<220> FEATURE:
<221> NAME/KEY: misc_feature
<222> LOCATION: (1576)..(1576)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1607)..(1607)
<223> OTHER INFORMATION: n is a, c, g, or t
<220> FEATURE:
<221> NAME/KEY: misc_feature
<222> LOCATION: (1626)..(1626)
<223> OTHER INFORMATION: n is a, c, g, or t
<220> FEATURE:
<221> NAME/KEY: misc_feature
<222> LOCATION: (1644)..(1644)
<223> OTHER INFORMATION: n is a, c, g, or t
<220> FEATURE:
<221> NAME/KEY: misc_feature
<222> LOCATION: (1647)..(1647)
<223> OTHER INFORMATION: n is a, c, g, or t
<220> FEATURE:
<221> NAME/KEY: misc_feature
<222> LOCATION: (1655)..(1655)
<223> OTHER INFORMATION: n is a, c, g, or t
<220> FEATURE:
<221> NAME/KEY: misc_feature
<222> LOCATION: (1685)..(1687)
<223> OTHER INFORMATION: n is a, c, g, or t
<220> FEATURE:
<221> NAME/KEY: misc_feature
<222> LOCATION: (1693)..(1693)
<223> OTHER INFORMATION: n is a, c, g, or t
```

-continued

```
<220> FEATURE:
<221> NAME/KEY: misc_feature
<222> LOCATION: (1727)..(1728)
<223> OTHER INFORMATION: n is a, c, g, or t
<220> FEATURE:
<221> NAME/KEY: misc_feature
<222> LOCATION: (1734)..(1735)
<223> OTHER INFORMATION: n is a, c, g, or t
<220> FEATURE:
<221> NAME/KEY: misc_feature
<222> LOCATION: (1746)..(1746)
<223> OTHER INFORMATION: n is a, c, g, or t
<220> FEATURE:
<221> NAME/KEY: misc_feature
<222> LOCATION: (1754)..(1754)
<223> OTHER INFORMATION: n is a, c, g, or t
<220> FEATURE:
<221> NAME/KEY: misc_feature
<222> LOCATION: (1759)..(1759)
<223> OTHER INFORMATION: n is a, c, g, or t
<220> FEATURE:
<221> NAME/KEY: misc_feature
<222> LOCATION: (1769)..(1769)
<223> OTHER INFORMATION: n is a, c, g, or t
<220> FEATURE:
<221> NAME/KEY: misc_feature
<222> LOCATION: (1782)..(1782)
<223> OTHER INFORMATION: n is a, c, g, or t
<220> FEATURE:
<221> NAME/KEY: misc_feature
<222> LOCATION: (1786)..(1786)
<223> OTHER INFORMATION: n is a, c, g, or t
<220> FEATURE:
<221> NAME/KEY: misc_feature
<222> LOCATION: (1802)..(1802)
<223> OTHER INFORMATION: n is a, c, g, or t
<220> FEATURE:
<221> NAME/KEY: misc_feature
<222> LOCATION: (1805)..(1805)
<223> OTHER INFORMATION: n is a, c, g, or t
<220> FEATURE:
<221> NAME/KEY: misc_feature
<222> LOCATION: (1817)..(1817)
<223> OTHER INFORMATION: n is a, c, g, or t
<220> FEATURE:
<221> NAME/KEY: misc_feature
<222> LOCATION: (1830)..(1830)
<223> OTHER INFORMATION: n is a, c, g, or t
<220> FEATURE:
<221> NAME/KEY: misc_feature
<222> LOCATION: (1836)..(1836)
<223> OTHER INFORMATION: n is a, c, g, or t
<220> FEATURE:
<221> NAME/KEY: misc_feature
<222> LOCATION: (1841)..(1841)
<223> OTHER INFORMATION: n is a, c, g, or t
<220> FEATURE:
<221> NAME/KEY: misc_feature
<222> LOCATION: (1844)..(1844)
<223> OTHER INFORMATION: n is a, c, g, or t
<220> FEATURE:
<221> NAME/KEY: misc_feature
<222> LOCATION: (1858)..(1858)
<223> OTHER INFORMATION: n is a, c, g, or t
<220> FEATURE:
<221> NAME/KEY: misc_feature
<222> LOCATION: (1871)..(1871)
<223> OTHER INFORMATION: n is a, c, g, or t
<220> FEATURE:
<221> NAME/KEY: misc_feature
<222> LOCATION: (1878)..(1879)
<223> OTHER INFORMATION: n is a, c, g, or t
<220> FEATURE:
<221> NAME/KEY: misc_feature
<222> LOCATION: (1881)..(1881)
<223> OTHER INFORMATION: n is a, c, g, or t
<220> FEATURE:
<221> NAME/KEY: misc_feature
<222> LOCATION: (1888)..(1888)
```

-continued

```
<223> OTHER INFORMATION: n is a, c, g, or t
<220> FEATURE:
<221> NAME/KEY: misc_feature
<222> LOCATION: (1894)..(1894)
<223> OTHER INFORMATION: n is a, c, g, or t
<220> FEATURE:
<221> NAME/KEY: misc_feature
<222> LOCATION: (1916)..(1916)
<223> OTHER INFORMATION: n is a, c, g, or t
<220> FEATURE:
<221> NAME/KEY: misc_feature
<222> LOCATION: (1921)..(1922)
<223> OTHER INFORMATION: n is a, c, g, or t
<220> FEATURE:
<221> NAME/KEY: misc_feature
<222> LOCATION: (1934)..(1936)
<223> OTHER INFORMATION: n is a, c, g, or t
<220> FEATURE:
<221> NAME/KEY: misc_feature
<222> LOCATION: (1946)..(1947)
<223> OTHER INFORMATION: n is a, c, g, or t
<220> FEATURE:
<221> NAME/KEY: misc_feature
<222> LOCATION: (1969)..(1969)
<223> OTHER INFORMATION: n is a, c, g, or t
<220> FEATURE:
<221> NAME/KEY: misc_feature
<222> LOCATION: (1973)..(1973)
<223> OTHER INFORMATION: n is a, c, g, or t
<220> FEATURE:
<221> NAME/KEY: misc_feature
<222> LOCATION: (1978)..(1978)
<223> OTHER INFORMATION: n is a, c, g, or t
<220> FEATURE:
<221> NAME/KEY: misc_feature
<222> LOCATION: (1990)..(1990)
<223> OTHER INFORMATION: n is a, c, g, or t
<220> FEATURE:
<221> NAME/KEY: misc_feature
<222> LOCATION: (2007)..(2007)
<223> OTHER INFORMATION: n is a, c, g, or t
<220> FEATURE:
<221> NAME/KEY: misc_feature
<222> LOCATION: (2022)..(2022)
<223> OTHER INFORMATION: n is a, c, g, or t
<220> FEATURE:
<221> NAME/KEY: misc_feature
<222> LOCATION: (2034)..(2034)
<223> OTHER INFORMATION: n is a, c, g, or t
<220> FEATURE:
<221> NAME/KEY: misc_feature
<222> LOCATION: (2049)..(2049)
<223> OTHER INFORMATION: n is a, c, g, or t
<220> FEATURE:
<221> NAME/KEY: misc_feature
<222> LOCATION: (2058)..(2058)
<223> OTHER INFORMATION: n is a, c, g, or t
<220> FEATURE:
<221> NAME/KEY: misc_feature
<222> LOCATION: (2062)..(2062)
<223> OTHER INFORMATION: n is a, c, g, or t
<220> FEATURE:
<221> NAME/KEY: misc_feature
<222> LOCATION: (2073)..(2073)
<223> OTHER INFORMATION: n is a, c, g, or t
<220> FEATURE:
<221> NAME/KEY: misc_feature
<222> LOCATION: (2079)..(2081)
<223> OTHER INFORMATION: n is a, c, g, or t
<220> FEATURE:
<221> NAME/KEY: misc_feature
<222> LOCATION: (2090)..(2091)
<223> OTHER INFORMATION: n is a, c, g, or t
<220> FEATURE:
<221> NAME/KEY: misc_feature
<222> LOCATION: (2093)..(2093)
<223> OTHER INFORMATION: n is a, c, g, or t
<220> FEATURE:
<221> NAME/KEY: misc_feature
```

-continued

```
<222> LOCATION: (2095)..(2095)
<223> OTHER INFORMATION: n is a, c, g, or t
<220> FEATURE:
<221> NAME/KEY: misc_feature
<222> LOCATION: (2098)..(2098)
<223> OTHER INFORMATION: n is a, c, g, or t
<220> FEATURE:
<221> NAME/KEY: misc_feature
<222> LOCATION: (2101)..(2101)
<223> OTHER INFORMATION: n is a, c, g, or t
<220> FEATURE:
<221> NAME/KEY: misc_feature
<222> LOCATION: (2103)..(2103)
<223> OTHER INFORMATION: n is a, c, g, or t
<220> FEATURE:
<221> NAME/KEY: misc_feature
<222> LOCATION: (2105)..(2105)
<223> OTHER INFORMATION: n is a, c, g, or t
<220> FEATURE:
<221> NAME/KEY: misc_feature
<222> LOCATION: (2113)..(2113)
<223> OTHER INFORMATION: n is a, c, g, or t
<220> FEATURE:
<221> NAME/KEY: misc_feature
<222> LOCATION: (2125)..(2125)
<223> OTHER INFORMATION: n is a, c, g, or t
<220> FEATURE:
<221> NAME/KEY: misc_feature
<222> LOCATION: (2135)..(2135)
<223> OTHER INFORMATION: n is a, c, g, or t
<220> FEATURE:
<221> NAME/KEY: misc_feature
<222> LOCATION: (2142)..(2142)
<223> OTHER INFORMATION: n is a, c, g, or t
<220> FEATURE:
<221> NAME/KEY: misc_feature
<222> LOCATION: (2147)..(2147)
<223> OTHER INFORMATION: n is a, c, g, or t
<220> FEATURE:
<221> NAME/KEY: misc_feature
<222> LOCATION: (2160)..(2160)
<223> OTHER INFORMATION: n is a, c, g, or t
<220> FEATURE:
<221> NAME/KEY: misc_feature
<222> LOCATION: (2215)..(2215)
<223> OTHER INFORMATION: n is a, c, g, or t
<220> FEATURE:
<221> NAME/KEY: misc_feature
<222> LOCATION: (2227)..(2228)
<223> OTHER INFORMATION: n is a, c, g, or t
<220> FEATURE:
<221> NAME/KEY: misc_feature
<222> LOCATION: (2233)..(2233)
<223> OTHER INFORMATION: n is a, c, g, or t
<220> FEATURE:
<221> NAME/KEY: misc_feature
<222> LOCATION: (2237)..(2237)
<223> OTHER INFORMATION: n is a, c, g, or t
<220> FEATURE:
<221> NAME/KEY: misc_feature
<222> LOCATION: (2248)..(2251)
<223> OTHER INFORMATION: n is a, c, g, or t
<220> FEATURE:
<221> NAME/KEY: misc_feature
<222> LOCATION: (2261)..(2262)
<223> OTHER INFORMATION: n is a, c, g, or t
<220> FEATURE:
<221> NAME/KEY: misc_feature
<222> LOCATION: (2266)..(2267)
<223> OTHER INFORMATION: n is a, c, g, or t
<220> FEATURE:
<221> NAME/KEY: misc_feature
<222> LOCATION: (2280)..(2280)
<223> OTHER INFORMATION: n is a, c, g, or t
<220> FEATURE:
<221> NAME/KEY: misc_feature
<222> LOCATION: (2326)..(2326)
<223> OTHER INFORMATION: n is a, c, g, or t
<220> FEATURE:
```

```
<221> NAME/KEY: misc_feature
<222> LOCATION: (2362)..(2362)
<223> OTHER INFORMATION: n is a, c, g, or t
<220> FEATURE:
<221> NAME/KEY: misc_feature
<222> LOCATION: (2372)..(2372)
<223> OTHER INFORMATION: n is a, c, g, or t
<220> FEATURE:
<221> NAME/KEY: misc_feature
<222> LOCATION: (2376)..(2376)
<223> OTHER INFORMATION: n is a, c, g, or t
<220> FEATURE:
<221> NAME/KEY: misc_feature
<222> LOCATION: (2378)..(2378)
<223> OTHER INFORMATION: n is a, c, g, or t
<220> FEATURE:
<221> NAME/KEY: misc_feature
<222> LOCATION: (2385)..(2385)
<223> OTHER INFORMATION: n is a, c, g, or t
<220> FEATURE:
<221> NAME/KEY: misc_feature
<222> LOCATION: (2387)..(2387)
<223> OTHER INFORMATION: n is a, c, g, or t
<220> FEATURE:
<221> NAME/KEY: misc_feature
<222> LOCATION: (2389)..(2389)
<223> OTHER INFORMATION: n is a, c, g, or t
<220> FEATURE:
<221> NAME/KEY: misc_feature
<222> LOCATION: (2391)..(2393)
<223> OTHER INFORMATION: n is a, c, g, or t

<400> SEQUENCE: 24
atggcttcga ctctgggcng cgatgngagn nncgagatag tgtttttcga tcttgagacn     60
gcngttncga ccnaatcggg ncancentnt gcgattttgg agtttggngc tatcttagtt    120
tgccctatga agctagngga gctctatagt tacnccacnt tggntcgacc nacngancett   180 tcnctcatct ncacgctcac gaagcgacga agcggcatta cgcgcgacgg agttctctct    240
gcacctacnt tctctgaaat cgctgatgaa ntctacgana ttcncncgg taagggtttc     300 tcnttttttt tnnnnnnctn ncncnntctc tctnacncga agntanaagt attgattttg    360
gtgtttctgt aggacgaatt tgggnnggac ataacataaa gagattcgat tgtgtaagan    420
tangagatgc atttgcagna attggtntcn ctccccnnga gncnaaagnt ncaattgatn    480
cactttcgtt nnngtctcag aagtttggga agngagctgg ngacntgaag gtctctcttt    540
tttcgtcttc ncgatgataa atctcaaagc cnatagcttn cttgttatcn ttatagatat    600
gaatttcnan gtaacttcan agattcatca ctcatcanag tngctaaaat ttacnctnnn    660
nnaanaangt agatggcntn gcntgctacn tatttcgngc taggaganca ngctcacagg    720
tnaaannagt aaacgatacn ntgtgcctttt taacgattcn ccagttgtnt caatatggga    780
ctaaacatgg ntangattca ncaggagctt agatgatgtc cggatgaatc ttgaagtnnt    840
caagnactgt ncaaccntct tntttctggt attgntgtct tntcatttct tgaataatga    900
tnaactcnta anttnaaaag gantagatta nagnggttnn gacatatctg anttctgtct    960
ncngttntgn aaaagnnggn tcnatcttcc ttncagacca canctttgca agccgtaaac   1020
atggnttgca acttgcaagt atagtttgnn atatcactga gtttaagtac ttggtgttttg   1080 caggagtcna gtgtnccnga cattcttana nncatnagct ggttntnccn aagaaaaagt   1140
cngngaacac gaagtaatga gaagtcactg ccnnatggag tcagagaaag cccnacttct   1200
tcctcttcna gccctnaanc tganccgagt tcgtcttctg tanangcnac anctgtcaaa   1260
aaccatccca tcatttctct tctgacggaa tgctcagnaa nngatacatc tagttgngaa   1320
atagatccat cngacataac cactctaata agtaaactac atattggaac tcttaagana   1380
```

```
gangcngcgn angaagccaa nantgtaaga cagcanggtg aatcaaccga tcccaatgcc    1440
aaagatgaat cattttttngg cgttaatgan gtatctnttt ctannntcag ggcaagtctt    1500
ntnccgttat atcgtnggng tctgagaatg gagctgnttc acaangannc ccctcnacat    1560
ctcngntggt atancntgaa aattcggttt ggaataagnc ggaagtntgt ggatcatgta    1620
ggtcgnccaa agatgaatat tgtngtngac atacntcctg atttatgcaa gatcttggac    1680
gcatnnnatg ctnctgcgca taacttactg attgactcaa gcacaanntc aganngagg     1740 cctacngtta tgangaaana aggctttgnc aactatccca cngccngact gcagtaagta    1800
tncancactc tctctgncct tttacatacn agcatnaatc nacnggagag tctctaanac    1860
catctccaac nctactcnnt nttcaccncc aaantctatt ttggagttaa atcccnccaa    1920
nncttgcaaa atannnatct tcaaannttt tctccatatt tggagattnt ganttttnaa    1980
gtcatgactn cattttggag ttgggtngga gaaaaacaca antccaaaat aganttactt    2040
cattttggng taaaaaantg angaaatggg ttngagatnn nctaacctcn ntnancantc    2100
ntntnttgtt ggnagaataa gctcngaatc caatngaacc cnggtanacc aaaaagaagn    2160
acctttggga accaatcaaa agctcgattt cagtagcgat aattttgaaa agctngagtc    2220
agcactnntt ccnggtnccc tggttgannn nttcttctca nncganncctt acgattatan    2280 gaaaatggta gggatacgtc tagcagccag aaagttggta atccanctga agaaatgatc    2340
tagccaagga aaaatcattc cnctgtctct tnctgntnag tcggngngna nnn           2393

<210> SEQ ID NO 25
<211> LENGTH: 1491
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
```

```
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
```

```
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (374)..(375)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (408)..(410)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
```

-continued

```
<221> NAME/KEY: misc_feature
<222> LOCATION: (528)..(529)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
```

-continued

```
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (945)..(945)
```

-continued

```
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (959)..(961)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1024)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1049)..(1049)
<223> OTHER INFORMATION: n is a, c, g, or t
<220> FEATURE:
<221> NAME/KEY: misc_feature
<222> LOCATION: (1051)..(1051)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1082)..(1082)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
```

```
<222> LOCATION: (1130)..(1130)
<223> OTHER INFORMATION: n is a, c, g, or t
<220> FEATURE:
<221> NAME/KEY: misc_feature
<222> LOCATION: (1160)..(1162)
<223> OTHER INFORMATION: n is a, c, g, or t
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (1202)..(1203)
<223> OTHER INFORMATION: n is a, c, g, or t
<220> FEATURE:
<221> NAME/KEY: misc_feature
<222> LOCATION: (1209)..(1210)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1234)..(1234)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t
<220> FEATURE:
<221> NAME/KEY: misc_feature
<222> LOCATION: (1313)..(1313)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1380)..(1381)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1390)..(1390)
<223> OTHER INFORMATION: n is a, c, g, or t
<220> FEATURE:
```

```
<221> NAME/KEY: misc_feature
<222> LOCATION: (1401)..(1404)
<223> OTHER INFORMATION: n is a, c, g, or t
<220> FEATURE:
<221> NAME/KEY: misc_feature
<222> LOCATION: (1414)..(1415)
<223> OTHER INFORMATION: n is a, c, g, or t
<220> FEATURE:
<221> NAME/KEY: misc_feature
<222> LOCATION: (1419)..(1420)
<223> OTHER INFORMATION: n is a, c, g, or t
<220> FEATURE:
<221> NAME/KEY: misc_feature
<222> LOCATION: (1433)..(1433)
<223> OTHER INFORMATION: n is a, c, g, or t
<220> FEATURE:
<221> NAME/KEY: misc_feature
<222> LOCATION: (1479)..(1479)
<223> OTHER INFORMATION: n is a, c, g, or t

<400> SEQUENCE: 25
atggcttcga ctctgggcng cgatgngagn nncgagatag tgtttttcga tcttgagacn     60
gcngttncga ccnaatcggg ncanccntnt gcgattttgg agtttggngc tatcttagtt    120
tgccctatga agctagngga gctctatagt tacnccacnt tggntcgacc nacngancctt   180
tcnctcatct ncacgctcac gaagcgacga agcggcatta cgcgcgacgg agttctctct   240
gcacctacnt tctctgaaat cgctgatgaa ntctacgana ttcnccncgg acgaatttgg   300
gnnggacata acataaagag attcgattgt gtaagantan gagatgcatt tgcagnaatt   360
ggtntcnctc cccnngagnc naaagntnca attgatncac tttcgttnnn gtctcagaag   420
tttgggaagn gagctggnga cntgaagatg gcntngcntg ctacntattt cgngctagga   480
gancangctc acaggagctt agatgatgtc cggatgaatc ttgaagtnnt caagnactgt   540
ncaaccntct tntttctgga gtcnagtgtn ccngacattc ttananncat nagctggttn   600
tnccnaagaa aaagtcngng aacacgaagt aatgagaagt cactgccnna tggagtcaga   660
gaaagcccna cttcttcctc ttcnagcccct naanctganc cgagttcgtc ttctgtanan   720
gcnacanctg tcaaaaacca tcccatcatt tctcttctga cggaatgctc agnaanngat   780
acatctagtt gngaaatgga tccatcngac ataaccactc taataagtaa actacatatt   840
ggaactctta aganagangc ngcgnangaa gccaanantg taagacagca nggtgaatca   900
accgatccca atgccaaaga tgaatcattt ttnggcgtta atgangtatc tntttctann   960
ntcagggcaa gtcttntncc gttatatcgt nggngtctga gaatggagct gnttcacaan  1020
gannccctc nacatctcng ntggtatanc ntgaaaattc ggtttggaat aagncggaag   1080
tntgtggatc atgtaggtcg nccaaagatg aatattgtng tngacatacn tcctgattta   1140
tgcaagatct tggacgcatn nnatgctnct gcgcataact tactgattga ctcaagcaca   1200
anntcagann ggaggcctac ngttatgang aaanaaggct ttgncaacta tcccacngcc   1260
ngactgcaaa taagctcnga atccaatnga acccnggtan accaaaaaga agnacctttg   1320
ggaaccaatc aaaagctcga tttcagtagc gataattttg aaaagctnga gtcagcactn   1380
nttccnggtn ccctggttga nnnnttcttc tcannccgann cttacgatta tangaaaatg   1440
gtagggatac gtctagcagc cagaaagttg gtaatccanc tgaagaaatg a             1491

<210> SEQ ID NO 26
<211> LENGTH: 495
<212> TYPE: DNA
<213> ORGANISM: Boechera
<220> FEATURE:
<221> NAME/KEY: misc_feature
```

```
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
```

-continued

```
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (263)..(264)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (335)..(336)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (369)..(371)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
```

```
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (489)..(490)
<223> OTHER INFORMATION: n is a, c, g, or t

<400> SEQUENCE: 26
gtgtttttcg atcttgagac ngcngttncg accnaatcgg gncanccntn tgcgattttg      60
gagtttggng ctatcttagt ttgccctatg aagctagngg agctctatag ttacnccacn    120
ttggntcgac cnacnganct ttcnctcatc tncacgctca cgaagcgacg aagcggcatt    180
acgcgcgacg gagttctctc tgcacctacn ttctctgaaa tcgctgatga antctacgan    240
attcnccncg gacgaatttg ggnnggacat aacataaaga gattcgattg tgtaaganta    300
ngagatgcat ttgcagnaat tggtntcnct ccccnngagn cnaaagntnc aattgatnca    360
ctttcgttnn ngtctcagaa gtttgggaag ngagctggng acntgaagat ggcntngcnt    420
gctacntatt tcgngctagg agancangct cacaggagct tagatgatgt ccggatgaat    480
cttgaagtnn tcaag                                                     495

<210> SEQ ID NO 27
<211> LENGTH: 2536
<212> TYPE: DNA
<213> ORGANISM: Boechera
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
```

```
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (427)..(432)
<223> OTHER INFORMATION: n is a, c, g, or t
<220> FEATURE:
<221> NAME/KEY: misc_feature
<222> LOCATION: (435)..(436)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (500)..(501)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (773)..(777)
<223> OTHER INFORMATION: n is a, c, g, or t
```

-continued

```
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1045)..(1045)
```

```
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1054)..(1054)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1106)..(1106)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
<220> FEATURE:
<221> NAME/KEY: misc_feature
<222> LOCATION: (1140)..(1145)
<223> OTHER INFORMATION: n is a, c, g, or t
<220> FEATURE:
<221> NAME/KEY: misc_feature
<222> LOCATION: (1163)..(1163)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1211)..(1211)
<223> OTHER INFORMATION: n is a, c, g, or t
<220> FEATURE:
<221> NAME/KEY: misc_feature
<222> LOCATION: (1222)..(1222)
<223> OTHER INFORMATION: n is a, c, g, or t
<220> FEATURE:
<221> NAME/KEY: misc_feature
<222> LOCATION: (1224)..(1225)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1240)..(1240)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
```

```
<222> LOCATION: (1322)..(1322)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1337)..(1337)
<223> OTHER INFORMATION: n is a, c, g, or t
<220> FEATURE:
<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1411)..(1411)
<223> OTHER INFORMATION: n is a, c, g, or t
<220> FEATURE:
<221> NAME/KEY: misc_feature
<222> LOCATION: (1415)..(1415)
<223> OTHER INFORMATION: n is a, c, g, or t
<220> FEATURE:
<221> NAME/KEY: misc_feature
<222> LOCATION: (1492)..(1492)
<223> OTHER INFORMATION: n is a, c, g, or t
<220> FEATURE:
<221> NAME/KEY: misc_feature
<222> LOCATION: (1529)..(1529)
<223> OTHER INFORMATION: n is a, c, g, or t
<220> FEATURE:
<221> NAME/KEY: misc_feature
<222> LOCATION: (1535)..(1535)
<223> OTHER INFORMATION: n is a, c, g, or t
<220> FEATURE:
<221> NAME/KEY: misc_feature
<222> LOCATION: (1544)..(1544)
<223> OTHER INFORMATION: n is a, c, g, or t
<220> FEATURE:
<221> NAME/KEY: misc_feature
<222> LOCATION: (1546)..(1546)
<223> OTHER INFORMATION: n is a, c, g, or t
<220> FEATURE:
<221> NAME/KEY: misc_feature
<222> LOCATION: (1627)..(1627)
<223> OTHER INFORMATION: n is a, c, g, or t
<220> FEATURE:
<221> NAME/KEY: misc_feature
<222> LOCATION: (1659)..(1659)
<223> OTHER INFORMATION: n is a, c, g, or t
<220> FEATURE:
<221> NAME/KEY: misc_feature
<222> LOCATION: (1662)..(1662)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1688)..(1688)
<223> OTHER INFORMATION: n is a, c, g, or t
<220> FEATURE:
<221> NAME/KEY: misc_feature
<222> LOCATION: (1692)..(1692)
<223> OTHER INFORMATION: n is a, c, g, or t
<220> FEATURE:
<221> NAME/KEY: misc_feature
<222> LOCATION: (1699)..(1699)
<223> OTHER INFORMATION: n is a, c, g, or t
<220> FEATURE:
<221> NAME/KEY: misc_feature
<222> LOCATION: (1709)..(1709)
<223> OTHER INFORMATION: n is a, c, g, or t
<220> FEATURE:
<221> NAME/KEY: misc_feature
<222> LOCATION: (1798)..(1798)
<223> OTHER INFORMATION: n is a, c, g, or t
<220> FEATURE:
```

-continued

```
<221> NAME/KEY: misc_feature
<222> LOCATION: (1828)..(1828)
<223> OTHER INFORMATION: n is a, c, g, or t
<220> FEATURE:
<221> NAME/KEY: misc_feature
<222> LOCATION: (1870)..(1871)
<223> OTHER INFORMATION: n is a, c, g, or t
<220> FEATURE:
<221> NAME/KEY: misc_feature
<222> LOCATION: (1878)..(1878)
<223> OTHER INFORMATION: n is a, c, g, or t
<220> FEATURE:
<221> NAME/KEY: misc_feature
<222> LOCATION: (1889)..(1889)
<223> OTHER INFORMATION: n is a, c, g, or t
<220> FEATURE:
<221> NAME/KEY: misc_feature
<222> LOCATION: (1897)..(1897)
<223> OTHER INFORMATION: n is a, c, g, or t
<220> FEATURE:
<221> NAME/KEY: misc_feature
<222> LOCATION: (1902)..(1902)
<223> OTHER INFORMATION: n is a, c, g, or t
<220> FEATURE:
<221> NAME/KEY: misc_feature
<222> LOCATION: (1912)..(1912)
<223> OTHER INFORMATION: n is a, c, g, or t
<220> FEATURE:
<221> NAME/KEY: misc_feature
<222> LOCATION: (1945)..(1945)
<223> OTHER INFORMATION: n is a, c, g, or t
<220> FEATURE:
<221> NAME/KEY: misc_feature
<222> LOCATION: (1948)..(1948)
<223> OTHER INFORMATION: n is a, c, g, or t
<220> FEATURE:
<221> NAME/KEY: misc_feature
<222> LOCATION: (2001)..(2001)
<223> OTHER INFORMATION: n is a, c, g, or t
<220> FEATURE:
<221> NAME/KEY: misc_feature
<222> LOCATION: (2021)..(2022)
<223> OTHER INFORMATION: n is a, c, g, or t
<220> FEATURE:
<221> NAME/KEY: misc_feature
<222> LOCATION: (2059)..(2059)
<223> OTHER INFORMATION: n is a, c, g, or t
<220> FEATURE:
<221> NAME/KEY: misc_feature
<222> LOCATION: (2079)..(2079)
<223> OTHER INFORMATION: n is a, c, g, or t
<220> FEATURE:
<221> NAME/KEY: misc_feature
<222> LOCATION: (2089)..(2090)
<223> OTHER INFORMATION: n is a, c, g, or t
<220> FEATURE:
<221> NAME/KEY: misc_feature
<222> LOCATION: (2112)..(2112)
<223> OTHER INFORMATION: n is a, c, g, or t
<220> FEATURE:
<221> NAME/KEY: misc_feature
<222> LOCATION: (2116)..(2116)
<223> OTHER INFORMATION: n is a, c, g, or t
<220> FEATURE:
<221> NAME/KEY: misc_feature
<222> LOCATION: (2133)..(2133)
<223> OTHER INFORMATION: n is a, c, g, or t
<220> FEATURE:
<221> NAME/KEY: misc_feature
<222> LOCATION: (2165)..(2165)
<223> OTHER INFORMATION: n is a, c, g, or t
<220> FEATURE:
<221> NAME/KEY: misc_feature
<222> LOCATION: (2177)..(2177)
<223> OTHER INFORMATION: n is a, c, g, or t
<220> FEATURE:
<221> NAME/KEY: misc_feature
<222> LOCATION: (2201)..(2201)
<223> OTHER INFORMATION: n is a, c, g, or t
```

```
<220> FEATURE:
<221> NAME/KEY: misc_feature
<222> LOCATION: (2205)..(2205)
<223> OTHER INFORMATION: n is a, c, g, or t
<220> FEATURE:
<221> NAME/KEY: misc_feature
<222> LOCATION: (2216)..(2216)
<223> OTHER INFORMATION: n is a, c, g, or t
<220> FEATURE:
<221> NAME/KEY: misc_feature
<222> LOCATION: (2222)..(2224)
<223> OTHER INFORMATION: n is a, c, g, or t
<220> FEATURE:
<221> NAME/KEY: misc_feature
<222> LOCATION: (2233)..(2234)
<223> OTHER INFORMATION: n is a, c, g, or t
<220> FEATURE:
<221> NAME/KEY: misc_feature
<222> LOCATION: (2246)..(2246)
<223> OTHER INFORMATION: n is a, c, g, or t
<220> FEATURE:
<221> NAME/KEY: misc_feature
<222> LOCATION: (2248)..(2248)
<223> OTHER INFORMATION: n is a, c, g, or t
<220> FEATURE:
<221> NAME/KEY: misc_feature
<222> LOCATION: (2290)..(2290)
<223> OTHER INFORMATION: n is a, c, g, or t
<220> FEATURE:
<221> NAME/KEY: misc_feature
<222> LOCATION: (2370)..(2370)
<223> OTHER INFORMATION: n is a, c, g, or t
<220> FEATURE:
<221> NAME/KEY: misc_feature
<222> LOCATION: (2392)..(2394)
<223> OTHER INFORMATION: n is a, c, g, or t
<220> FEATURE:
<221> NAME/KEY: misc_feature
<222> LOCATION: (2404)..(2405)
<223> OTHER INFORMATION: n is a, c, g, or t
<220> FEATURE:
<221> NAME/KEY: misc_feature
<222> LOCATION: (2409)..(2410)
<223> OTHER INFORMATION: n is a, c, g, or t
<220> FEATURE:
<221> NAME/KEY: misc_feature
<222> LOCATION: (2469)..(2469)
<223> OTHER INFORMATION: n is a, c, g, or t
<220> FEATURE:
<221> NAME/KEY: misc_feature
<222> LOCATION: (2505)..(2505)
<223> OTHER INFORMATION: n is a, c, g, or t
<220> FEATURE:
<221> NAME/KEY: misc_feature
<222> LOCATION: (2519)..(2519)
<223> OTHER INFORMATION: n is a, c, g, or t
<220> FEATURE:
<221> NAME/KEY: misc_feature
<222> LOCATION: (2534)..(2536)
<223> OTHER INFORMATION: n is a, c, g, or t

<400> SEQUENCE: 27
tcgtaccgtt gcttctctca agtttagatt ttttccgta aaaagaggag gtggcccgtg      60
aagtttattc cctttaaaac ccaccaatta gctccttcac tctcagntct caacaatggc     120
ttcgactctg ggcggcgatg ngagaaacga gatagtgttt ttcgatcttg agacngcggt    180
tccgaccaaa tcggggcanc cttntgcgat tttggagttt ggggctatct tagtttgccc    240
tatgaagcta gtggagctct atagttactc cacnttggtt cgaccnaccg ancttctctc    300
catctccacg ctcacgaagc gacgaagcgg cattacgcgc gacggagttc tctctgcacc    360
tacattctct gaaatcgctg atgaagtcta cgacattctc cncggtaagg gtttctcttt    420
ttttttnnnn nnctnnctcn atctctctna cncgaagnta caagtattga ttttggtgtt    480
```

```
tctgtaggac gaatttgggn nggacataac ataaagagat tcgattgtgt aagaatanga        540
gatgcatttg cagnaattgg tctcnctccc ccggagccga aagctacaat tgattcactt        600
tcgttnntgt ctcagaagtt tgggaagaga gctggtgaca tgaaggtctc tcttttttcg        660
tctnctcgat gataaatctc aaagccnata gcttncttgt tatctttata gatatgaatt        720
tcnatgtaac ttcanagatt catcactcat caaagttgct aaaatttact ctnnnnnaan        780
aangtagatg gcatcgcntg ctacatattt cnggctagga gatcangctc acaggtnaaa        840
nnagtaaacg ataccntgtg cctttaacg attcaccagt tgtttcaata tgggactaaa         900
catggntang attcaccagg agcttagatg atgtccggat gaatcttgaa gtnntcaagn        960
actgtncaac cgtcttntt ctggtattgn tgtcttntca tttcttgaat aatgatnaac        1020 tctaantna aaaggattag attanagagg tngngacata tctganttct gtctacngtt        1080
tgcaaaagtt gggtccatct tccttncaga ccacancttt gcaagccgta aacatggntn        1140
nnnnnttgca agtatagttt gtnatatcac tgagtttaag tacttggtgt ttgcaggagt        1200
cnagtgtncc ngacattctt ananncatna gctggttntn cccaagaaaa agtccgngaa       1260
cacgaagtaa tgagaagtca ctgcctnatg gagtcagaga aagcccgact tcttcctctt       1320
cnagccctna aactgancg agttcgtctt ctgtagatgc cacanctgtc aaaaaccatc         1380
ccatcatttc tcttctgacg gaatgctcag naagngatac atctagttgt gaaatagatc       1440
catctgacat aaccactcta ataagtaaac tacatattgg aactcttaag anagatgctg       1500
cggacgaagc caaaactgtg agagatgcng cggangaagc caanantgta agacagcagg       1560
gtgaatcaac cgatcccaat gccaaagatg aatcattttt gggcgttaat gaagtatctg       1620
tttctancat cagggcaagt cttatcccgt tatatcgtng gngtctgaga atggagctgn       1680
ttcacaanga cnccctna catctctgnt ggtatagctt gaaaattcgg tttggaataa         1740
gccggaagta tgtggatcat gtaggtcgtc caaagatgaa tattgttgta gacatacntc       1800
ctgatttatg caagatcttg gacgcatncg atgctgctgc gcataactta ctgattgact      1860
caagcacaan ntcagatngg aggcctacng ttatgangaa anaaggcttt gncaactatc      1920
ccacagccag actgcagtaa gtatncanca ctctctctga ccttttacat acgagcatga       1980
atccaccgga gagtctctaa naccatctcc aaccctactc nntattcacc tccaaactct       2040
attttggagt taaatcccnc caaccctggc aaaatagana tcttcaaann tttctccat       2100 atttggagat tntganttt taagtcatga ctncattttg gagttgggtt ggagaaaaac        2160
acaantccaa aatagantta cttcattttg gagtaaaaaa ntgangaaat gggttngaga      2220
tnnnctaacc tcnntcacca ttcttntntt gttggcagaa taagctcaga atccaatgga      2280
acccaggtan accaaaaaga agaacctttg ggaaccaatc aaaagctcga tttcagtagc      2340
gataattttg aaaagcttga gtcagcactn cttcctggta ccctggttga tnnnttcttc      2400
tcanncgann cttacgatta taagaaaatg gtagggatac gtctagcagc cagaaagttg      2460
gtaatccanc tgaagaaatg atctagccaa ggaaaaatca ttccnctgtc tcttcctgnt     2520
cagtcggtga gcannn                                                     2536

<210> SEQ ID NO 28
<211> LENGTH: 1521
<212> TYPE: DNA
<213> ORGANISM: Boechera
<220> FEATURE:
<221> NAME/KEY: misc_feature
<222> LOCATION: (26)..(26)
<223> OTHER INFORMATION: n is a, c, g, or t
```

```
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (408)..(409)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (528)..(529)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (564)..(564)
```

-continued

```
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
```

```
<222> LOCATION: (908)..(908)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1054)..(1054)
<223> OTHER INFORMATION: n is a, c, g, or t
<220> FEATURE:
<221> NAME/KEY: misc_feature
<222> LOCATION: (1061)..(1061)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1190)..(1190)
<223> OTHER INFORMATION: n is a, c, g, or t
<220> FEATURE:
<221> NAME/KEY: misc_feature
<222> LOCATION: (1232)..(1233)
<223> OTHER INFORMATION: n is a, c, g, or t
<220> FEATURE:
<221> NAME/KEY: misc_feature
<222> LOCATION: (1240)..(1240)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1259)..(1259)
<223> OTHER INFORMATION: n is a, c, g, or t
<220> FEATURE:
<221> NAME/KEY: misc_feature
<222> LOCATION: (1264)..(1264)
<223> OTHER INFORMATION: n is a, c, g, or t
<220> FEATURE:
<221> NAME/KEY: misc_feature
<222> LOCATION: (1274)..(1274)
<223> OTHER INFORMATION: n is a, c, g, or t
<220> FEATURE:
<221> NAME/KEY: misc_feature
<222> LOCATION: (1330)..(1330)
<223> OTHER INFORMATION: n is a, c, g, or t
<220> FEATURE:
<221> NAME/KEY: misc_feature
<222> LOCATION: (1410)..(1410)
<223> OTHER INFORMATION: n is a, c, g, or t
<220> FEATURE:
<221> NAME/KEY: misc_feature
<222> LOCATION: (1432)..(1434)
<223> OTHER INFORMATION: n is a, c, g, or t
<220> FEATURE:
```

<221> NAME/KEY: misc_feature
<222> LOCATION: (1444)..(1445)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t

<400> SEQUENCE: 28

```
atggcttcga ctctgggcgg cgatgngaga aacgagatag tgttttcga tcttgagacn      60
gcggttccga ccaaatcggg gcanccttnt gcgattttgg agtttggggc tatcttagtt    120
tgccctatga agctagtgga gctctatagt tactccacnt tggttcgacc naccganctt    180
tctctcatct ccacgctcac gaagcgacga agcggcatta cgcgcgacgg agttctctct    240
gcacctacat tctctgaaat cgctgatgaa gtctacgaca ttctccncgg acgaatttgg    300
gnnggacata acataaagag attcgattgt gtaagaatan gagatgcatt tgcagnaatt    360
ggtctcnctc ccccggagcc gaaagctaca attgattcac tttcgttnnt gtctcagaag    420
tttgggaaga gagctggtga catgaagatg gcatcgcntg ctacatattt cnggctagga    480
gatcangctc acaggagctt agatgatgtc cggatgaatc ttgaagtnnt caagnactgt    540
ncaaccgtct tntttctgga gtcnagtgtn ccngacattc ttananncat nagctggttn    600
tncccaagaa aaagtccgng aacacgaagt aatgagaagt cactgcctna tggagtcaga    660
gaaagcccga cttcttcctc ttcnagcccc naaactganc cgagttcgtc ttctgtagat    720
gccacanctg tcaaaaacca tcccatcatt tctcttctga cggaatgctc agnaagngat    780
acatctagtt gtgaaataga tccatctgac ataaccactc taataagtaa actacatatt    840
ggaactctta aganagatgc tgcggacgaa gccaaaactg tgagagatgc ngcggangaa    900
gccaanantg taagacagca gggtgaatca accgatccca atgccaaaga tgaatcattt    960
ttgggcgtta atgaagtatc tgtttctanc atcagggcaa gtcttatccc gttatatcgt   1020
nggngtctga gaatggagct gnttcacaan gacnccctc nacatctctg ntggtatagc    1080
ttgaaaattc ggtttggaat aagccggaag tatgtggatc atgtaggtcg tccaaagatg   1140
aatattgttg tagacatacn tcctgattta tgcaagatct tggacgcatn cgatgctgct   1200
gcgcataact tactgattga ctcaagcaca anntcagatn ggaggcctac ngttatgang   1260
aaanaaggct ttgncaacta tcccacagcc agactgcaaa taagctcaga atccaatgga   1320
acccaggtan accaaaaaga agaaccttg ggaaccaatc aaaagctcga tttcagtagc    1380
gataattttg aaaagcttga gtcagcactn cttcctggta ccctggttga tnnnttcttc   1440
tcanncgann cttacgatta taagaaaatg gtagggatac gtctagcagc cagaaagttg   1500
gtaatccanc tgaagaaatg a                                              1521
```

<210> SEQ ID NO 29
<211> LENGTH: 2506
<212> TYPE: DNA
<213> ORGANISM: Boechera
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t -continued

```
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (427)..(432)
<223> OTHER INFORMATION: n is a, c, g, or t
<220> FEATURE:
<221> NAME/KEY: misc_feature
<222> LOCATION: (435)..(436)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (500)..(501)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (687)..(687)
```

-continued

```
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (773)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
```

```
<222> LOCATION: (997)..(997)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1054)..(1054)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1106)..(1106)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
<220> FEATURE:
<221> NAME/KEY: misc_feature
<222> LOCATION: (1140)..(1145)
<223> OTHER INFORMATION: n is a, c, g, or t
<220> FEATURE:
<221> NAME/KEY: misc_feature
<222> LOCATION: (1163)..(1163)
<223> OTHER INFORMATION: n is a, c, g, or t
<220> FEATURE:
<221> NAME/KEY: misc_feature
<222> LOCATION: (1202)..(1202)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1211)..(1211)
<223> OTHER INFORMATION: n is a, c, g, or t
<220> FEATURE:
<221> NAME/KEY: misc_feature
<222> LOCATION: (1222)..(1222)
<223> OTHER INFORMATION: n is a, c, g, or t
<220> FEATURE:
<221> NAME/KEY: misc_feature
<222> LOCATION: (1224)..(1225)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
```

-continued

```
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1240)..(1240)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1322)..(1322)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1337)..(1337)
<223> OTHER INFORMATION: n is a, c, g, or t
<220> FEATURE:
<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1411)..(1411)
<223> OTHER INFORMATION: n is a, c, g, or t
<220> FEATURE:
<221> NAME/KEY: misc_feature
<222> LOCATION: (1415)..(1415)
<223> OTHER INFORMATION: n is a, c, g, or t
<220> FEATURE:
<221> NAME/KEY: misc_feature
<222> LOCATION: (1492)..(1492)
<223> OTHER INFORMATION: n is a, c, g, or t
<220> FEATURE:
<221> NAME/KEY: misc_feature
<222> LOCATION: (1499)..(1499)
<223> OTHER INFORMATION: n is a, c, g, or t
<220> FEATURE:
<221> NAME/KEY: misc_feature
<222> LOCATION: (1505)..(1505)
<223> OTHER INFORMATION: n is a, c, g, or t
<220> FEATURE:
<221> NAME/KEY: misc_feature
<222> LOCATION: (1514)..(1514)
<223> OTHER INFORMATION: n is a, c, g, or t
<220> FEATURE:
<221> NAME/KEY: misc_feature
<222> LOCATION: (1516)..(1516)
<223> OTHER INFORMATION: n is a, c, g, or t
<220> FEATURE:
<221> NAME/KEY: misc_feature
<222> LOCATION: (1597)..(1597)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1650)..(1650)
<223> OTHER INFORMATION: n is a, c, g, or t
<220> FEATURE:
<221> NAME/KEY: misc_feature
<222> LOCATION: (1658)..(1658)
<223> OTHER INFORMATION: n is a, c, g, or t
```

-continued

```
<220> FEATURE:
<221> NAME/KEY: misc_feature
<222> LOCATION: (1662)..(1662)
<223> OTHER INFORMATION: n is a, c, g, or t
<220> FEATURE:
<221> NAME/KEY: misc_feature
<222> LOCATION: (1669)..(1669)
<223> OTHER INFORMATION: n is a, c, g, or t
<220> FEATURE:
<221> NAME/KEY: misc_feature
<222> LOCATION: (1679)..(1679)
<223> OTHER INFORMATION: n is a, c, g, or t
<220> FEATURE:
<221> NAME/KEY: misc_feature
<222> LOCATION: (1768)..(1768)
<223> OTHER INFORMATION: n is a, c, g, or t
<220> FEATURE:
<221> NAME/KEY: misc_feature
<222> LOCATION: (1798)..(1798)
<223> OTHER INFORMATION: n is a, c, g, or t
<220> FEATURE:
<221> NAME/KEY: misc_feature
<222> LOCATION: (1840)..(1841)
<223> OTHER INFORMATION: n is a, c, g, or t
<220> FEATURE:
<221> NAME/KEY: misc_feature
<222> LOCATION: (1848)..(1848)
<223> OTHER INFORMATION: n is a, c, g, or t
<220> FEATURE:
<221> NAME/KEY: misc_feature
<222> LOCATION: (1859)..(1859)
<223> OTHER INFORMATION: n is a, c, g, or t
<220> FEATURE:
<221> NAME/KEY: misc_feature
<222> LOCATION: (1867)..(1867)
<223> OTHER INFORMATION: n is a, c, g, or t
<220> FEATURE:
<221> NAME/KEY: misc_feature
<222> LOCATION: (1872)..(1872)
<223> OTHER INFORMATION: n is a, c, g, or t
<220> FEATURE:
<221> NAME/KEY: misc_feature
<222> LOCATION: (1882)..(1882)
<223> OTHER INFORMATION: n is a, c, g, or t
<220> FEATURE:
<221> NAME/KEY: misc_feature
<222> LOCATION: (1915)..(1915)
<223> OTHER INFORMATION: n is a, c, g, or t
<220> FEATURE:
<221> NAME/KEY: misc_feature
<222> LOCATION: (1918)..(1918)
<223> OTHER INFORMATION: n is a, c, g, or t
<220> FEATURE:
<221> NAME/KEY: misc_feature
<222> LOCATION: (1971)..(1971)
<223> OTHER INFORMATION: n is a, c, g, or t
<220> FEATURE:
<221> NAME/KEY: misc_feature
<222> LOCATION: (1991)..(1992)
<223> OTHER INFORMATION: n is a, c, g, or t
<220> FEATURE:
<221> NAME/KEY: misc_feature
<222> LOCATION: (2029)..(2029)
<223> OTHER INFORMATION: n is a, c, g, or t
<220> FEATURE:
<221> NAME/KEY: misc_feature
<222> LOCATION: (2049)..(2049)
<223> OTHER INFORMATION: n is a, c, g, or t
<220> FEATURE:
<221> NAME/KEY: misc_feature
<222> LOCATION: (2059)..(2060)
<223> OTHER INFORMATION: n is a, c, g, or t
<220> FEATURE:
<221> NAME/KEY: misc_feature
<222> LOCATION: (2082)..(2082)
<223> OTHER INFORMATION: n is a, c, g, or t
<220> FEATURE:
<221> NAME/KEY: misc_feature
<222> LOCATION: (2086)..(2086)
```

```
<223> OTHER INFORMATION: n is a, c, g, or t
<220> FEATURE:
<221> NAME/KEY: misc_feature
<222> LOCATION: (2103)..(2103)
<223> OTHER INFORMATION: n is a, c, g, or t
<220> FEATURE:
<221> NAME/KEY: misc_feature
<222> LOCATION: (2135)..(2135)
<223> OTHER INFORMATION: n is a, c, g, or t
<220> FEATURE:
<221> NAME/KEY: misc_feature
<222> LOCATION: (2147)..(2147)
<223> OTHER INFORMATION: n is a, c, g, or t
<220> FEATURE:
<221> NAME/KEY: misc_feature
<222> LOCATION: (2171)..(2171)
<223> OTHER INFORMATION: n is a, c, g, or t
<220> FEATURE:
<221> NAME/KEY: misc_feature
<222> LOCATION: (2175)..(2175)
<223> OTHER INFORMATION: n is a, c, g, or t
<220> FEATURE:
<221> NAME/KEY: misc_feature
<222> LOCATION: (2186)..(2186)
<223> OTHER INFORMATION: n is a, c, g, or t
<220> FEATURE:
<221> NAME/KEY: misc_feature
<222> LOCATION: (2192)..(2194)
<223> OTHER INFORMATION: n is a, c, g, or t
<220> FEATURE:
<221> NAME/KEY: misc_feature
<222> LOCATION: (2203)..(2204)
<223> OTHER INFORMATION: n is a, c, g, or t
<220> FEATURE:
<221> NAME/KEY: misc_feature
<222> LOCATION: (2216)..(2216)
<223> OTHER INFORMATION: n is a, c, g, or t
<220> FEATURE:
<221> NAME/KEY: misc_feature
<222> LOCATION: (2218)..(2218)
<223> OTHER INFORMATION: n is a, c, g, or t
<220> FEATURE:
<221> NAME/KEY: misc_feature
<222> LOCATION: (2260)..(2260)
<223> OTHER INFORMATION: n is a, c, g, or t
<220> FEATURE:
<221> NAME/KEY: misc_feature
<222> LOCATION: (2340)..(2340)
<223> OTHER INFORMATION: n is a, c, g, or t
<220> FEATURE:
<221> NAME/KEY: misc_feature
<222> LOCATION: (2362)..(2364)
<223> OTHER INFORMATION: n is a, c, g, or t
<220> FEATURE:
<221> NAME/KEY: misc_feature
<222> LOCATION: (2374)..(2375)
<223> OTHER INFORMATION: n is a, c, g, or t
<220> FEATURE:
<221> NAME/KEY: misc_feature
<222> LOCATION: (2379)..(2380)
<223> OTHER INFORMATION: n is a, c, g, or t
<220> FEATURE:
<221> NAME/KEY: misc_feature
<222> LOCATION: (2439)..(2439)
<223> OTHER INFORMATION: n is a, c, g, or t
<220> FEATURE:
<221> NAME/KEY: misc_feature
<222> LOCATION: (2475)..(2475)
<223> OTHER INFORMATION: n is a, c, g, or t
<220> FEATURE:
<221> NAME/KEY: misc_feature
<222> LOCATION: (2489)..(2489)
<223> OTHER INFORMATION: n is a, c, g, or t
<220> FEATURE:
<221> NAME/KEY: misc_feature
<222> LOCATION: (2504)..(2506)
<223> OTHER INFORMATION: n is a, c, g, or t

<400> SEQUENCE: 29
```

```
tcgtaccgtt gcttctctca agtttagatt ttttccgta aaagaggag gtggcccgtg    60 aagtttattc cctttaaaac ccaccaatta gctccttcac tctcagntct caacaatggc   120
ttcgactctg ggcggcgatg ngagaaacga gatagtgttt ttcgatcttg agacngcggt   180
tccgaccaaa tcggggcanc cttntgcgat tttggagttt ggggctatct tagtttgccc   240
tatgaagcta gtggagctct atagttactc cacnttggtt cgaccnaccg anctttctct   300
catctccacg ctcacgaagc gacgaagcgg cattacgcgc gacggagttc tctctgcacc   360
tacattctct gaaatcgctg atgaagtcta cgacattctc cncggtaagg gtttctcttt   420 tttttttnnnn nnctnnctcn atctctctna cncgaagnta caagtattga ttttggtgtt   480
tctgtaggac gaatttgggn nggacataac ataaagagat tcgattgtgt aagaatanga   540
gatgcatttg cagnaattgg tctcnctccc ccggagccga aagctacaat tgattcactt   600
tcgttnntgt ctcagaagtt tgggaagaga gctggtgaca tgaaggtctc tcttttttcg   660
tctnctcgat gataaatctc aaagccnata gcttncttgt tatctttata gatatgaatt   720
tcnatgtaac ttcanagatt catcactcat caaagttgct aaaatttact ctnnnnnaan   780
aangtagatg gcatcgcntg ctacatattt cnggctagga gatcangctc acaggtnaaa   840
nnagtaaacg ataccntgtg cctttaacg attcaccagt tgtttcaata tgggactaaa   900
catggntang attcaccagg agcttagatg atgtccggat gaatcttgaa gtnntcaagn   960
actgtncaac cgtcttnttt ctggtattgn tgtcttntca tttcttgaat aatgataac  1020 tctaanttna aaaggattag attanagagg tngngacata tctganttct gtctacngtt  1080
tgcaaaagtt gggtccatct tccttncaga ccacancttt gcaagccgta aacatggntn  1140
nnnnnttgca agtatagttt gtnatatcac tgagtttaag tacttggtgt ttgcaggagt  1200
cnagtgtncc ngacattctt ananncatna gctggttntn cccaagaaaa agtccgngaa  1260
cacgaagtaa tgagaagtca ctgcctnatg gagtcagaga aagcccgact tcttcctctt  1320
cnagccctna aactganccg agttcgtctt ctgtagatgc cacanctgtc aaaaaccatc  1380
ccatcatttc tcttctgacg gaatgctcag naagngatac atctagttgt gaaatagatc  1440
catctgacat aaccactcta ataagtaaac tacatattgg aactcttaag anagatgcng  1500
cggangaagc caanantgta agacagcagg gtgaatcaac cgatcccaat gccaaagatg  1560
aatcattttt gggcgttaat gaagtatctg tttctancat cagggcaagt cttatcccgt  1620
tatatcgtng gngtctgaga atggagctgn ttcacaanga cnccctcna catctctgnt  1680 ggtatagctt gaaaattcgg tttggaataa gccggaagta tgtggatcat gtaggtcgtc  1740
caaagatgaa tattgttgta gacatacntc ctgatttatg caagatcttg gacgcatncg  1800
atgctgctgc gcataactta ctgattgact caagcacaan ntcagatngg aggcctacng  1860
ttatgangaa anaaggcttt gncaactatc ccacagccag actgcagtaa gtatncanca  1920
ctctctctga ccttttacat acgagcatga atccaccgga gagtctctaa naccatctcc  1980
aaccctactc nntattcacc tccaaactct attttggagt taaatcccnc caacccttgc  2040
aaaatagana tcttcaaann ttttctccat atttggagat tntganttt taagtcatga  2100 ctncattttg gagttgggtt ggagaaaaac acaantccaa aatagantta cttcattttg  2160
gagtaaaaaa ntgangaaat gggttngaga tnnnctaacc tcnntcacca ttcttntntt  2220
gttggcagaa taagctcaga atccaatgga acccaggtan accaaaaaga agaacctttg  2280
ggaaccaatc aaaagctcga tttcagtagc gataattttg aaaagcttga gtcagcactn  2340
```

```
cttcctggta ccctggttga tnnnttcttc tcanncgann cttacgatta taagaaaatg    2400
gtagggatac gtctagcagc cagaaagttg gtaatccanc tgaagaaatg atctagccaa    2460
ggaaaaatca ttccnctgtc tcttcctgnt cagtcggtga gcannn                   2506
```

```
<210> SEQ ID NO 30
<211> LENGTH: 1491
<212> TYPE: DNA
<213> ORGANISM: Boechera
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (408)..(409)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (528)..(529)
<223> OTHER INFORMATION: n is a, c, g, or t
```

-continued

```
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (854)..(854)
```

```
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1202)..(1203)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1234)..(1234)
<223> OTHER INFORMATION: n is a, c, g, or t
<220> FEATURE:
<221> NAME/KEY: misc_feature
```

<222> LOCATION: (1244)..(1244)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1402)..(1404)
<223> OTHER INFORMATION: n is a, c, g, or t
<220> FEATURE:
<221> NAME/KEY: misc_feature
<222> LOCATION: (1414)..(1415)
<223> OTHER INFORMATION: n is a, c, g, or t
<220> FEATURE:
<221> NAME/KEY: misc_feature
<222> LOCATION: (1419)..(1420)
<223> OTHER INFORMATION: n is a, c, g, or t
<220> FEATURE:
<221> NAME/KEY: misc_feature
<222> LOCATION: (1479)..(1479)
<223> OTHER INFORMATION: n is a, c, g, or t

<400> SEQUENCE: 30

| | | |
|---|---|---|
| atggcttcga ctctgggcgg cgatgngaga aacgagatag tgttttcga tcttgagacn | 60 |
| gcggttccga ccaaatcggg gcanccttnt gcgattttgg agtttggggc tatcttagtt | 120 |
| tgccctatga agctagtgga gctctatagt tactccacnt tggttcgacc naccganctt | 180 |
| tctctcatct ccacgctcac gaagcgacga agcggcatta cgcgcgacgg agttctctct | 240 |
| gcacctacat tctctgaaat cgctgatgaa gtctacgaca ttctccncgg acgaatttgg | 300 |
| gnnggacata acataaagag attcgattgt gtaagaatan gagatgcatt tgcagnaatt | 360 |
| ggtctcnctc ccccggagcc gaaagctaca attgattcac tttcgttnnt gtctcagaag | 420 |
| tttgggaaga gagctggtga catgaagatg gcatcgcntg ctacatattt cnggctagga | 480 |
| gatcangctc acaggagctt agatgatgtc cggatgaatc ttgaagtnnt caagnactgt | 540 |
| ncaaccgtct tntttctgga gtcnagtgtn ccngacattc ttanannncat nagctggttn | 600 |
| tncccaagaa aaagtccgng aacacgaagt aatgagaagt cactgcctna tggagtcaga | 660 |
| gaaagcccga cttcttcctc ttcnagccct naaactganc cgagttcgtc ttctgtagat | 720 |
| gccacanctg tcaaaaacca tcccatcatt tctcttctga cggaatgctc agnaagngat | 780 |
| acatctagtt gtgaaataga tccatctgac ataaccactc taataagtaa actacatatt | 840 |
| ggaactctta aganagatgc ngcggangaa gccaanantg taagacagca gggtgaatca | 900 |
| accgatccca atgccaaaga tgaatcattt ttgggcgtta atgaagtatc tgtttctanc | 960 |
| atcagggcaa gtcttatccc gttatatcgt nggngtctga gaatggagct gnttcacaan | 1020 |
| gacnccctc nacatctctg ntggtatagc ttgaaaattc ggtttggaat aagccggaag | 1080 |
| tatgtggatc atgtaggtcg tccaaagatg aatattgttg tagacatacn tcctgattta | 1140 |
| tgcaagatct tggacgcatn cgatgctgct gcgcataact tactgattga ctcaagcaca | 1200 |
| anntcagatn ggaggcctac ngttatgang aaanaaggct ttgncaacta tcccacagcc | 1260 |
| agactgcaaa taagctcaga atccaatgga acccaggtan accaaaaaga gaacctttg | 1320 |
| ggaaccaatc aaaagctcga tttcagtagc gataattttg aaaagcttga gtcagcactn | 1380 |
| cttcctggta ccctggttga tnnnttcttc tcanncgann cttacgatta taagaaaatg | 1440 |
| gtagggatac gtctagcagc cagaaagttg gtaatccanc tgaagaaatg a | 1491 |

<210> SEQ ID NO 31
<211> LENGTH: 495
<212> TYPE: DNA
<213> ORGANISM: Boechera
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (263)..(264)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (369)..(370)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (489)..(490)
<223> OTHER INFORMATION: n is a, c, g, or t

<400> SEQUENCE: 31
gtgtttttcg atcttgagac ngcggttccg accaaatcgg ggcanccttn tgcgattttg     60
gagtttgggg ctatcttagt ttgccctatg aagctagtgg agctctatag ttactccacn    120
ttggttcgac cnaccganct ttctctcatc tccacgctca cgaagcgacg aagcggcatt    180
acgcgcgacg gagttctctc tgcacctaca ttctctgaaa tcgctgatga agtctacgac    240

-continued

```
attctccncg gacgaatttg ggnnggacat aacataaaga gattcgattg tgtaagaata    300
ngagatgcat ttgcagnaat tggtctcnct cccccggagc cgaaagctac aattgattca    360
ctttcgttnn tgtctcagaa gtttgggaag agagctggtg acatgaagat ggcatcgcnt    420
gctacatatt tcnggctagg agatcangct cacaggagct tagatgatgt ccggatgaat    480
cttgaagtnn tcaag                                                    495
```

```
<210> SEQ ID NO 32
<211> LENGTH: 2528
<212> TYPE: DNA
<213> ORGANISM: Boechera
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (135)..(137)
```

```
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
```

```
<222> LOCATION: (408)..(409)
<223> OTHER INFORMATION: n is a, c, g, or t
<220> FEATURE:
<221> NAME/KEY: misc_feature
<222> LOCATION: (417)..(422)
<223> OTHER INFORMATION: n is a, c, g, or t
<220> FEATURE:
<221> NAME/KEY: misc_feature
<222> LOCATION: (425)..(426)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (562)..(563)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
```

-continued

```
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (763)..(767)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
```

```
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (831)..(832)
<223> OTHER INFORMATION: n is a, c, g, or t
<220> FEATURE:
<221> NAME/KEY: misc_feature
<222> LOCATION: (845)..(846)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (943)..(944)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (962)..(962)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (1007)..(1007)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
<222> LOCATION: (1017)..(1017)
```

```
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1044)..(1045)
<223> OTHER INFORMATION: n is a, c, g, or t
<220> FEATURE:
<221> NAME/KEY: misc_feature
<222> LOCATION: (1057)..(1057)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1072)..(1072)
<223> OTHER INFORMATION: n is a, c, g, or t
<220> FEATURE:
<221> NAME/KEY: misc_feature
<222> LOCATION: (1075)..(1075)
<223> OTHER INFORMATION: n is a, c, g, or t
<220> FEATURE:
<221> NAME/KEY: misc_feature
<222> LOCATION: (1081)..(1082)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1088)..(1088)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1154)..(1154)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1216)..(1217)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1232)..(1232)
<223> OTHER INFORMATION: n is a, c, g, or t
<220> FEATURE:
<221> NAME/KEY: misc_feature
```

```
<222> LOCATION: (1235)..(1235)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1324)..(1324)
<223> OTHER INFORMATION: n is a, c, g, or t
<220> FEATURE:
<221> NAME/KEY: misc_feature
<222> LOCATION: (1348)..(1348)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1357)..(1357)
<223> OTHER INFORMATION: n is a, c, g, or t
<220> FEATURE:
<221> NAME/KEY: misc_feature
<222> LOCATION: (1406)..(1407)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1484)..(1484)
<223> OTHER INFORMATION: n is a, c, g, or t
<220> FEATURE:
<221> NAME/KEY: misc_feature
<222> LOCATION: (1518)..(1518)
<223> OTHER INFORMATION: n is a, c, g, or t
<220> FEATURE:
<221> NAME/KEY: misc_feature
<222> LOCATION: (1525)..(1525)
<223> OTHER INFORMATION: n is a, c, g, or t
<220> FEATURE:
<221> NAME/KEY: misc_feature
<222> LOCATION: (1527)..(1527)
<223> OTHER INFORMATION: n is a, c, g, or t
<220> FEATURE:
<221> NAME/KEY: misc_feature
<222> LOCATION: (1538)..(1538)
<223> OTHER INFORMATION: n is a, c, g, or t
<220> FEATURE:
<221> NAME/KEY: misc_feature
<222> LOCATION: (1551)..(1551)
<223> OTHER INFORMATION: n is a, c, g, or t
<220> FEATURE:
<221> NAME/KEY: misc_feature
<222> LOCATION: (1593)..(1593)
<223> OTHER INFORMATION: n is a, c, g, or t
<220> FEATURE:
```

```
<221> NAME/KEY: misc_feature
<222> LOCATION: (1605)..(1605)
<223> OTHER INFORMATION: n is a, c, g, or t
<220> FEATURE:
<221> NAME/KEY: misc_feature
<222> LOCATION: (1612)..(1612)
<223> OTHER INFORMATION: n is a, c, g, or t
<220> FEATURE:
<221> NAME/KEY: misc_feature
<222> LOCATION: (1620)..(1621)
<223> OTHER INFORMATION: n is a, c, g, or t
<220> FEATURE:
<221> NAME/KEY: misc_feature
<222> LOCATION: (1636)..(1636)
<223> OTHER INFORMATION: n is a, c, g, or t
<220> FEATURE:
<221> NAME/KEY: misc_feature
<222> LOCATION: (1638)..(1638)
<223> OTHER INFORMATION: n is a, c, g, or t
<220> FEATURE:
<221> NAME/KEY: misc_feature
<222> LOCATION: (1651)..(1651)
<223> OTHER INFORMATION: n is a, c, g, or t
<220> FEATURE:
<221> NAME/KEY: misc_feature
<222> LOCATION: (1654)..(1654)
<223> OTHER INFORMATION: n is a, c, g, or t
<220> FEATURE:
<221> NAME/KEY: misc_feature
<222> LOCATION: (1672)..(1672)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1683)..(1683)
<223> OTHER INFORMATION: n is a, c, g, or t
<220> FEATURE:
<221> NAME/KEY: misc_feature
<222> LOCATION: (1699)..(1699)
<223> OTHER INFORMATION: n is a, c, g, or t
<220> FEATURE:
<221> NAME/KEY: misc_feature
<222> LOCATION: (1701)..(1701)
<223> OTHER INFORMATION: n is a, c, g, or t
<220> FEATURE:
<221> NAME/KEY: misc_feature
<222> LOCATION: (1709)..(1709)
<223> OTHER INFORMATION: n is a, c, g, or t
<220> FEATURE:
<221> NAME/KEY: misc_feature
<222> LOCATION: (1711)..(1711)
<223> OTHER INFORMATION: n is a, c, g, or t
<220> FEATURE:
<221> NAME/KEY: misc_feature
<222> LOCATION: (1734)..(1734)
<223> OTHER INFORMATION: n is a, c, g, or t
<220> FEATURE:
<221> NAME/KEY: misc_feature
<222> LOCATION: (1742)..(1742)
<223> OTHER INFORMATION: n is a, c, g, or t
<220> FEATURE:
<221> NAME/KEY: misc_feature
<222> LOCATION: (1761)..(1761)
<223> OTHER INFORMATION: n is a, c, g, or t
<220> FEATURE:
<221> NAME/KEY: misc_feature
<222> LOCATION: (1779)..(1779)
<223> OTHER INFORMATION: n is a, c, g, or t
<220> FEATURE:
<221> NAME/KEY: misc_feature
<222> LOCATION: (1782)..(1782)
<223> OTHER INFORMATION: n is a, c, g, or t
<220> FEATURE:
<221> NAME/KEY: misc_feature
<222> LOCATION: (1820)..(1822)
<223> OTHER INFORMATION: n is a, c, g, or t
```

-continued

```
<220> FEATURE:
<221> NAME/KEY: misc_feature
<222> LOCATION: (1828)..(1828)
<223> OTHER INFORMATION: n is a, c, g, or t
<220> FEATURE:
<221> NAME/KEY: misc_feature
<222> LOCATION: (1862)..(1863)
<223> OTHER INFORMATION: n is a, c, g, or t
<220> FEATURE:
<221> NAME/KEY: misc_feature
<222> LOCATION: (1869)..(1870)
<223> OTHER INFORMATION: n is a, c, g, or t
<220> FEATURE:
<221> NAME/KEY: misc_feature
<222> LOCATION: (1881)..(1881)
<223> OTHER INFORMATION: n is a, c, g, or t
<220> FEATURE:
<221> NAME/KEY: misc_feature
<222> LOCATION: (1889)..(1889)
<223> OTHER INFORMATION: n is a, c, g, or t
<220> FEATURE:
<221> NAME/KEY: misc_feature
<222> LOCATION: (1894)..(1894)
<223> OTHER INFORMATION: n is a, c, g, or t
<220> FEATURE:
<221> NAME/KEY: misc_feature
<222> LOCATION: (1917)..(1917)
<223> OTHER INFORMATION: n is a, c, g, or t
<220> FEATURE:
<221> NAME/KEY: misc_feature
<222> LOCATION: (1921)..(1921)
<223> OTHER INFORMATION: n is a, c, g, or t
<220> FEATURE:
<221> NAME/KEY: misc_feature
<222> LOCATION: (1940)..(1940)
<223> OTHER INFORMATION: n is a, c, g, or t
<220> FEATURE:
<221> NAME/KEY: misc_feature
<222> LOCATION: (1952)..(1952)
<223> OTHER INFORMATION: n is a, c, g, or t
<220> FEATURE:
<221> NAME/KEY: misc_feature
<222> LOCATION: (1965)..(1965)
<223> OTHER INFORMATION: n is a, c, g, or t
<220> FEATURE:
<221> NAME/KEY: misc_feature
<222> LOCATION: (1971)..(1971)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (1979)..(1979)
<223> OTHER INFORMATION: n is a, c, g, or t
<220> FEATURE:
<221> NAME/KEY: misc_feature
<222> LOCATION: (1993)..(1993)
<223> OTHER INFORMATION: n is a, c, g, or t
<220> FEATURE:
<221> NAME/KEY: misc_feature
<222> LOCATION: (2006)..(2006)
<223> OTHER INFORMATION: n is a, c, g, or t
<220> FEATURE:
<221> NAME/KEY: misc_feature
<222> LOCATION: (2013)..(2014)
<223> OTHER INFORMATION: n is a, c, g, or t
<220> FEATURE:
<221> NAME/KEY: misc_feature
<222> LOCATION: (2016)..(2016)
<223> OTHER INFORMATION: n is a, c, g, or t
<220> FEATURE:
<221> NAME/KEY: misc_feature
<222> LOCATION: (2023)..(2023)
<223> OTHER INFORMATION: n is a, c, g, or t
<220> FEATURE:
<221> NAME/KEY: misc_feature
<222> LOCATION: (2029)..(2029)
```

-continued

```
<223> OTHER INFORMATION: n is a, c, g, or t
<220> FEATURE:
<221> NAME/KEY: misc_feature
<222> LOCATION: (2056)..(2057)
<223> OTHER INFORMATION: n is a, c, g, or t
<220> FEATURE:
<221> NAME/KEY: misc_feature
<222> LOCATION: (2069)..(2071)
<223> OTHER INFORMATION: n is a, c, g, or t
<220> FEATURE:
<221> NAME/KEY: misc_feature
<222> LOCATION: (2081)..(2082)
<223> OTHER INFORMATION: n is a, c, g, or t
<220> FEATURE:
<221> NAME/KEY: misc_feature
<222> LOCATION: (2108)..(2108)
<223> OTHER INFORMATION: n is a, c, g, or t
<220> FEATURE:
<221> NAME/KEY: misc_feature
<222> LOCATION: (2113)..(2113)
<223> OTHER INFORMATION: n is a, c, g, or t
<220> FEATURE:
<221> NAME/KEY: misc_feature
<222> LOCATION: (2142)..(2142)
<223> OTHER INFORMATION: n is a, c, g, or t
<220> FEATURE:
<221> NAME/KEY: misc_feature
<222> LOCATION: (2157)..(2157)
<223> OTHER INFORMATION: n is a, c, g, or t
<220> FEATURE:
<221> NAME/KEY: misc_feature
<222> LOCATION: (2169)..(2169)
<223> OTHER INFORMATION: n is a, c, g, or t
<220> FEATURE:
<221> NAME/KEY: misc_feature
<222> LOCATION: (2184)..(2184)
<223> OTHER INFORMATION: n is a, c, g, or t
<220> FEATURE:
<221> NAME/KEY: misc_feature
<222> LOCATION: (2193)..(2193)
<223> OTHER INFORMATION: n is a, c, g, or t
<220> FEATURE:
<221> NAME/KEY: misc_feature
<222> LOCATION: (2208)..(2208)
<223> OTHER INFORMATION: n is a, c, g, or t
<220> FEATURE:
<221> NAME/KEY: misc_feature
<222> LOCATION: (2214)..(2216)
<223> OTHER INFORMATION: n is a, c, g, or t
<220> FEATURE:
<221> NAME/KEY: misc_feature
<222> LOCATION: (2225)..(2226)
<223> OTHER INFORMATION: n is a, c, g, or t
<220> FEATURE:
<221> NAME/KEY: misc_feature
<222> LOCATION: (2228)..(2228)
<223> OTHER INFORMATION: n is a, c, g, or t
<220> FEATURE:
<221> NAME/KEY: misc_feature
<222> LOCATION: (2230)..(2230)
<223> OTHER INFORMATION: n is a, c, g, or t
<220> FEATURE:
<221> NAME/KEY: misc_feature
<222> LOCATION: (2233)..(2233)
<223> OTHER INFORMATION: n is a, c, g, or t
<220> FEATURE:
<221> NAME/KEY: misc_feature
<222> LOCATION: (2236)..(2236)
<223> OTHER INFORMATION: n is a, c, g, or t
<220> FEATURE:
<221> NAME/KEY: misc_feature
<222> LOCATION: (2238)..(2238)
<223> OTHER INFORMATION: n is a, c, g, or t
<220> FEATURE:
<221> NAME/KEY: misc_feature
<222> LOCATION: (2240)..(2240)
<223> OTHER INFORMATION: n is a, c, g, or t
<220> FEATURE:
<221> NAME/KEY: misc_feature
```

-continued

```
<222> LOCATION: (2248)..(2248)
<223> OTHER INFORMATION: n is a, c, g, or t
<220> FEATURE:
<221> NAME/KEY: misc_feature
<222> LOCATION: (2260)..(2260)
<223> OTHER INFORMATION: n is a, c, g, or t
<220> FEATURE:
<221> NAME/KEY: misc_feature
<222> LOCATION: (2270)..(2270)
<223> OTHER INFORMATION: n is a, c, g, or t
<220> FEATURE:
<221> NAME/KEY: misc_feature
<222> LOCATION: (2277)..(2277)
<223> OTHER INFORMATION: n is a, c, g, or t
<220> FEATURE:
<221> NAME/KEY: misc_feature
<222> LOCATION: (2282)..(2282)
<223> OTHER INFORMATION: n is a, c, g, or t
<220> FEATURE:
<221> NAME/KEY: misc_feature
<222> LOCATION: (2295)..(2295)
<223> OTHER INFORMATION: n is a, c, g, or t
<220> FEATURE:
<221> NAME/KEY: misc_feature
<222> LOCATION: (2350)..(2350)
<223> OTHER INFORMATION: n is a, c, g, or t
<220> FEATURE:
<221> NAME/KEY: misc_feature
<222> LOCATION: (2362)..(2363)
<223> OTHER INFORMATION: n is a, c, g, or t
<220> FEATURE:
<221> NAME/KEY: misc_feature
<222> LOCATION: (2368)..(2368)
<223> OTHER INFORMATION: n is a, c, g, or t
<220> FEATURE:
<221> NAME/KEY: misc_feature
<222> LOCATION: (2372)..(2372)
<223> OTHER INFORMATION: n is a, c, g, or t
<220> FEATURE:
<221> NAME/KEY: misc_feature
<222> LOCATION: (2383)..(2386)
<223> OTHER INFORMATION: n is a, c, g, or t
<220> FEATURE:
<221> NAME/KEY: misc_feature
<222> LOCATION: (2396)..(2397)
<223> OTHER INFORMATION: n is a, c, g, or t
<220> FEATURE:
<221> NAME/KEY: misc_feature
<222> LOCATION: (2401)..(2402)
<223> OTHER INFORMATION: n is a, c, g, or t
<220> FEATURE:
<221> NAME/KEY: misc_feature
<222> LOCATION: (2415)..(2415)
<223> OTHER INFORMATION: n is a, c, g, or t
<220> FEATURE:
<221> NAME/KEY: misc_feature
<222> LOCATION: (2461)..(2461)
<223> OTHER INFORMATION: n is a, c, g, or t
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2513)..(2513)
<223> OTHER INFORMATION: n is a, c, g, or t
<220> FEATURE:
<221> NAME/KEY: misc_feature
<222> LOCATION: (2520)..(2520)
<223> OTHER INFORMATION: n is a, c, g, or t
<220> FEATURE:
<221> NAME/KEY: misc_feature
<222> LOCATION: (2522)..(2522)
<223> OTHER INFORMATION: n is a, c, g, or t
<220> FEATURE:
<221> NAME/KEY: misc_feature
<222> LOCATION: (2524)..(2524)
<223> OTHER INFORMATION: n is a, c, g, or t
```

<400> SEQUENCE: 32

```
ncgtnncgnt gcntctctca agnttagatt tntttnnncg taaanagagg aggancnatt      60
gctttaaanc ccaccaatta gctccttcac tctcagnnct naacaatggc ttcgactctg     120
ggcngcgatg ngagnnncga gatagtgttt ttcgatcttg agacngcngt tncgaccnaa     180
tcgggncagc cntttgcgat tttggagttt ggngctatct tagtttgccc tatgaagcta     240
gnggagctct atagttacnc cacnttggnt cgaccnacng atctttcnct catctncacg     300
ctcacgaagc gacgaagcgg cattacgcgc gacggagttc tctctgcacc tacnttctct     360
gaaatcgctg atgaantcta cganattcnc cacggtaagg gtttctcnnt tttttnnnn     420
nnctnncncn ntctctctna cncgaagnta naagtattga ttttggtgtt tctgtaggac     480
gaatttgggc nggacataac ataaagagat tcgattgtgt aagantanga gatgcatttg     540
cagnaattgg tntcnctccc cnngagncna aagntcaat tgatncactt tcgttntngt     600
ctcagaagtt tgggaagnga gctggngacn tgaaggtctc tctttttcg tcttcncgat     660
gataaatctc aaagccnata gcttccttgt tatcnttata gatatgaatt tcnangtaac     720
ttcaaagatt catcactcat canagtngct aaaatttacn ctnnnnnaan aangtagatg     780
gcntngcntg ctacntattt cgngctagga gancangctc acaggtaaaa nnagtaaacg     840
atacnntgtg cctttaacg attcnccagt tgtntcaata tgggactaaa catggntatg     900
attcancagg agcttagatg atgtccggat gaatcttgaa gtnntcaagn actgtncaac     960
cntcttnttt ctggtattgn tgtcttntca tttcttgaat aatgatnaac tcntaanttn    1020
aaaagganta gattanagng gttnngacat atctganttc tgtctncagt tntgnaaaag    1080
nnggntcnat cttccttnca gaccacaact ttgcaagccg taaacatggn ttgcaacttg    1140
caagtatagt ttgntatatc actgagttta agtacttggt gtttgcagga gtccagtgtt    1200
cctgacattc ttananncat gagctggttn tnccnaagaa aaagtcngag aacacgaagt    1260
aatgagaagt cactgccnaa tggagtcaga gaaagcccna cttcttcctc ttcnagccct    1320
aaanctgatc cgagttcgtc ttctgtanan gcnacanctg tcaaaaacca tcccatcatt    1380
tctcttctga cggaatgctc agaaanngat acatctagtt gngaaataga tccatcngac    1440
ataaccactc taataagtaa actacatatt ggaactctta aganagatgc tgcggacgaa    1500
gccaaaactg tgagagangc tgcgnangaa gccaaaantg taagcagca nggtgaatca    1560
accgatccca atgccaaaga tgaatcattt ttnggcgtta atgangtatc tntttctagn    1620
ntcagggcaa gtcttntncc gttatatcgt nggngtctga gaatggagct gnttcacaan    1680
ganaccctc tacatctcng ntggtatanc ntgaaaattc ggtttggaat aagncggaag    1740
tntgtggatc atgtaggtcg nccaaagatg aatattgtng tngacatacc tcctgattta    1800
tgcaagatct tggacgcatn nnatgctnct gcgcataact tactgattga ctcaagcaca    1860
anntcagann ggaggcctac ngttatgang aaanaaggct ttgccaacta tcccacngcc    1920
ngactgcagt aagtattcan cactctctct gnccttttac atacnagcat naatcnacng    1980
gagagtctct aanaccatct ccaacnctac tcnntnttca ccnccaaant ctattttgga    2040
gttaaatccc tccaanctt gcaaaatann natcttcaaa nntttctcc atatttggag    2100
attttgantt ttnaagtcat gactccattt tggagttggg tnggagaaaa acacaantcc    2160
aaaatagant tacttcattt tggngtaaaa aantgaagaa atgggttnga gatnnnctaa    2220
cctcnnntnan cantcntntn ttgttggnag aataagctcn gaatccaatn gaacccnggt    2280
anaccaaaaa gaagnacctt tgggaaccaa tcaaaagctc gatttcagta gcgataattt    2340
```

-continued

```
tgaaaagctn gagtcagcac tnnttccngg tnccctggtt gannnnttct tctcanncga    2400
nncttacgat tatangaaaa tggtagggat acgtctagca gccagaaagt tggtaatcca    2460
nctgaagaaa tgatctagcc aaggaaaaat cattcctctg tctcttnctg gtnagtcggn    2520 gngnactt                                                             2528
```

```
<210> SEQ ID NO 33
<211> LENGTH: 1521
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
```

-continued

```
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (374)..(375)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
```

```
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (528)..(529)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(605)
```

```
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
```

```
<222> LOCATION: (975)..(975)
<223> OTHER INFORMATION: n is a, c, g, or t
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (990)..(991)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
<222> LOCATION: (1081)..(1081)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1112)..(1112)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1190)..(1192)
<223> OTHER INFORMATION: n is a, c, g, or t
<220> FEATURE:
```

-continued

```
<221> NAME/KEY: misc_feature
<222> LOCATION: (1198)..(1198)
<223> OTHER INFORMATION: n is a, c, g, or t
<220> FEATURE:
<221> NAME/KEY: misc_feature
<222> LOCATION: (1232)..(1233)
<223> OTHER INFORMATION: n is a, c, g, or t
<220> FEATURE:
<221> NAME/KEY: misc_feature
<222> LOCATION: (1239)..(1240)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1259)..(1259)
<223> OTHER INFORMATION: n is a, c, g, or t
<220> FEATURE:
<221> NAME/KEY: misc_feature
<222> LOCATION: (1264)..(1264)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1291)..(1291)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1325)..(1325)
<223> OTHER INFORMATION: n is a, c, g, or t
<220> FEATURE:
<221> NAME/KEY: misc_feature
<222> LOCATION: (1330)..(1330)
<223> OTHER INFORMATION: n is a, c, g, or t
<220> FEATURE:
<221> NAME/KEY: misc_feature
<222> LOCATION: (1343)..(1343)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1410)..(1411)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1420)..(1420)
<223> OTHER INFORMATION: n is a, c, g, or t
<220> FEATURE:
<221> NAME/KEY: misc_feature
<222> LOCATION: (1431)..(1434)
<223> OTHER INFORMATION: n is a, c, g, or t
<220> FEATURE:
<221> NAME/KEY: misc_feature
<222> LOCATION: (1444)..(1445)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
```

```
<220> FEATURE:
<221> NAME/KEY: misc_feature
<222> LOCATION: (1463)..(1463)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t

<400> SEQUENCE: 33
atggcttcga ctctgggcng cgatgngagn nncgagatag tgttttcga tcttgagacn      60
gcngttncga ccnaatcggg ncagccnttt gcgattttgg agtttggngc tatcttagtt    120
tgccctatga agctagngga gctctatagt tacnccacnt tggntcgacc nacngatctt    180
tcnctcatct ncacgctcac gaagcgacga agcggcatta cgcgcgacgg agttctctct    240
gcacctacnt tctctgaaat cgctgatgaa ntctacgana ttcnccacgg acgaatttgg    300
gcnggacata acataaagag attcgattgt gtaagantan gagatgcatt tgcagnaatt    360
ggtntcnctc cccnngagnc naaagntnca attgatncac tttcgttntn gtctcagaag    420
tttgggaagn gagctggnga cntgaagatg gcntngcntg ctacntattt cgngctagga    480
gancangctc acaggagctt agatgatgtc cggatgaatc ttgaagtnnt caagnactgt    540
ncaaccntct tntttctgga gtccagtgtt cctgacattc ttananncat gagctggttn    600
tnccnaagaa aaagtcngag aacacgaagt aatgagaagt cactgccnaa tggagtcaga    660
gaaagcccna cttcttcctc ttcnagccct aaanctgatc cgagttcgtc ttctgtanan    720
gcnacanctg tcaaaaacca tcccatcatt tctcttctga cggaatgctc agaaanngat    780
acatctagtt gngaaataga tccatcngac ataaccactc taataagtaa actacatatt    840
ggaactctta aganagatgc tgcggacgaa gccaaaactg tgagagangc tgcgnangaa    900
gccaaaantg taagacagca nggtgaatca accgatccca atgccaaaga tgaatcattt    960
ttnggcgtta atgangtatc tnttttctagn ncagggcaa gtcttntncc gttatatcgt   1020
nggngtctga gaatggagct gnttcacaan ganaccccctc tacatctcng ntggtatanc   1080
ntgaaaattc ggtttggaat aagncggaag tntgtggatc atgtaggtcg nccaaagatg   1140
aatattgtng tngacatacc tcctgattta tgcaagatct tggacgcatn nnatgctnct   1200
gcgcataact tactgattga ctcaagcaca anntcagann ggaggcctac ngttatgang   1260
aaanaaggct ttgccaacta tcccacngcc ngactgcaaa taagctcnga atccaatnga   1320
acccnggtan accaaaaaga agnacctttg ggaaccaatc aaaagctcga tttcagtagc   1380
gataattttg aaaagctnga gtcagcactn nttccnggtn ccctggttga nnnnttcttc   1440
tcanncgann cttacgatta tangaaaatg gtagggatac gtctagcagc cagaaagttg   1500
gtaatccanc tgaagaaatg a                                             1521

<210> SEQ ID NO 34
<211> LENGTH: 2498
<212> TYPE: DNA
<213> ORGANISM: Boechera
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(9)
```

```
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (135)..(137)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
```

```
<222> LOCATION: (213)..(213)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (408)..(409)
<223> OTHER INFORMATION: n is a, c, g, or t
<220> FEATURE:
<221> NAME/KEY: misc_feature
<222> LOCATION: (417)..(422)
<223> OTHER INFORMATION: n is a, c, g, or t
<220> FEATURE:
<221> NAME/KEY: misc_feature
<222> LOCATION: (425)..(426)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
```

```
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (562)..(563)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
```

-continued

```
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (743)..(743)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t
<220> FEATURE:
<221> NAME/KEY: misc_feature
<222> LOCATION: (763)..(767)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (831)..(832)
<223> OTHER INFORMATION: n is a, c, g, or t
<220> FEATURE:
<221> NAME/KEY: misc_feature
<222> LOCATION: (845)..(846)
<223> OTHER INFORMATION: n is a, c, g, or t
<220> FEATURE:
<221> NAME/KEY: misc_feature
<222> LOCATION: (865)..(865)
```

```
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (943)..(944)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (962)..(962)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (1007)..(1007)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1044)..(1045)
<223> OTHER INFORMATION: n is a, c, g, or t
<220> FEATURE:
<221> NAME/KEY: misc_feature
<222> LOCATION: (1057)..(1057)
<223> OTHER INFORMATION: n is a, c, g, or t
<220> FEATURE:
<221> NAME/KEY: misc_feature
```

```
<222> LOCATION: (1066)..(1066)
<223> OTHER INFORMATION: n is a, c, g, or t
<220> FEATURE:
<221> NAME/KEY: misc_feature
<222> LOCATION: (1072)..(1072)
<223> OTHER INFORMATION: n is a, c, g, or t
<220> FEATURE:
<221> NAME/KEY: misc_feature
<222> LOCATION: (1075)..(1075)
<223> OTHER INFORMATION: n is a, c, g, or t
<220> FEATURE:
<221> NAME/KEY: misc_feature
<222> LOCATION: (1081)..(1082)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1088)..(1088)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1154)..(1154)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1216)..(1217)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1232)..(1232)
<223> OTHER INFORMATION: n is a, c, g, or t
<220> FEATURE:
<221> NAME/KEY: misc_feature
<222> LOCATION: (1235)..(1235)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t
<220> FEATURE:
<221> NAME/KEY: misc_feature
<222> LOCATION: (1324)..(1324)
<223> OTHER INFORMATION: n is a, c, g, or t
<220> FEATURE:
<221> NAME/KEY: misc_feature
<222> LOCATION: (1348)..(1348)
<223> OTHER INFORMATION: n is a, c, g, or t
<220> FEATURE:
```

```
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1357)..(1357)
<223> OTHER INFORMATION: n is a, c, g, or t
<220> FEATURE:
<221> NAME/KEY: misc_feature
<222> LOCATION: (1406)..(1407)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1484)..(1484)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1508)..(1508)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1563)..(1563)
<223> OTHER INFORMATION: n is a, c, g, or t
<220> FEATURE:
<221> NAME/KEY: misc_feature
<222> LOCATION: (1575)..(1575)
<223> OTHER INFORMATION: n is a, c, g, or t
<220> FEATURE:
<221> NAME/KEY: misc_feature
<222> LOCATION: (1582)..(1582)
<223> OTHER INFORMATION: n is a, c, g, or t
<220> FEATURE:
<221> NAME/KEY: misc_feature
<222> LOCATION: (1590)..(1591)
<223> OTHER INFORMATION: n is a, c, g, or t
<220> FEATURE:
<221> NAME/KEY: misc_feature
<222> LOCATION: (1606)..(1606)
<223> OTHER INFORMATION: n is a, c, g, or t
<220> FEATURE:
<221> NAME/KEY: misc_feature
<222> LOCATION: (1608)..(1608)
<223> OTHER INFORMATION: n is a, c, g, or t
<220> FEATURE:
<221> NAME/KEY: misc_feature
<222> LOCATION: (1621)..(1621)
<223> OTHER INFORMATION: n is a, c, g, or t
<220> FEATURE:
<221> NAME/KEY: misc_feature
<222> LOCATION: (1624)..(1624)
<223> OTHER INFORMATION: n is a, c, g, or t
```

-continued

```
<220> FEATURE:
<221> NAME/KEY: misc_feature
<222> LOCATION: (1642)..(1642)
<223> OTHER INFORMATION: n is a, c, g, or t
<220> FEATURE:
<221> NAME/KEY: misc_feature
<222> LOCATION: (1650)..(1650)
<223> OTHER INFORMATION: n is a, c, g, or t
<220> FEATURE:
<221> NAME/KEY: misc_feature
<222> LOCATION: (1653)..(1653)
<223> OTHER INFORMATION: n is a, c, g, or t
<220> FEATURE:
<221> NAME/KEY: misc_feature
<222> LOCATION: (1669)..(1669)
<223> OTHER INFORMATION: n is a, c, g, or t
<220> FEATURE:
<221> NAME/KEY: misc_feature
<222> LOCATION: (1671)..(1671)
<223> OTHER INFORMATION: n is a, c, g, or t
<220> FEATURE:
<221> NAME/KEY: misc_feature
<222> LOCATION: (1679)..(1679)
<223> OTHER INFORMATION: n is a, c, g, or t
<220> FEATURE:
<221> NAME/KEY: misc_feature
<222> LOCATION: (1681)..(1681)
<223> OTHER INFORMATION: n is a, c, g, or t
<220> FEATURE:
<221> NAME/KEY: misc_feature
<222> LOCATION: (1704)..(1704)
<223> OTHER INFORMATION: n is a, c, g, or t
<220> FEATURE:
<221> NAME/KEY: misc_feature
<222> LOCATION: (1712)..(1712)
<223> OTHER INFORMATION: n is a, c, g, or t
<220> FEATURE:
<221> NAME/KEY: misc_feature
<222> LOCATION: (1731)..(1731)
<223> OTHER INFORMATION: n is a, c, g, or t
<220> FEATURE:
<221> NAME/KEY: misc_feature
<222> LOCATION: (1749)..(1749)
<223> OTHER INFORMATION: n is a, c, g, or t
<220> FEATURE:
<221> NAME/KEY: misc_feature
<222> LOCATION: (1752)..(1752)
<223> OTHER INFORMATION: n is a, c, g, or t
<220> FEATURE:
<221> NAME/KEY: misc_feature
<222> LOCATION: (1790)..(1792)
<223> OTHER INFORMATION: n is a, c, g, or t
<220> FEATURE:
<221> NAME/KEY: misc_feature
<222> LOCATION: (1798)..(1798)
<223> OTHER INFORMATION: n is a, c, g, or t
<220> FEATURE:
<221> NAME/KEY: misc_feature
<222> LOCATION: (1832)..(1833)
<223> OTHER INFORMATION: n is a, c, g, or t
<220> FEATURE:
<221> NAME/KEY: misc_feature
<222> LOCATION: (1839)..(1840)
<223> OTHER INFORMATION: n is a, c, g, or t
<220> FEATURE:
<221> NAME/KEY: misc_feature
<222> LOCATION: (1851)..(1851)
<223> OTHER INFORMATION: n is a, c, g, or t
<220> FEATURE:
<221> NAME/KEY: misc_feature
<222> LOCATION: (1859)..(1859)
<223> OTHER INFORMATION: n is a, c, g, or t
<220> FEATURE:
<221> NAME/KEY: misc_feature
<222> LOCATION: (1864)..(1864)
<223> OTHER INFORMATION: n is a, c, g, or t
<220> FEATURE:
<221> NAME/KEY: misc_feature
<222> LOCATION: (1887)..(1887)
```

```
<223> OTHER INFORMATION: n is a, c, g, or t
<220> FEATURE:
<221> NAME/KEY: misc_feature
<222> LOCATION: (1891)..(1891)
<223> OTHER INFORMATION: n is a, c, g, or t
<220> FEATURE:
<221> NAME/KEY: misc_feature
<222> LOCATION: (1910)..(1910)
<223> OTHER INFORMATION: n is a, c, g, or t
<220> FEATURE:
<221> NAME/KEY: misc_feature
<222> LOCATION: (1922)..(1922)
<223> OTHER INFORMATION: n is a, c, g, or t
<220> FEATURE:
<221> NAME/KEY: misc_feature
<222> LOCATION: (1935)..(1935)
<223> OTHER INFORMATION: n is a, c, g, or t
<220> FEATURE:
<221> NAME/KEY: misc_feature
<222> LOCATION: (1941)..(1941)
<223> OTHER INFORMATION: n is a, c, g, or t
<220> FEATURE:
<221> NAME/KEY: misc_feature
<222> LOCATION: (1946)..(1946)
<223> OTHER INFORMATION: n is a, c, g, or t
<220> FEATURE:
<221> NAME/KEY: misc_feature
<222> LOCATION: (1949)..(1949)
<223> OTHER INFORMATION: n is a, c, g, or t
<220> FEATURE:
<221> NAME/KEY: misc_feature
<222> LOCATION: (1963)..(1963)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (1983)..(1984)
<223> OTHER INFORMATION: n is a, c, g, or t
<220> FEATURE:
<221> NAME/KEY: misc_feature
<222> LOCATION: (1986)..(1986)
<223> OTHER INFORMATION: n is a, c, g, or t
<220> FEATURE:
<221> NAME/KEY: misc_feature
<222> LOCATION: (1993)..(1993)
<223> OTHER INFORMATION: n is a, c, g, or t
<220> FEATURE:
<221> NAME/KEY: misc_feature
<222> LOCATION: (1999)..(1999)
<223> OTHER INFORMATION: n is a, c, g, or t
<220> FEATURE:
<221> NAME/KEY: misc_feature
<222> LOCATION: (2026)..(2027)
<223> OTHER INFORMATION: n is a, c, g, or t
<220> FEATURE:
<221> NAME/KEY: misc_feature
<222> LOCATION: (2039)..(2041)
<223> OTHER INFORMATION: n is a, c, g, or t
<220> FEATURE:
<221> NAME/KEY: misc_feature
<222> LOCATION: (2051)..(2052)
<223> OTHER INFORMATION: n is a, c, g, or t
<220> FEATURE:
<221> NAME/KEY: misc_feature
<222> LOCATION: (2078)..(2078)
<223> OTHER INFORMATION: n is a, c, g, or t
<220> FEATURE:
<221> NAME/KEY: misc_feature
<222> LOCATION: (2083)..(2083)
<223> OTHER INFORMATION: n is a, c, g, or t
<220> FEATURE:
<221> NAME/KEY: misc_feature
<222> LOCATION: (2112)..(2112)
<223> OTHER INFORMATION: n is a, c, g, or t
<220> FEATURE:
<221> NAME/KEY: misc_feature
```

```
<222> LOCATION: (2127)..(2127)
<223> OTHER INFORMATION: n is a, c, g, or t
<220> FEATURE:
<221> NAME/KEY: misc_feature
<222> LOCATION: (2139)..(2139)
<223> OTHER INFORMATION: n is a, c, g, or t
<220> FEATURE:
<221> NAME/KEY: misc_feature
<222> LOCATION: (2154)..(2154)
<223> OTHER INFORMATION: n is a, c, g, or t
<220> FEATURE:
<221> NAME/KEY: misc_feature
<222> LOCATION: (2163)..(2163)
<223> OTHER INFORMATION: n is a, c, g, or t
<220> FEATURE:
<221> NAME/KEY: misc_feature
<222> LOCATION: (2178)..(2178)
<223> OTHER INFORMATION: n is a, c, g, or t
<220> FEATURE:
<221> NAME/KEY: misc_feature
<222> LOCATION: (2184)..(2186)
<223> OTHER INFORMATION: n is a, c, g, or t
<220> FEATURE:
<221> NAME/KEY: misc_feature
<222> LOCATION: (2195)..(2196)
<223> OTHER INFORMATION: n is a, c, g, or t
<220> FEATURE:
<221> NAME/KEY: misc_feature
<222> LOCATION: (2198)..(2198)
<223> OTHER INFORMATION: n is a, c, g, or t
<220> FEATURE:
<221> NAME/KEY: misc_feature
<222> LOCATION: (2200)..(2200)
<223> OTHER INFORMATION: n is a, c, g, or t
<220> FEATURE:
<221> NAME/KEY: misc_feature
<222> LOCATION: (2203)..(2203)
<223> OTHER INFORMATION: n is a, c, g, or t
<220> FEATURE:
<221> NAME/KEY: misc_feature
<222> LOCATION: (2206)..(2206)
<223> OTHER INFORMATION: n is a, c, g, or t
<220> FEATURE:
<221> NAME/KEY: misc_feature
<222> LOCATION: (2208)..(2208)
<223> OTHER INFORMATION: n is a, c, g, or t
<220> FEATURE:
<221> NAME/KEY: misc_feature
<222> LOCATION: (2210)..(2210)
<223> OTHER INFORMATION: n is a, c, g, or t
<220> FEATURE:
<221> NAME/KEY: misc_feature
<222> LOCATION: (2218)..(2218)
<223> OTHER INFORMATION: n is a, c, g, or t
<220> FEATURE:
<221> NAME/KEY: misc_feature
<222> LOCATION: (2230)..(2230)
<223> OTHER INFORMATION: n is a, c, g, or t
<220> FEATURE:
<221> NAME/KEY: misc_feature
<222> LOCATION: (2240)..(2240)
<223> OTHER INFORMATION: n is a, c, g, or t
<220> FEATURE:
<221> NAME/KEY: misc_feature
<222> LOCATION: (2247)..(2247)
<223> OTHER INFORMATION: n is a, c, g, or t
<220> FEATURE:
<221> NAME/KEY: misc_feature
<222> LOCATION: (2252)..(2252)
<223> OTHER INFORMATION: n is a, c, g, or t
<220> FEATURE:
<221> NAME/KEY: misc_feature
<222> LOCATION: (2265)..(2265)
<223> OTHER INFORMATION: n is a, c, g, or t
<220> FEATURE:
<221> NAME/KEY: misc_feature
<222> LOCATION: (2320)..(2320)
<223> OTHER INFORMATION: n is a, c, g, or t
<220> FEATURE:
```

```
<221> NAME/KEY: misc_feature
<222> LOCATION: (2332)..(2333)
<223> OTHER INFORMATION: n is a, c, g, or t
<220> FEATURE:
<221> NAME/KEY: misc_feature
<222> LOCATION: (2338)..(2338)
<223> OTHER INFORMATION: n is a, c, g, or t
<220> FEATURE:
<221> NAME/KEY: misc_feature
<222> LOCATION: (2342)..(2342)
<223> OTHER INFORMATION: n is a, c, g, or t
<220> FEATURE:
<221> NAME/KEY: misc_feature
<222> LOCATION: (2353)..(2356)
<223> OTHER INFORMATION: n is a, c, g, or t
<220> FEATURE:
<221> NAME/KEY: misc_feature
<222> LOCATION: (2366)..(2367)
<223> OTHER INFORMATION: n is a, c, g, or t
<220> FEATURE:
<221> NAME/KEY: misc_feature
<222> LOCATION: (2371)..(2372)
<223> OTHER INFORMATION: n is a, c, g, or t
<220> FEATURE:
<221> NAME/KEY: misc_feature
<222> LOCATION: (2385)..(2385)
<223> OTHER INFORMATION: n is a, c, g, or t
<220> FEATURE:
<221> NAME/KEY: misc_feature
<222> LOCATION: (2431)..(2431)
<223> OTHER INFORMATION: n is a, c, g, or t
<220> FEATURE:
<221> NAME/KEY: misc_feature
<222> LOCATION: (2477)..(2477)
<223> OTHER INFORMATION: n is a, c, g, or t
<220> FEATURE:
<221> NAME/KEY: misc_feature
<222> LOCATION: (2483)..(2483)
<223> OTHER INFORMATION: n is a, c, g, or t
<220> FEATURE:
<221> NAME/KEY: misc_feature
<222> LOCATION: (2490)..(2490)
<223> OTHER INFORMATION: n is a, c, g, or t
<220> FEATURE:
<221> NAME/KEY: misc_feature
<222> LOCATION: (2492)..(2492)
<223> OTHER INFORMATION: n is a, c, g, or t
<220> FEATURE:
<221> NAME/KEY: misc_feature
<222> LOCATION: (2494)..(2494)
<223> OTHER INFORMATION: n is a, c, g, or t

<400> SEQUENCE: 34
ncgtnncgnt gcntctctca agnttagatt tntttnnncg taaanagagg aggancnatt      60
gctttaaanc ccaccaatta gctccttcac tctcagnnct naacaatggc ttcgactctg     120
ggcngcgatg ngagnnncga gatagtgttt ttcgatcttg agacngcngt tncgaccnaa     180
tcgggncagc cntttgcgat tttggagttt ggngctatct tagtttgccc tatgaagcta     240
gnggagctct atagttacnc cacnttggnt cgaccnacng atctttcnct catctncacg     300
ctcacgaagc gacgaagcgg cattacgcgc gacggagttc tctctgcacc tacnttctct     360
gaaatcgctg atgaantcta cganattcnc cacggtaagg gtttctcnnt tttttttnnnn    420 nnctnncncn ntctctctna cncgaagnta naagtattga ttttggtgtt tctgtaggac     480
gaatttgggc nggacataac ataaagagat tcgattgtgt aagantanga gatgcatttg     540
cagnaattgg tntcnctccc cnngagncna agntncaat tgatncactt tcgttntngt      600
ctcagaagtt tgggaagnga gctggngacn tgaaggtctc tctttttcg tcttcncgat      660 gataaatctc aaagccnata gcttccttgt tatcnttata gatatgaatt tcnangtaac     720
ttcaaagatt catcactcat canagtngct aaaatttacn ctnnnnnaan aangtagatg     780
```

```
gcntngcntg ctacntattt cgngctagga gancangctc acaggtaaaa nnagtaaacg    840
atacnntgtg cctttttaacg attcnccagt tgtntcaata tgggactaaa catggntatg    900
attcancagg agcttagatg atgtccggat gaatcttgaa gtnntcaagn actgtncaac    960
cntcttnttt ctggtattgn tgtcttntca tttcttgaat aatgatnaac tcntaanttn   1020
aaaagganta gattanagng gttnngacat atctganttc tgtctncagt tntgnaaaag   1080
nnggntcnat cttccttnca gaccacaact ttgcaagccg taaacatggn ttgcaacttg   1140
caagtatagt ttgntatatc actgagttta agtacttggt gtttgcagga gtccagtgtt   1200
cctgacattc ttananncat gagctggttn tnccnaagaa aaagtcngag aacacgaagt   1260
aatgagaagt cactgccnaa tggagtcaga gaaagcccna cttcttcctc ttcnagccct   1320
aaanctgatc cgagttcgtc ttctgtanan gcnacanctg tcaaaaacca tcccatcatt   1380
tctcttctga cggaatgctc agaaanngat acatctagtt gngaaataga tccatcngac   1440
ataaccactc taataagtaa actacatatt ggaactctta aganagangc tgcgnangaa   1500
gccaaaantg taagacagca nggtgaatca accgatccca atgccaaaga tgaatcattt   1560
ttnggcgtta atgangtatc tntttctagn ntcagggcaa gtcttntncc gttatatcgt   1620
nggngtctga gaatggagct gnttcacaan ganacccctc tacatctcng ntggtatanc   1680
ntgaaaattc ggtttggaat aagncggaag tntgtggatc atgtaggtcg nccaaagatg   1740
aatattgtng tngacatacc tcctgattta tgcaagatct tggacgcatn nnatgctnct   1800
gcgcataact tactgattga ctcaagcaca anntcagann ggaggcctac ngttatgang   1860
aaanaaggct ttgccaacta tcccacngcc ngactgcagt aagtattcan cactctctct   1920
gnccttttac atacnagcat naatcnacng gagagtctct aanaccatct ccaacnctac   1980
tcnntnttca ccnccaaant ctattttgga gttaaatccc tccaannctt gcaaaatann   2040
natcttcaaa nnttttctcc atatttggag attttgantt ttnaagtcat gactccattt   2100
tggagttggg tnggagaaaa acacaantcc aaaatagant tacttcattt tggngtaaaa   2160
aantgaagaa atgggttnga gatnnnctaa cctcnntnan cantcntntn ttgttggnag   2220
aataagctcn gaatccaatn gaacccnggt anaccaaaaa gaagnacctt tgggaaccaa   2280
tcaaaagctc gatttcagta gcgataattt tgaaaagctn gagtcagcac tnnttccngg   2340
tnccctggtt gannnnttct tctcanncga nncttacgat tatangaaaa tggtagggat   2400
acgtctagca gccagaaagt tggtaatcca nctgaagaaa tgatctagcc aaggaaaaat   2460
cattcctctg tctcttnctg gtnagtcggn gngnactt                          2498
```

<210> SEQ ID NO 35
<211> LENGTH: 1491
<212> TYPE: DNA
<213> ORGANISM: Boechera
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (60)..(60)

```
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
```

```
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (374)..(375)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
```

-continued

```
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (528)..(529)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
```

-continued

```
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (776)..(777)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (960)..(961)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1012)..(1012)
```

-continued

```
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1049)..(1049)
<223> OTHER INFORMATION: n is a, c, g, or t
<220> FEATURE:
<221> NAME/KEY: misc_feature
<222> LOCATION: (1051)..(1051)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1082)..(1082)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1160)..(1162)
<223> OTHER INFORMATION: n is a, c, g, or t
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (1202)..(1203)
<223> OTHER INFORMATION: n is a, c, g, or t
<220> FEATURE:
<221> NAME/KEY: misc_feature
<222> LOCATION: (1209)..(1210)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1234)..(1234)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
```

```
<222> LOCATION: (1261)..(1261)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t
<220> FEATURE:
<221> NAME/KEY: misc_feature
<222> LOCATION: (1313)..(1313)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1380)..(1381)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1390)..(1390)
<223> OTHER INFORMATION: n is a, c, g, or t
<220> FEATURE:
<221> NAME/KEY: misc_feature
<222> LOCATION: (1401)..(1404)
<223> OTHER INFORMATION: n is a, c, g, or t
<220> FEATURE:
<221> NAME/KEY: misc_feature
<222> LOCATION: (1414)..(1415)
<223> OTHER INFORMATION: n is a, c, g, or t
<220> FEATURE:
<221> NAME/KEY: misc_feature
<222> LOCATION: (1419)..(1420)
<223> OTHER INFORMATION: n is a, c, g, or t
<220> FEATURE:
<221> NAME/KEY: misc_feature
<222> LOCATION: (1433)..(1433)
<223> OTHER INFORMATION: n is a, c, g, or t
<220> FEATURE:
<221> NAME/KEY: misc_feature
<222> LOCATION: (1479)..(1479)
<223> OTHER INFORMATION: n is a, c, g, or t

<400> SEQUENCE: 35
atggcttcga ctctgggcng cgatgngagn nncgagatag tgttttcga tcttgagacn      60 gcngttncga ccnaatcggg ncagccnttt gcgattttgg agtttggngc tatcttagtt    120
tgccctatga agctagngga gctctatagt tacnccacnt tggntcgacc nacngatctt    180
tcnctcatct ncacgctcac gaagcgacga agcggcatta cgcgcgacgg agttctctct    240
gcacctacnt tctctgaaat cgctgatgaa ntctacgana ttcnccacgg acgaatttgg    300
gcnggacata acataaagag attcgattgt gtaagantan gagatgcatt tgcagnaatt    360
ggtntcnctc cccnngagnc naaagntnca attgatncac tttcgttntn gtctcagaag    420
tttgggaagn gagctggnga cntgaagatg gcntngcntg ctacntattt cgngctagga    480
gancangctc acaggagctt agatgatgtc cggatgaatc ttgaagtnnt caagnactgt    540
```

-continued

```
ncaaccntct tntttctgga gtccagtgtt cctgacattc ttananncat gagctggttn    600
tnccnaagaa aaagtcngag aacacgaagt aatgagaagt cactgccnaa tggagtcaga    660
gaaagcccna cttcttcctc ttcnagccct aaanctgatc cgagttcgtc ttctgtanan    720
gcnacanctg tcaaaaacca tcccatcatt tctcttctga cggaatgctc agaaanngat    780
acatctagtt gngaaataga tccatcngac ataaccactc taataagtaa actacatatt    840
ggaactctta aganagangc tgcgnangaa gccaaaantg taagcagca nggtgaatca     900 accgatccca atgccaaaga tgaatcattt ttnggcgtta atgangtatc tntttctagn    960
ntcagggcaa gtcttntncc gttatatcgt nggngtctga gaatggagct gnttcacaan   1020 ganaccctc tacatctcng ntggtatanc ntgaaaattc ggtttggaat aagncggaag    1080
tntgtggatc atgtaggtcg nccaaagatg aatattgtng tngacatacc tcctgattta   1140
tgcaagatct tggacgcatn nnatgctnct gcgcataact tactgattga ctcaagcaca   1200
anntcagann ggaggcctac ngttatgang aaanaaggct ttgccaacta tcccacngcc   1260
ngactgcaaa taagctcnga atccaatnga acccnggtan accaaaaaga agnacctttg   1320
ggaaccaatc aaaagctcga tttcagtagc gataattttg aaaagctnga gtcagcactn   1380
nttccnggtn ccctggttga nnnnttcttc tcanncgann cttacgatta tangaaaatg   1440
gtagggatac gtctagcagc cagaaagttg gtaatccanc tgaagaaatg a            1491
```

<210> SEQ ID NO 36
<211> LENGTH: 495
<212> TYPE: DNA
<213> ORGANISM: Boechera
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature

```
<222> LOCATION: (125)..(125)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (335)..(336)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
```

<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (489)..(490)
<223> OTHER INFORMATION: n is a, c, g, or t

<400> SEQUENCE: 36

```
gtgttttcg atcttgagac ngcngttncg accnaatcgg gncagccntt tgcgattttg      60
gagtttggng ctatcttagt ttgccctatg aagctagngg agctctatag ttacnccacn    120
ttggntcgac cnacngatct ttcnctcatc tncacgctca cgaagcgacg aagcggcatt    180
acgcgcgacg gagttctctc tgcacctacn ttctctgaaa tcgctgatga antctacgan    240
attcnccacg gacgaatttg ggcnggacat aacataaaga gattcgattg tgtaaganta    300
ngagatgcat ttgcagnaat tggtntcnct ccccnngagn cnaaagntnc aattgatnca    360
ctttcgttnt ngtctcagaa gtttgggaag ngagctggng acntgaagat ggcntngcnt    420
gctacntatt tcgngctagg agancangct cacaggagct tagatgatgt ccggatgaat    480
cttgaagtnn tcaag                                                     495
```

<210> SEQ ID NO 37
<211> LENGTH: 2483

<212> TYPE: DNA
<213> ORGANISM: Boechera

<400> SEQUENCE: 37

```
tcgtaccgtt gcttctctca agtttagatt ttttccgta aaaagaggag gtggcccgtg     60
aagtttattc cctttaaaac ccaccaatta gctccttcac tctcagttct caacaatggc    120
ttcgactctg ggcggcgatg agagaaacga gatagtgttt ttcgatcttg agactgcggt    180
tccgaccaaa tcgggcagc cttttgcgat tttggagttt ggggctatct tagtttgccc     240
tatgaagcta gtggagctct atagttactc cactttggtt cgacctaccg atctttctct    300
catctccacg ctcacgaagc gacgaagcgg cattacgcgc gacggagttc tctctgcacc    360
tacattctct gaaatcgctg atgaagtcta cgacattctc cacggtaagg gtttctcttt    420
ttttttttct ttctcaatct ctctcacgcg aagctacaag tattgatttt ggtgtttctg    480
taggacgaat ttgggtggga cataacataa agagattcga ttgtgtaaga ataagagatg    540
catttgcaga aattggtctc cctccccgg agccgaaagc tacaattgat tcactttcgt     600
tgttgtctca gaagtttggg aagagagctg gtgacatgaa ggtctctctt ttttcgtctt    660
ctcgatgata aatctcaaag cctatagctt ccttgttatc tttatagata tgaatttcaa    720
tgtaacttca aagattcatc actcatcaaa gttgctaaaa tttactctaa ataatgtaga    780
tggcatcgca tgctacatat ttcgggctag gagatcaagc tcacaggtaa aagagtaaac    840
gataccctgt gccttttaac gattcaccag ttgtttcaat atgggactaa acatggatat    900
gattcaccag gagcttagat gatgtccgga tgaatcttga agttatcaag cactgttcaa    960
ccgtcttgtt tctggtattg ttgtcttctc atttcttgaa taatgattaa ctctaactta   1020
aaaggattag attaaagagg ttgagacata tctgacttct gtctacagtt tgcaaaagtt   1080
gggtccatct tccttccaga ccacaacttt gcaagccgta acatggtttt gcaagtatag   1140
tttgtcatat cactgagttt aagtacttgg tgtttgcagg agtccagtgt tcctgacatt   1200
cttacagaca tgagctggtt attcccaaga aaaagtccga gaacacgaag taatgagaag   1260
tcactgccta atggagtcag agaaagcccg acttcttcct cttcgagccc taaaactgat   1320
ccgagttcgt cttctgtaga tgccacagct gtcaaaaacc atcccatcat ttctcttctg   1380
acggaatgct cagaaagtga tacatctagt tgtgaaatag atccatctga cataaccact   1440
ctaataagta aactacatat tggaactctt aagacagatg ctgcggacga agccaaaact   1500
gtaagacagc agggtgaatc aaccgatccc aatgccaaag atgaatcatt tttgggcgtt   1560
aatgaagtat ctgtttctag catcagggca agtcttatcc cgttatatcg taggagtctg   1620
agaatggagc tgtttcacaa cgacacccct ctacatctct gttggtatag cttgaaaatt   1680
cggtttggaa taagccggaa gtatgtggat catgtaggtc gtccaaagat gaatattgtt   1740
gtagacatac ctcctgattt atgcaagatc ttggacgcat ccgatgctgc tgcgcataac   1800
ttactgattg actcaagcac aagctcagat tggaggccta ccgttatgag gaaaaaggc   1860
tttgccaact atcccacagc cagactgcag taagtattca acactctctc tgacctttta   1920
catacgagca tgaatccacc ggagagtctc taagaccatc tccaacccta ctctattcac   1980
ctccaaactc tattttggag ttaaatccct ccaaccttg caaatagac atcttcaaaa     2040
ttttctccat atttggagat tttgattttt aagtcatga ctccattttg gagttgggtt    2100
ggagaaaaac acaactccaa aatagattta cttcattttg gagtaaaaaa tgaagaaatg   2160
ggttggagat actaacctct gtcaccattc ttatgttgtt ggcagaataa gctcagaatc   2220
```

| | |
|---|---:|
| caatggaacc caggtacacc aaaaagaaga acctttggga accaatcaaa agctcgattt | 2280 |
| cagtagcgat aattttgaaa agcttgagtc agcacttctt cctggtaccc tggttgatgc | 2340 |
| attcttctca ctcgagcctt acgattataa gaaaatggta gggatacgtc tagcagccag | 2400 |
| aaagttggta atccacctga agaaatgatc tagccaagga aaaatcattc ctctgtctct | 2460 |
| tcctggtcag tcggtgagca ctt | 2483 |

<210> SEQ ID NO 38
<211> LENGTH: 1491
<212> TYPE: DNA
<213> ORGANISM: Boechera

<400> SEQUENCE: 38

| | |
|---|---:|
| atggcttcga ctctgggcgg cgatgagaga aacgagatag tgttttttcga tcttgagact | 60 |
| gcggttccga ccaaatcggg gcagcctttt gcgattttgg agtttggggc tatcttagtt | 120 |
| tgccctatga agctagtgga gctctatagt tactccactt tggttcgacc taccgatctt | 180 |
| tctctcatct ccacgctcac gaagcgacga agcggcatta cgcgcgacgg agttctctct | 240 |
| gcacctacat tctctgaaat cgctgatgaa gtctacgaca ttctccacgg acgaatttgg | 300 |
| gtgggacata acataaagag attcgattgt gtaagaataa gagatgcatt tgcagaaatt | 360 |
| ggtctccctc ccccggagcc gaaagctaca attgattcac tttcgttgtt gtctcagaag | 420 |
| tttgggaaga gagctggtga catgaagatg gcatcgcatg ctacatattt cgggctagga | 480 |
| gatcaagctc acaggagctt agatgatgtc cggatgaatc ttgaagttat caagcactgt | 540 |
| tcaaccgtct tgtttctgga gtccagtgtt cctgacattc ttacagacat gagctggtta | 600 |
| ttcccaagaa aaagtccgag aacacgaagt aatgagaagt cactgcctaa tggagtcaga | 660 |
| gaaagcccga cttcttcctc ttcgagcccct aaaactgatc cgagttcgtc ttctgtagat | 720 |
| gccacagctg tcaaaaacca tcccatcatt tctcttctga cggaatgctc agaaagtgat | 780 |
| acatctagtt gtgaaataga tccatctgac ataaccactc taataagtaa actacatatt | 840 |
| ggaactctta agacagatgc tgcggacgaa gccaaaactg taagacagca gggtgaatca | 900 |
| accgatccca tgccaaaga tgaatcattt ttgggcgtta atgaagtatc tgtttctagc | 960 |
| atcagggcaa gtcttatccc gttatatcgt aggagtctga aatggagct gtttcacaac | 1020 |
| gacacccctc tacatctctg ttggtatagc ttgaaaattc ggtttggaat aagccggaag | 1080 |
| tatgtggatc atgtaggtcg tccaaagatg aatattgttg tagacatacc tcctgattta | 1140 |
| tgcaagatct tggacgcatc cgatgctgct gcgcataact tactgattga ctcaagcaca | 1200 |
| agctcagatt ggaggcctac cgttatgagg aaaaaaggct ttgccaacta tcccacagcc | 1260 |
| agactgcaaa taagctcaga atccaatgga acccaggtac accaaaaaga gaacctttg | 1320 |
| ggaaccaatc aaaagctcga tttcagtagc gataattttg aaaagcttga gtcagcactt | 1380 |
| cttcctggta ccctggttga tgcattcttc tcactcgagc cttacgatta taagaaaatg | 1440 |
| gtagggatac gtctagcagc cagaaagttg gtaatccacc tgaagaaatg a | 1491 |

<210> SEQ ID NO 39
<211> LENGTH: 495
<212> TYPE: DNA
<213> ORGANISM: Boechera

<400> SEQUENCE: 39

| | |
|---|---:|
| gtgttttttcg atcttgagac tgcggttccg accaaatcgg ggcagccttt tgcgattttg | 60 |
| gagtttgggg ctatcttagt ttgccctatg aagctagtgg agctctatag ttactccact | 120 |

```
ttggttcgac ctaccgatct ttctctcatc tccacgctca cgaagcgacg aagcggcatt      180
acgcgcgacg gagttctctc tgcacctaca ttctctgaaa tcgctgatga agtctacgac      240
attctccacg gacgaatttg ggtgggacat aacataaaga gattcgattg tgtaagaata      300
agagatgcat ttgcagaaat tggtctccct cccccggagc cgaaagctac aattgattca      360
ctttcgttgt tgtctcagaa gtttgggaag agagctggtg acatgaagat ggcatcgcat      420
gctacatatt tcgggctagg agatcaagct cacaggagct tagatgatgt ccggatgaat      480
cttgaagtta tcaag                                                       495
```

<210> SEQ ID NO 40
<211> LENGTH: 2483
<212> TYPE: DNA
<213> ORGANISM: Boechera

<400> SEQUENCE: 40

```
tcgtaccgtt gcttctctca agtttagatt tttttccgta aaaagaggag gtggcccgtg       60
aagtttattc cctttaaaac ccaccaatta gctccttcac tctcagttct caacaatggc      120
ttcgactctg gcggcgatg agagaaacga gatagtgttt ttcgatcttg agactgcggt       180
tccgaccaaa tcggggcagc cttttgcgat tttggagttt ggggctatct tagtttgccc      240
tatgaagcta gtggagctct atagttactc cactttggtt cgacctaccg atctttctct      300
catctccacg ctcacgaagc gacgaagcgg cattacgcgc gacggagttc tctctgcacc      360
tacattctct gaaatcgctg atgaagtcta cgacattctc cacggtaagg gtttctcttt      420
tttttttctt tctcaatctc tctcacgcga agctacaagt attgattttg gtgtttctgt      480
aggacgaatt tgggcgggac ataacataaa gagattcgat tgtgtaagaa taagagatgc      540
atttgcagaa attggtctcc ctcccccgga gccgaaagct acaattgatt cactttcgtt      600
gttgtctcag aagtttggga gagagctggt gacatgaag gtctctcttt tttcgtcttc      660
tcgatgataa atctcaaagc ctatagcttc cttgttatct ttatagatat gaatttcaat      720
gtaacttcaa agattcatca ctcatcaaag ttgctaaaat ttactctaaa taatgtagat      780
ggcatcgctt gctacatatt tcgggctagg agatcaagct cacaggtaaa agagtaaacg      840
ataccctgtg cctttaaacg attccaccagt tgtttcaata tgggactaaa catggatatg      900
attcaccagg agcttagatg atgtccggat gaatcttgaa gttatcaagc actgttcaac      960
cgtcttgttt ctggtattgt tgtcttctca tttcttgaat aatgattaac tctaatttaa     1020
aaggattaga ttaaagaggt tgagacatat ctgacttctg tctacagttt gcaaaagttg     1080
ggtccatctt ccttccagac cacagctttg caagccgtaa acatggtttg caagtatagt     1140
ttgtcatatc actgagttta agtacttggt gtttgcagga gtccagtgtt cctgacattc     1200
ttacagacat gagctggtta ttcccaagaa aaagtccgag aacacgaagt aatgagaagt     1260
cactgcctaa tggagtcaga gaaagcccga cttcttcctc ttcgagccct caaactgatc     1320
cgagttcgtc ttctgtagat gccacagctg tcaaaaacca tcccatcatt tctcttctga     1380
cggaatgctc agaaagtgat acatctagtt gtgaaataga tccatctgac ataaccactc     1440
taataagtaa actacatatt ggaactctta agacagatgc tgcggacgaa gccaaaactg     1500
taagacagca gggtgaatca accgatccca atgccaaaga tgaatcattt ttgggcgtta     1560
atgaagtatc tgtttctagc atcagggcaa gtcttatccc gttatatcgt aggagtctga     1620
gaatggagct gtttcacaac gacaccccctc tacatctctg ttggtatagc ttgaaaattc     1680
```

| | |
|---|---:|
| ggtttggaat aagccggaag tatgtggatc atgtaggtcg tccaaagatg aatattgttg | 1740 |
| tagacatacc tcctgattta tgcaagatct tggacgcatc cgatgctgct gcgcataact | 1800 |
| tactgattga ctcaagcaca agctcagatt ggaggcctac cgttatgagg aaaaaaggct | 1860 |
| ttgccaacta tcccacagcc agactgcagt aagtattcaa cactctctct gaccttttac | 1920 |
| atacgagcat gaatccaccg gagagtctct aagaccatct ccaaccctac tctattcacc | 1980 |
| tccaaactct attttggagt taaatccctc caacccttgc aaaatagaga tcttcaaatt | 2040 |
| tttctccata tttggagatt ttgattttta agtcatgact ccattttgga gttgggttgg | 2100 |
| agaaaaacac aattccaaaa tagagttact tcatttttgga gtaaaaaatg aagaaatggg | 2160 |
| ttcgagatgc tctaacctct gtcaccattc ttatcttgtt ggcagaataa gctcagaatc | 2220 |
| caatggaacc caggtatacc aaaaagaaga acctttggga accaatcaaa agctcgattt | 2280 |
| cagtagcgat aattttgaaa agcttgagtc agcactactt cctggtaccc tggttgatgt | 2340 |
| attcttctca gtcgagcctt acgattataa gaaaatggta gggatacgtc tagcagccag | 2400 |
| aaagttggta atccagctga agaaatgatc tagccaagga aaaatcattc ctctgtctct | 2460 |
| tcctgttcag tcggtgagca ctt | 2483 |

<210> SEQ ID NO 41
<211> LENGTH: 1491
<212> TYPE: DNA
<213> ORGANISM: Boechera

<400> SEQUENCE: 41

| | |
|---|---:|
| atggcttcga ctctgggcgg cgatgagaga aacgagatag tgttttttcga tcttgagact | 60 |
| gcggttccga ccaaatcggg gcagccttttt gcgattttgg agtttggggc tatcttagtt | 120 |
| tgccctatga agctagtgga gctctatagt tactccactt tggttcgacc taccgatctt | 180 |
| tctctcatct ccacgctcac gaagcgacga agcggcatta cgcgcgacgg agttctctct | 240 |
| gcacctacat tctctgaaat cgctgatgaa gtctacgaca ttctccacgg acgaatttgg | 300 |
| gcgggacata acataaagag attcgattgt gtaagaataa gagatgcatt tgcagaaatt | 360 |
| ggtctccctc ccccggagcc gaaagctaca attgattcac tttcgttgtt gtctcagaag | 420 |
| tttgggaaga gagctggtga catgaagatg gcatcgcttg ctacatattt cgggctagga | 480 |
| gatcaagctc acaggagctt agatgatgtc cggatgaatc ttgaagttat caagcactgt | 540 |
| tcaaccgtct tgtttctgga gtccagtgtt cctgacattc ttacagacat gagctggtta | 600 |
| ttcccaagaa aaagtccgag aacacgaagt aatgagaagt cactgcctaa tggagtcaga | 660 |
| gaaagcccga cttcttcctc ttcgagccct caaactgatc cgagttcgtc ttctgtagat | 720 |
| gccacagctg tcaaaaacca tcccatcatt tctcttctga cggaatgctc agaaagtgat | 780 |
| acatctagtt gtgaaataga tccatctgac ataaccactc taataagtaa actacatatt | 840 |
| ggaactctta agacagatgc tgcggacgaa gccaaaactg taagcagca gggtgaatca | 900 |
| accgatccca atgccaaaga tgaatcattt ttgggcgtta atgaagtatc tgtttctagc | 960 |
| atcagggcaa gtcttatccc gttatatcgt aggagtctga aatggagct gtttcacaac | 1020 |
| gacacccctc tacatctctg ttggtatagc ttgaaaattc ggtttggaat aagccggaag | 1080 |
| tatgtggatc atgtaggtcg tccaaagatg aatattgttg tagacatacc tcctgattta | 1140 |
| tgcaagatct tggacgcatc cgatgctgct gcgcataact tactgattga ctcaagcaca | 1200 |
| agctcagatt ggaggcctac cgttatgagg aaaaaaggct ttgccaacta tcccacagcc | 1260 |
| agactgcaaa taagctcaga atccaatgga acccaggtat accaaaaaga gaacctttg | 1320 |

```
ggaaccaatc aaaagctcga tttcagtagc gataattttg aaaagcttga gtcagcacta    1380
cttcctggta ccctggttga tgtattcttc tcagtcgagc cttacgatta taagaaaatg    1440
gtagggatac gtctagcagc cagaaagttg gtaatccagc tgaagaaatg a             1491

<210> SEQ ID NO 42
<211> LENGTH: 495
<212> TYPE: DNA
<213> ORGANISM: Boechera

<400> SEQUENCE: 42
gtgtttttcg atcttgagac tgcggttccg accaaatcgg ggcagccttt tgcgattttg     60
gagtttgggg ctatcttagt ttgccctatg aagctagtgg agctctatag ttactccact    120
ttggttcgac ctaccgatct ttctctcatc tccacgctca cgaagcgacg aagcggcatt    180
acgcgcgacg gagttctctc tgcacctaca ttctctgaaa tcgctgatga agtctacgac    240
attctccacg gacgaatttg gcgggacat aacataaaga gattcgattg tgtaagaata     300
agagatgcat ttgcagaaat tggtctccct ccccccggagc cgaaagctac aattgattca    360 cttttcgttgt tgtctcagaa gtttgggaag agagctggtg acatgaagat ggcatcgctt    420
gctacatatt tcgggctagg agatcaagct cacaggagct tagatgatgt ccggatgaat    480
cttgaagtta tcaag                                                     495

<210> SEQ ID NO 43
<211> LENGTH: 2488
<212> TYPE: DNA
<213> ORGANISM: Boechera

<400> SEQUENCE: 43
tcgtaccgtt gcttctctca agtttagatt ttttttccgta aaaagaggag gtggcccgtg    60
aagtttattc ccttttaaaac ccaccaatta gctccttcac tctcagttct caacaatggc   120
ttcgactctg ggcggcgatg agagaaacga gatagtgttt ttcgatcttg agactgcggt   180
tccgaccaaa tcggggcagc cttttgcgat tttggagttt ggggctatct tagttttgccc   240 tatgaagcta gtggagctct atagttactc cactttggtt cgacctaccg atctttctct   300
catctccacg ctcacgaagc gacgaagcgg cattacgcgc gacggagttc tctctgcacc   360
tacattctct gaaatcgctg atgaagtcta cgacattctc cacggtaagg gtttctcttt   420
ttttttttct ttctcaatct ctctcacgcg aagctacaag tattgatttt ggtgtttctg   480
taggacgaat ttgggcggga cataacataa agagattcga ttgtgtaaga ataagagatg   540
catttgcaga aattggtctc cctccccccgg agccgaaagc tacaattgat tcactttcgt   600
tgttgtctca gaagtttggg aagagagctg gtgacatgaa ggtctctctt ttttcgtctt   660
ctcgatgata aatctcaaag cctatagctt ccttgttatc tttatagata tgaattttcaa   720 tgtaacttca aagattcatc actcatcaaa gttgctaaaa tttactctaa ataatgtaga   780
tggcatcgct tgctacatat ttcgggctag gagatcaagc tcacaggtaa aacagtaaac   840 gatacccctgt gccttttaac gattcaccag ttgtttcaat atgggactaa acatggatat   900
gattcaccag gagcttagat gatgtccgga tgaatcttga agttatcaag cactgtgcaa   960
ccgtcttgtt tctggtattg ttgtcttctc atttcttgaa taatgattaa ctctaactta   1020
aaaggattag attaaagagg ttgagacata tctgacttct gtctacagtt tgcaaaagtt   1080
gggtccatct tccttccaga ccacaacttt gcaagccgta aacatggttt gcaagtatag   1140
```

```
tttgtcatat cactgagttt aagtacttgg tgtttgcagg agtccagtgt tcctgacatt      1200
cttacagaca tgagctggtt attcccaaga aaaagtccga gaacacgaag taatgagaag      1260
tcactgccta atggagtcag agaaagcccg acttcttcct cttcgagccc taaaactgat      1320
ccgagttcgt cttctgtaga tgccacagct gtcaaaaacc atcccatcat ttctcttctg      1380
acggaatgct cagaaagtga tacatctagt tgtgaaatag atccatctga cataaccact      1440
ctaataagta aactacatat tggaactctt aagagagatg ctgcggacga agccaaaatt      1500
gtaagacagc agggtgaatc aaccgatccc aatgccaaag atgaatcatt tttgggcgtt      1560
aatgaagtat ctgttttctag catcagggca agtcttatcc cgttatatcg tgggagtctg      1620
agaatggagc tgtttcacaa tgacacccct ctacatctct gttggtatag cttgaaaatt      1680
cggtttggaa taagccggaa gtatgtggat catgtaggtc gtccaaagat gaatattgtt      1740
gtagacatac ctcctgattt atgcaagatc ttggacgcat acgatgctgc tgcgcataac      1800
ttactgattg actcaagcac aagctcagat tggaggccta ctgttatgag gaaagaaggc      1860
tttgccaact atcccacagc cagactgcag taagtattca acactctctc tgaccttta     1920
catacgagca tgaatccacc ggagagtctc taagaccatc tccaaccca ctccgtattc      1980
acctccaaac tctattttgg agttaaatcc ctccaaccct tgcaaaatag atatcttcaa      2040
aattttctcc atatttggag attttgattt tttaagtcat gactccattt tggagttggg      2100
ttggagaaaa acacaactcc aaaatagagt tacttcattt tggagtaaaa aaatgaagaa      2160
atgggttgga gatactctaa cctctttcac cattcttatg ttgttggcag aataagctca      2220
gaatccaatg gaacccaggt ataccaaaaa gaagaacctt tgggaaccaa tcaaaagctc      2280
gatttcagta gcgataattt tgaaaagctt gagtcagcac tacttcctgg taccctggtt      2340
gatgcattct tctcacccga atcttacgat tataagaaaa tggtagggat acgtctagca      2400
gccagaaagt tggtaatcca cctgaagaaa tgatctagcc aaggaaaaat cattcctctg      2460
tctcttcctg gtcagtcggt gagcactt                                        2488

<210> SEQ ID NO 44
<211> LENGTH: 1491
<212> TYPE: DNA
<213> ORGANISM: Boechera

<400> SEQUENCE: 44
atggcttcga ctctgggcgg cgatgagaga aacgagatag tgttttttcga tcttgagact        60
gcggttccga ccaaatcggg gcagccttt gcgattttgg agtttggggc tatcttagtt       120
tgccctatga agctagtgga gctctatagt tactccactt tggttcgacc taccgatctt       180
tctctcatct ccacgctcac gaagcgacga agcggcatta cgcgcgacgg agttctctct       240
gcacctacat tctctgaaat cgctgatgaa gtctacgaca ttctccacgg acgaatttgg       300
gcgggacata acataaagag attcgattgt gtaagaataa gagatgcatt tgcagaaatt       360
ggtctccctc ccccggagcc gaaagctaca attgattcac tttcgttgtt gtctcagaag       420
tttgggaaga gagctggtga catgaagatg gcatcgcttg ctacatattt cgggctagga       480
gatcaagctc acaggagctt agatgatgtc cggatgaatc ttgaagttat caagcactgt       540
gcaaccgtct tgtttctgga gtccagtgtt cctgacattc ttacagacat gagctggtta       600
ttcccaagaa aaagtccgag aacacgaagt aatgagaagt cactgcctaa tggagtcaga       660
gaaagcccga cttcttcctc ttcgagccct aaaactgatc cgagttcgtc ttctgtagat       720
gccacagctg tcaaaaacca tcccatcatt tctcttctga cggaatgctc agaaagtgat       780
```

```
acatctagtt gtgaaataga tccatctgac ataaccactc taataagtaa actacatatt    840
ggaactctta agagagatgc tgcggacgaa gccaaaattg taagacagca gggtgaatca    900
accgatccca atgccaaaga tgaatcattt tgggcgtta atgaagtatc tgtttctagc     960
atcagggcaa gtcttatccc gttatatcgt gggagtctga aatgagct gtttcacaat    1020 gacacccctc tacatctctg ttggtatagc ttgaaaattc ggtttggaat aagccggaag   1080
tatgtggatc atgtaggtcg tccaaagatg aatattgttg tagacatacc tcctgattta   1140
tgcaagatct tggacgcata cgatgctgct gcgcataact tactgattga ctcaagcaca   1200
agctcagatt ggaggcctac tgttatgagg aaagaaggct tgccaacta tcccacagcc    1260 agactgcaaa taagctcaga atccaatgga acccaggtat accaaaaaga agaacctttg   1320
ggaaccaatc aaaagctcga tttcagtagc gataattttg aaaagcttga gtcagcacta   1380
cttcctggta ccctggttga tgcattcttc tcacccgaat cttacgatta taagaaaatg   1440
gtagggatac gtctagcagc cagaaagttg gtaatccacc tgaagaaatg a            1491

<210> SEQ ID NO 45
<211> LENGTH: 495
<212> TYPE: DNA
<213> ORGANISM: Boechera

<400> SEQUENCE: 45
gtgtttttcg atcttgagac tgcggttccg accaaatcgg ggcagccttt tgcgattttg     60
gagtttgggg ctatcttagt ttgccctatg aagctagtgg agctctatag ttactccact   120
ttggttcgac ctaccgatct ttctctcatc tccacgctca cgaagcgacg aagcggcatt   180
acgcgcgacg gagttctctc tgcacctaca ttctctgaaa tcgctgatga agtctacgac   240
attctccacg gacgaatttg gcgggacat aacataaaga gattcgattg tgtaagaata    300
agagatgcat ttgcagaaat tggtctccct ccccccggagc cgaaagctac aattgattca   360 cttttcgttgt tgtctcagaa gtttgggaag agagctggtg acatgaagat ggcatcgctt   420
gctacatatt tcgggctagg agatcaagct cacaggagct tagatgatgt ccggatgaat   480
cttgaagtta tcaag                                                    495

<210> SEQ ID NO 46
<211> LENGTH: 2519
<212> TYPE: DNA
<213> ORGANISM: Boechera

<400> SEQUENCE: 46
tcgtaccgtt gcttctctca agtttagatt ttttttccgt aaatagagga ggatcaattg     60
ctttaaaacc caccaattag ctccttcact ctcagttctc aacaatggct tcgactctgg   120
gcggcgatga gagatgcgag atagtgtttt tcgatcttga cggcggtt ccgaccaaat     180 cggggcagc ttttgcgatt ttggagtttg gggctatctt agtttgccct atgaagctag    240
tggagctcta tagttactcc actttggttc gacccaccga tctttctctc atctccacgc   300
tcacgaagcg acgaagcggc attacgcgcg acggagttct ctctgcacct acattctctg   360
aaatcgctga tgaagtctac gacattctcc acggtaaggg tttctctttt tttttttttct   420 ttctcaatct ctctgacacg aagctacaag tattgatttt ggtgtttctg taggacgaat   480
ttgggcggga cataacataa agagattcga ttgtgtaaga ataagagatg catttgcagg    540
aattggtgtc tctccccccgg agccgaaagc tacaattgat tcactttcgt tgttgtctca   600
```

```
gaagtttggg aagagagctg gtgacatgaa ggtctctctt ttttcgtctt ctcgatgata     660
aatctcaaag cctatagctt ccttgttatc tttatagata tgaatttcca tgtaacttca     720
aagattcatc actcatcaga gttgctaaaa tttactcttt ttaaaaaatg tagatggcat     780
cgcttgctac atatttcggg ctaggagatc aagctcacag gtaaaaagag taaacgatac     840
catgtgcctt ttaacgattc accagttgtt tcaatatggg actaaacatg gttatgattc     900
accaggagct tagatgatgt ccggatgaat cttgaagtag tcaagtactg tgcaaccgtc     960
ttgtttctgg tattgctgtc ttttcatttc ttgaataatg attaactcta acttaaaagg    1020
attagattag agaggttgag acatatctga cttctgtcta cagtttgcaa agttgggtc     1080 catcttcctt tcagaccaca actttgcaag ccgtaaacat gggttgcaac ttgcaagtat    1140
agtttgtcat atcactgagt ttaagtactt ggtgtttgca ggagtccagt gttcctgaca    1200
ttcttaaaga catgagctgg ttttccccaa gaaaaagtcc gagaacacga agtaatgaga    1260
agtcactgcc taatggagtc agagaaagcc cgacttcttc ctcttcaagc cctaaaactg    1320
atccgagttc gtcttctgta gatgccacaa ctgtcaaaaa ccatcccatc atttctcttc    1380
tgacggaatg ctcagaaagt gatacatcta gttgtgaaat agatccatct gacataacca    1440
ctctaataag taaactacat attggaactc ttaagagaga tgctgcggac gaagccaaaa    1500
ctgtgagaga tgctgcggac gaagccaaaa ctgtaagaca gcagggtgaa tcaaccgatc    1560
ccaatgccaa agatgaatca tttttgggcg ttaatgaagt atctgtttct agcatcaggg    1620
caagtcttat cccgttatat cgtgggagtc tgagaatgga gctgtttcac aatgacaccc    1680
ctctacatct ctgttggtat agcttgaaaa ttcggtttgg aataagccgg aagtatgtgg    1740
atcatgtagg tcgtccaaag atgaatattg ttgtagacat acctcctgat ttatgcaaga    1800
tcttggacgc atccgatgct gctgcgcata acttactgat tgactcaagc acaagctcag    1860
attggaggcc tactgttatg aggaaagaag gctttgccaa ctatcccaca gccagactgc    1920
agtaagtatt caacactctc tctgaccttt tacatacgag catgaatcca ccggagagtc    1980
tctaagacca tctccaaccc tactccgtat tcacctccaa actctatttt ggagttaaat    2040
ccctccaacc cttgcaaaat agatatcttc aaaattttct ccatatttgg agatttttgaa    2100 tttttaagtc atgactccat tttggagttg ggttggagaa aaacacaact ccaaaataga    2160
gttacttcat tttggagtaa aaaatgaaga aatgggttgg agatactcta acctctgtca    2220
ccattcttat gttgttggca gaataagctc agaatccaat ggaacccagg tacaccaaaa    2280
agaagaacct ttgggaacca atcaaaagct cgatttcagt agcgataatt ttgaaaagct    2340
tgagtcagca ctacttcctg gtaccctggt tgatgcattc ttctcactcg agccttacga    2400
ttataagaaa atggtaggga tacgtctagc agccagaaag ttggtaatcc acctgaagaa    2460
atgatctagc caaggaaaaa tcattcctct gtctcttgct ggtcagtcgg tgagcactt     2519
```

<210> SEQ ID NO 47
<211> LENGTH: 1521
<212> TYPE: DNA
<213> ORGANISM: Boechera

<400> SEQUENCE: 47

```
atggcttcga ctctgggcgg cgatgagaga tgcgagatag tgttttttcga tcttgagacg      60 gcggttccga ccaaatcggg gcagcctttt gcgattttgg agtttggggc tatcttagtt     120
tgccctatga agctagtgga gctctatagt tactccactt tggttcgacc caccgatctt     180
tctctcatct ccacgctcac gaagcgacga agcggcatta cgcgcgacgg agttctctct     240
```

```
gcacctacat tctctgaaat cgctgatgaa gtctacgaca ttctccacgg acgaatttgg    300
gcgggacata acataaagag attcgattgt gtaagaataa gagatgcatt tgcaggaatt    360
ggtgtctctc ccccggagcc gaaagctaca attgattcac tttcgttgtt gtctcagaag    420
tttgggaaga gagctggtga catgaagatg gcatcgcttg ctacatattt cgggctagga    480
gatcaagctc acaggagctt agatgatgtc cggatgaatc ttgaagtagt caagtactgt    540
gcaaccgtct tgtttctgga gtccagtgtt cctgacattc ttaaagacat gagctggttt    600
tccccaagaa aaagtccgag aacacgaagt aatgagaagt cactgcctaa tggagtcaga    660
gaaagcccga cttcttcctc ttcaagccct aaaactgatc cgagttcgtc ttctgtagat    720
gccacaactg tcaaaaacca tcccatcatt tctcttctga cggaatgctc agaaagtgat    780
acatctagtt gtgaaataga tccatctgac ataaccactc taataagtaa actacatatt    840
ggaactctta agagagatgc tgcggacgaa gccaaaactg tgagagatgc tgcggacgaa    900
gccaaaactg taagacagca gggtgaatca accgatccca atgccaaaga tgaatcattt    960
ttgggcgtta atgaagtatc tgtttctagc atcagggcaa gtcttatccc gttatatcgt   1020
gggagtctga gaatggagct gtttcacaat gacaccctc tacatctctg ttggtatagc    1080
ttgaaaattc ggtttggaat aagccggaag tatgtggatc atgtaggtcg tccaaagatg   1140
aatattgttg tagacatacc tcctgattta tgcaagatct tggacgcatc cgatgctgct   1200
gcgcataact tactgattga ctcaagcaca agctcagatt ggaggcctac tgttatgagg   1260
aaagaaggct ttgccaacta tcccacagcc agactgcaaa taagctcaga atccaatgga   1320
acccaggtac accaaaaaga agaacctttg gaaccaatc aaaagctcga tttcagtagc    1380
gataattttg aaaagcttga gtcagcacta cttcctggta ccctggttga tgcattcttc   1440
tcactcgagc cttacgatta taagaaaatg gtagggatac gtctagcagc cagaaagttg   1500
gtaatccacc tgaagaaatg a                                             1521

<210> SEQ ID NO 48
<211> LENGTH: 495
<212> TYPE: DNA
<213> ORGANISM: Boechera

<400> SEQUENCE: 48 gtgttttcg atcttgagac ggcggttccg accaaatcgg ggcagccttt tgcgattttg     60
gagtttgggg ctatcttagt ttgccctatg aagctagtgg agctctatag ttactccact    120
ttggttcgac ccaccgatct ttctctcatc tccacgctca cgaagcgacg aagcggcatt    180
acgcgcgacg gagttctctc tgcacctaca ttctctgaaa tcgctgatga agtctacgac    240
attctccacg gacgaatttg gcgggacata acataaaga gattcgattg tgtaagaata    300
agagatgcat ttgcaggaat tggtgtctct ccccggagc cgaaagctac aattgattca    360
ctttcgttgt tgtctcagaa gtttgggaag agagctggtg acatgaagat ggcatcgctt    420
gctacatatt tcgggctagg agatcaagct cacaggagct tagatgatgt ccggatgaat    480
cttgaagtag tcaag                                                    495

<210> SEQ ID NO 49
<211> LENGTH: 2487
<212> TYPE: DNA
<213> ORGANISM: Boechera

<400> SEQUENCE: 49
```

```
tcgtaccgtt gcttctctca aggttagatt ttttttccgt aaaaagagga ggatcgattg    60
ctttaaaacc caccaattag ctccttcact ctcagtcctt aacaatggct tcgactctgg   120
gcggcgatga gagatgcgag atagtgtttt tcgatcttga gacggcagtt ccgaccaaat   180
cggggcagcc ttttgcgatt ttggagtttg ggctatctt agtttgccct atgaagctag    240
tggagctcta tagttactcc accttggttc gacccacaga tctttctctc atctccacgc   300
tcacgaagcg acgaagcggc attacgcgcg acggagttct ctctgcacct acattctctg   360
aaatcgctga tgaagtctac gacattctcc acggtaaggg tttctctttt tttttctct    420 ccatctctct cacacgaagg tacaagtatt gattttggtg tttctgtagg acgaatttgg   480
gcgggacata acataaagag attcgattgt gtaagaataa gagatgcatt tgcaggaatt   540
ggtctctctc ccccggagcc gaaagctaca attgattcac tttcgttgtt gtctcagaag   600
tttgggaaga gagctggtga catgaaggtc tctcttttt cgtcttctcg atgataaatc     660
tcaaagccaa tagcttcctt gttatcttta tagatatgaa tttccatgta acttcaaaga   720
ttcatcactc atcagagttg ctaaaattta ctcttttca ataacgtaga tggcatcgct     780
tgctacatat ttcgggctag gagatcaagc tcacaggtaa aaagagtaaa cgataccctg   840
tgccttttaa cgattcacca gttgtttcaa tatgggacta acatggtta tgattcacca    900 ggagcttaga tgatgtccgg atgaatcttg aagtagtcaa gtactgtgca accgtcttat   960
ttctggtatt gctgtcttct catttcttga ataatgatca actctaactt aaaaaggatt  1020
agattagaga ggttgagaca tatctgactt ctgtctacag tttgcaaaag ttgggtccat  1080 cttccttttca gaccacaact ttgcaagccg taaacatggg ttgcaacttg caagtatagt  1140
ttgtcatatc actgagttta agtacttggt gtttgcagga gtccagtgtt cctgacattc  1200
ttaaagacat gagctggttt tccccaagaa aaagtccgag aacacgaagt aatgagaagt  1260
cactgcctaa tggagtcaga gaaagcccga cttcttcctc ttcaagccct aaaactgatc  1320
cgagttcgtc ttctgtagat gccacaactg tcaaaaacca tcccatcatt tctcttctga  1380
cggaatgctc agaaagtgat acatctagtt gtgaaataga tccatctgac ataaccactc  1440
taataagtaa actacatatt ggaactctta agagagatgc tgcggatgaa gccaaaattg  1500
taagacagca gggtgaatca accgatccca atgccaaaga tgaatcattt ttgggcgtta  1560
atgaagtatc tgtttctagc atcagggcaa gtcttatccc gttatatcgt gggagtctga  1620
gaatggagct gcttcacaat gacacccctc tacatctctg ttggtatagc ttgaaaattc  1680
ggtttggaat aagccggaag tatgtggatc atgtaggtcg tccaaagatg aatattgttg  1740
tagacatacc tcctgattta tgcaagatct tggacgcata cgatgctgct gcgcataact  1800
tactgattga ctcaagcaca agctcagatt ggaggcctac tgttatgagg aaagaaggct  1860
ttgccaacta tcccacagcc agactgcagt aagtattcaa cactctctct gaccttttac  1920
atacgagcat gaatccaccg gagagtctct aaaaccatct ccaaccctac tccgtattca  1980
cctccaaact ctattttgga gttaaatccc tccaacccct gcaaaataga tatcttcaaa  2040 atttctcca tatttggaga ttttgatttt ttaagtcatg actccatttt ggagttgggt    2100
tggagaaaaa cacaactcca aaatagagtt acttcatttt ggagtaaaaa aatgaagaaa  2160
tgggttggag atactctaac ctctgtcacc attcttatgt tgttggcaga ataagctcag  2220
aatccaatgg aacccaggta taccaaaaag aagaaccttt gggaaccaat caaaagctcg  2280
atttcagtag cgataatttt gaaaagcttg agtcagcact acttcctggt accctggttg  2340
atgcattctt ctcactcgaa tcttacgatt ataagaaaat ggtagggata cgtctagcag  2400
```

```
ccagaaagtt ggtaatccac ctgaagaaat gatctagcca aggaaaaatc attcctctgt      2460
ctcttcctgg tcagtcggtg agcactt                                         2487

<210> SEQ ID NO 50
<211> LENGTH: 1491
<212> TYPE: DNA
<213> ORGANISM: Boechera

<400> SEQUENCE: 50
atggcttcga ctctgggcgg cgatgagaga tgcgagatag tgttttttcga tcttgagacg      60 gcagttccga ccaaatcggg gcagccttt gcgattttgg agtttggggc tatcttagtt      120
tgccctatga agctagtgga gctctatagt tactccacct tggttcgacc cacagatctt     180
tctctcatct ccacgctcac gaagcgacga agcggcatta cgcgcgacgg agttctctct     240
gcacctacat tctctgaaat cgctgatgaa gtctacgaca ttctccacgg acgaatttgg     300
gcgggacata acataaagag attcgattgt gtaagaataa gagatgcatt tgcaggaatt     360
ggtctctctc ccccggagcc gaaagctaca attgattcac tttcgttgtt gtctcagaag     420
tttgggaaga gagctggtga catgaagatg gcatcgcttg ctacatattt cgggctagga     480
gatcaagctc acaggagctt agatgatgtc cggatgaatc ttgaagtagt caagtactgt     540
gcaaccgtct tatttctgga gtccagtgtt cctgacattc ttaaagacat gagctggttt     600
tccccaagaa aaagtccgag aacacgaagt aatgagaagt cactgcctaa tggagtcaga     660
gaaagcccga cttcttcctc ttcaagccct aaaactgatc cgagttcgtc ttctgtagat     720
gccacaactg tcaaaaacca tcccatcatt tctcttctga cggaatgctc agaaagtgat     780
acatctagtt gtgaaataga tccatctgac ataaccactc taataagtaa actacatatt     840
ggaactctta agagagatgc tgcggatgaa gccaaaattg taagacagca gggtgaatca     900
accgatccca tgccaaaga tgaatcattt ttgggcgtta atgaagtatc tgtttctagc     960
atcagggcaa gtcttatccc gttatatcgt gggagtctga aatggagct gcttcacaat     1020 gacaccctc tacatctctg ttggtatagc ttgaaaattc ggtttggaat aagccggaag    1080
tatgtggatc atgtaggtcg tccaaagatg aatattgttg tagacatacc tcctgattta    1140
tgcaagatct tggacgcata cgatgctgct gcgcataact tactgattga ctcaagcaca    1200
agctcagatt ggaggcctac tgttatgagg aaagaaggct ttgccaacta tcccacagcc    1260
agactgcaaa taagctcaga atccaatgga acccaggtat accaaaaaga gaacctttg    1320 ggaaccaatc aaaagctcga tttcagtagc gataattttg aaaagcttga gtcagcacta    1380
cttcctggta ccctggttga tgcattcttc tcactcgaat cttacgatta taagaaaatg    1440
gtagggatac gtctagcagc cagaaagttg gtaatccacc tgaagaaatg a           1491

<210> SEQ ID NO 51
<211> LENGTH: 495
<212> TYPE: DNA
<213> ORGANISM: Boechera

<400> SEQUENCE: 51 gtgttttttcg atcttgagac ggcagttccg accaaatcgg ggcagccttt tgcgattttg     60
gagtttgggg ctatcttagt ttgccctatg aagctagtgg agctctatag ttactccacc    120
ttggttcgac ccacagatct ttctctcatc tccacgctca cgaagcgacg aagcggcatt    180
acgcgcgacg gagttctctc tgcacctaca ttctctgaaa tcgctgatga agtctacgac    240
```

```
attctccacg acgaatttg ggcgggacat aacataaaga gattcgattg tgtaagaata      300
agagatgcat ttgcaggaat tggtctctct cccccggagc cgaaagctac aattgattca      360
cttccgttgt tgtctcagaa gtttgggaag agagctggtg acatgaagat ggcatcgctt      420
gctacatatt tcgggctagg agatcaagct cacaggagct tagatgatgt ccggatgaat      480
cttgaagtag tcaag                                                       495
```

<210> SEQ ID NO 52
<211> LENGTH: 2486
<212> TYPE: DNA
<213> ORGANISM: Boechera

<400> SEQUENCE: 52

```
tcgtaccgtt gcttctctca agtttagatt ttttttccgt aaatagagga ggatcaattg       60 cttttaaaacc caccaattag ctccttcact ctcagttctc aacaatggct tcgactctgg     120
gcggcgatgg gagatgcgag atagtgtttt tcgatcttga gacggcggtt ccgaccaaat     180
cggggcagcc ttttgcgatt ttggagtttg ggctatcttt agtttgccct atgaagctag     240
tggagctcta tagttactcc actttggttc gacccaccga tctttctctc atctccacgc     300
tcacgaagcg acgaagcggc attacgcgcg acggagttct ctctgcacct acattctctg     360
aaatcgctga tgaagtctac gacattctcc acggtaaggg tttctctttt tttttttctt     420
tctcaatctc tctgacacga agctacaagt attgattttg gtgtttctgt aggacgaatt     480
tgggcgggac ataacataaa gagattcgat tgtgtaagaa tacgagatgc atttgcagga     540
attggtctct ctcccccgga gccgaaagct acaattgatt cactttcgtt attgtctcag     600
aagtttggga agagagctgg tgacatgaag gtctctcttt tttcgtcttc tcgatgataa     660
atctcaaagc ctatagcttc cttgttatct ttatagatat gaatttccat gtaacttcaa     720
agattcatca ctcatcagag ttgctaaaat ttactctttt taaaaaatgt agatggcatc     780
gcttgctaca tatttcgggc taggagatca ggctcacagg taaaaagagt aaacgatacc     840
atgtgccttt taacgattca ccagttgttt caatatggga ctaaacatgg ttatgattca     900
ccaggagctt agatgatgtc cggatgaatc ttgaagtagt caagtactgt gcaaccgtct     960
tgtttctggt attgctgtct tttcattct tgaataatga ttaactctaa cttaaaagga    1020
ttagattaga gaggttgaga catatctgat ttctgtctac agtttgcaaa agttggttcc    1080
atcttccttt cagaccacaa ctttgcaagc cgtaaacatg ggttgcaact tgcaagtata    1140
gtttgttata tcactgagtt taagtacttg gtgtttgcag gagtccagtg ttcctgacat    1200
tcttaaagac atgagctggt tttccccaag aaaaagtccg agaacacgaa gtaatgagaa    1260
gtcactgcct aatggagtca gagaaagccc gacttcttcc tcttcaagcc ctaaaactga    1320
tccgagttcg tcttctgtag atgccacaac tgtcaaaaac catcccatca tttctcttct    1380
gacggaatgc tcagaaagtg atacatctag ttgtgaaata gatccatctg acataaccac    1440
tctaataagt aaactacata ttggaactct taagagagat gctgcggacg aagccaaaac    1500
tgtaagacag cagggtgaat caaccgatcc caatgccaaa gatgaatcat ttttgggcgt    1560
taatgaagta tctgtttcta gcatcagggc aagtcttatc ccgttatatc gtgggggtct    1620
gagaatggag ctgtttcaca atgacacccc tctacatctc cgttggtata gcttgaaaat    1680
tcggtttgga ataagccgga agtatgtgga tcatgtaggt cgtccaaaga tgaatattgt    1740
cgtagacata cctcctgatt tatgcaagat cttgacgca tccgatgctg ctgcgcataa    1800
cttactgatt gactcaagca caagctcaga ttggaggcct actgttatga ggaaagaagg    1860
```

```
ctttgccaac tatcccacag ccagactgca gtaagtattc agcactctct ctgaccttt    1920 acatacgagc atgaatccac cggagagtct ctaagaccat ctccaaccct actccgtatt    1980
cacctccaaa ctctatttg gagttaaatc cctccaaccc ttgcaaaata gacatcttca     2040
aaattttctc catatttgga gattttgatt ttttaagtca tgactccatt ttggagttgg    2100
gttggagaaa acacaactc caaaatagat ttacttcatt ttggagtaaa aaatgaagaa     2160
atgggttgga gatactaacc tctgtcacca ttcttatgtt gttggcagaa taagctcaga    2220
atccaatgga acccaggtac accaaaaaga gaacctttg gaaccaatc aaaagctcga      2280 tttcagtagc gataatttg aaaagcttga gtcagcactt cttcctggta ccctggttga    2340
tgcattcttc tcactcgagc cttacgatta taagaaaatg gtagggatac gtctagcagc    2400
cagaaagttg gtaatccacc tgaagaaatg atctagccaa ggaaaaatca ttcctctgtc    2460
tcttcctggt cagtcggtga gcactt                                         2486

<210> SEQ ID NO 53
<211> LENGTH: 1491
<212> TYPE: DNA
<213> ORGANISM: Boechera

<400> SEQUENCE: 53
atggcttcga ctctgggcgg cgatgggaga tgcgagatag tgttttttcga tcttgagacg    60 gcggttccga ccaaatcggg gcagccttt gcgattttgg agtttggggc tatcttagtt    120
tgccctatga agctagtgga gctctatagt tactccactt tggttcgacc caccgatctt   180
tctctcatct ccacgctcac gaagcgacga agcggcatta cgcgcgacgg agttctctct   240
gcacctacat tctctgaaat cgctgatgaa gtctacgaca ttctccacgg acgaattgg    300 gcgggacata acataaagag attcgattgt gtaagaatac gagatgcatt tgcaggaatt   360
ggtctctctc ccccggagcc gaaagctaca attgattcac tttcgttatt gtctcagaag   420
tttgggaaga gagctggtga catgaagatg gcatcgcttg ctacatattt cgggctagga   480
gatcaggctc acaggagctt agatgatgtc cggatgaatc ttgaagtagt caagtactgt   540
gcaaccgtct tgtttctgga gtccagtgtt cctgacattc taaagacat gagctggttt    600 tccccaagaa aaagtccgag aacacgaagt aatgagaagt cactgcctaa tggagtcaga   660
gaaagcccga cttcttcctc ttcaagccct aaaactgatc cgagttcgtc ttctgtagat   720
gccacaactg tcaaaaacca tcccatcatt tctcttctga cggaatgctc agaaagtgat   780
acatctagtt gtgaaataga tccatctgac ataaccactc taataagtaa actacatatt   840
ggaactctta agagagatgc tgcggacgaa gccaaaactg taagacagca gggtgaatca   900
accgatccca atgccaaaga tgaatcattt ttgggcgtta atgaagtatc tgtttctagc   960
atcagggcaa gtcttatccc gttatatcgt gggggtctga aatggagct gtttcacaat    1020 gacacccctc tacatctccg ttggtatagc ttgaaaattc ggtttggaat aagccggaag   1080
tatgtggatc atgtaggtcg tccaaagatg aatattgtcg tagacatacc tcctgattta   1140
tgcaagatct tggacgcatc cgatgctgct gcgcataact tactgattga ctcaagcaca   1200
agctcagatt ggaggcctac tgttatgagg aagaaggct tgccaactaa tcccacagcc    1260
agactgcaaa taagctcaga atccaatgga acccaggtac accaaaaaga gaacctttg    1320 ggaccaatc aaaagctcga tttcagtagc gataatttg aaaagcttga gtcagcactt    1380
cttcctggta ccctggttga tgcattcttc tcactcgagc cttacgatta taagaaaatg   1440
```

```
gtagggatac gtctagcagc cagaaagttg gtaatccacc tgaagaaatg a           1491
```

<210> SEQ ID NO 54
<211> LENGTH: 495
<212> TYPE: DNA
<213> ORGANISM: Boechera

<400> SEQUENCE: 54

```
gtgttttcg atcttgagac ggcggttccg accaaatcgg ggcagccttt tgcgattttg    60
gagtttgggg ctatcttagt ttgccctatg aagctagtgg agctctatag ttactccact  120
ttggttcgac ccaccgatct ttctctcatc tccacgctca cgaagcgacg aagcggcatt  180
acgcgcgacg gagttctctc tgcacctaca ttctctgaaa tcgctgatga agtctacgac  240
attctccacg gacgaatttg ggcgggacat aacataaaga gattcgattg tgtaagaata  300
cgagatgcat ttgcaggaat tggtctctct cccccggagc cgaaagctac aattgattca  360
ctttcgttat tgtctcagaa gtttgggaag agagctggtg acatgaagat ggcatcgctt  420
gctacatatt tcgggctagg agatcaggct cacaggagct tagatgatgt ccggatgaat  480
cttgaagtag tcaag                                                   495
```

<210> SEQ ID NO 55
<211> LENGTH: 115
<212> TYPE: DNA
<213> ORGANISM: Boechera
<220> FEATURE:
<221> NAME/KEY: misc_feature
<222> LOCATION: (107)..(107)
<223> OTHER INFORMATION: n is a, c, g, or t

<400> SEQUENCE: 55

```
tcgtaccgtt gcttctctca agtttagatt ttttccgta aaaagaggag gtggcccgtg     60
aagtttattc cctttaaaac ccaccaatta gctccttcac tctcagntct caaca        115
```

<210> SEQ ID NO 56
<211> LENGTH: 105
<212> TYPE: DNA
<213> ORGANISM: Boechera
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t
<220> FEATURE:
<221> NAME/KEY: misc_feature

```
<222> LOCATION: (45)..(45)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 56
ncgtnncgnt gcntctctca agnttagatt tntttnnncg taaanagagg aggancnatt     60
gctttaaanc ccaccaatta gctccttcac tctcagnnct naaca                   105

<210> SEQ ID NO 57
<211> LENGTH: 115
<212> TYPE: DNA
<213> ORGANISM: Boechera

<400> SEQUENCE: 57
tcgtaccgtt gcttctctca agtttagatt tttttccgta aaaagaggag gtggcccgtg    60
aagtttattc cctttaaaac ccaccaatta gctccttcac tctcagttct caaca        115

<210> SEQ ID NO 58
<211> LENGTH: 115
<212> TYPE: DNA
<213> ORGANISM: Boechera

<400> SEQUENCE: 58
tcgtaccgtt gcttctctca agtttagatt tttttccgta aaaagaggag gtggcccgtg    60
aagtttattc cctttaaaac ccaccaatta gctccttcac tctcagttct caaca        115

<210> SEQ ID NO 59
<211> LENGTH: 115
<212> TYPE: DNA
<213> ORGANISM: Boechera

<400> SEQUENCE: 59
tcgtaccgtt gcttctctca agtttagatt tttttccgta aaaagaggag gtggcccgtg    60
aagtttattc cctttaaaac ccaccaatta gctccttcac tctcagttct caaca        115

<210> SEQ ID NO 60
<211> LENGTH: 104
<212> TYPE: DNA
<213> ORGANISM: Boechera

<400> SEQUENCE: 60
tcgtaccgtt gcttctctca agtttagatt tttttccgt aaatagagga ggatcaattg     60
ctttaaaacc caccaattag ctccttcact ctcagttctc aaca                   104

<210> SEQ ID NO 61
```

```
<211> LENGTH: 104
<212> TYPE: DNA
<213> ORGANISM: Boechera

<400> SEQUENCE: 61
tcgtaccgtt gcttctctca aggttagatt ttttttccgt aaaaagagga ggatcgattg    60
ctttaaaacc caccaattag ctccttcact ctcagtcctt aaca                   104

<210> SEQ ID NO 62
<211> LENGTH: 104
<212> TYPE: DNA
<213> ORGANISM: Boechera

<400> SEQUENCE: 62
tcgtaccgtt gcttctctca agtttagatt ttttttccgt aaatagagga ggatcaattg    60
ctttaaaacc caccaattag ctccttcact ctcagttctc aaca                   104

<210> SEQ ID NO 63
<211> LENGTH: 10
<212> TYPE: PRT
<213> ORGANISM: Boechera

<400> SEQUENCE: 63

Asp Ala Ala Asp Glu Ala Lys Thr Val Arg
1               5                   10

<210> SEQ ID NO 64
<211> LENGTH: 30
<212> TYPE: DNA
<213> ORGANISM: Boechera

<400> SEQUENCE: 64
agatgctgcg gacgaagcca aaactgtgag                                     30

<210> SEQ ID NO 65
<211> LENGTH: 20
<212> TYPE: DNA
<213> ORGANISM: Boechera

<400> SEQUENCE: 65
tggcccgtga agtttattcc                                                20
```

MEANS AND METHODS TO INDUCE APOMIXIS IN PLANTS

CROSS-REFERENCE TO RELATED APPLICATIONS

This application is a Continuation of 371 U.S. National Phase application Ser. No. 14/123,069, filed Nov. 27, 2013, which claims priority to PCT/EP2012/059808, filed May 25, 2012 based on European Patent Application No. 11168075.7 filed on May 30, 2011, the contents of which applications, including the Sequence Listing of 329810 bytes filed on Nov. 27, 2013 in U.S. National Phase application Ser. No. 14/123,069, are incorporated herein by reference in their entireties.

DESCRIPTION

The present invention relates to nucleic acid molecules for use in inducing apomixis in a plant, transgenic cells, in particular transgenic plant cells, comprising said nucleic acid molecule, transgenic plants, in particular plant seeds, comprising said nucleic acid molecule, methods for inducing apomixis in a plant, methods for the production of apomictic plants and uses thereof.

Naturally occurring vegetative, non-sexual reproduction in plants through seeds, also called apomixis, is a genetically controlled reproductive mechanism of plants primarily found in some polyploid non-cultivated species. Various types of apomixis, inter alia gametophytic and sporophytic, can be distinguished. In sporophytic apomixis also called adventitive embryony, a somatic embryo develops not from the gametophyte but directly from the cells of the nucellus, ovary wall or integuments. Somatic embryos from surrounding cells invade the sexual ovary, one of the somatic embryos out-competes the other somatic embryos and the sexual embryo, and utilizes the produced endosperm.

Gametophytic apomixis is a naturally-occurring type of asexual seed formation whereby progeny, which are clonal to the maternal genotype, are produced from meiotically-unreduced embryo sacs, i. e. the female gametophyte. Most gametophytic apomictic species are found in the Asteraceae, Rosaceae and Poaceae, where they have arisen independently and recurrently. Polyploidy, facultative apomixis (both sexual and apomictic seed production within one individual), and faster development of the apomeiotic ovule relative to the sexual one are traits which are shared among most of these taxa. Apomixis is derived from sex, and three independent developmental steps must be acquired for a sexual plant to produce seeds apomictically: the formation of an unreduced megaspore, that means the formation of an embryo sac having the same ploidy as the somatic cells of the mother plant from a meiotically-unreduced megaspore (diplospory, apomeiosis) or from nucellar cell (apospory), the subsequent development of an embryo from an unreduced egg in the absence of fertilization (parthenogenesis) and fertilization of the binucleate central cell to form a functional endosperm (pseudogamy). The term "apomeiosis" covers both apospory and diplospory. The apomeiotically-derived embryo thus receives its entire genome through the female line. As these components are under separate genetic control, it has been difficult to envision how all three could evolve in unison in a sexual ancestor considering random mutations, since the expression of any single step would decrease the fitness of its sexual carrier. It is widely accepted that apomictic seed development results from deregulation of the sexual development pathway, which would be manifested at multiple loci simultaneously. In wild apomictic taxa, this coordinated deregulation is hypothesized to be influenced by global regulatory changes resulting from hybridization and/or polyploidy (Grossniklaus, 2001, From sexuality to apomixis: Molecular and genetic approaches, In: The flowering of apomixis: From Mechanisms to Genetic Engineering, 168-211).

Recent reports analyse the gene expression of apomeiosis, that means unreduced gamete formation, in microdissected ovules of Boechera, and were able to identify quite a large number of differentially expressed alleles between sexual and apomeiotic ovules in a particular stage of the development, namely the megaspore mother cell (MMC) stage. Further studies focussed on heterochrony of gene expression patterns over a series of developmental stages in sexual and apomeiotic ovules (Sharbel et al., 2009, The Plant Journal, 58, 870-882, Sharbel et al., 2010, The Plant Cell, 22, 655-671). However, although the state of the art expectedly show that apomictic and sexual ovules are characterised by specific molecular signatures, it does not provide any clue on how to induce apomixis in a desired plant in a reliable and foreseeable manner, in particular by means of conventional gene transfer techniques.

In fact, one of the main difficulties in identifying the molecular genetic mechanisms controlling apomixis is that the genomes of virtually all apomicts are both polyploidy and hybrid in nature. Although considerable efforts, including in-depth functional molecular analyses, have been undertaken to analyse the molecular framework underlying apomictic phenomena, so far it still remains a challenge to control separately for the influences of either effect, both of which can have diverse regulatory consequences.

Engineering apomixis to a controllable, more reproducible trait would provide many advantages in plant improvement and cultivar development. Apomixis would provide for true-breeding, seed propagated hybrids. Harnessing apomixis would, thus, greatly facilitate and accelerate the ability of plant breeders to fix and faithfully propagate genetic heterozygosity and associated hybrid vigour in crop plants. Moreover, apomixis could shorten and simplify conventional breeding processes so that selfing and progeny testing to produce or stabilize a desirable gene combination could be eliminated.

The controlled use of apomixis would therefore certainly simplify commercial hybrid seed production. In particular, the need for physical isolation of commercial hybrid production fields would be eliminated, available land could be used to grow hybrid seed instead of dividing space between pollinators and male sterile lines and finally the need to maintain parental line seed stocks would be eliminated.

Apomixis would provide for the use as cultivars of genotypes with unique gene combinations since apomictic genotypes breed true irrespective of heterozygosity. Genes or groups of genes could thus be fixed in super genotypes. Every superior apomictic genotype from a sexual-apomictic cross would have the potential to be a cultivar. Apomixis would therefore allow plant breeders to develop cultivars with specific stable traits for such characters as height, seed and forage quality and maturity.

Thus, the application of apomixis in agriculture is considered an important enabling technology that would greatly facilitate the fixation and faithful propagation of genetic heterozygosity and associated hybrid vigor in crop plants (Spillane, 2004, Nat Biotech 22(6), 687-691).

All these potential benefits which rely on the production of seed via apomixis are presently, however, unrealized, to a large extent because of the problem of engineering apomictic capacity into plants of interest.

US 2002/0069433 A1 discloses methods for increasing the probability of vegetative reproduction of a new plant generation wherein a gene which encodes a protein acting in the signal transduction cascade triggered by the somatic embryogenesis receptor kinase is transgenically expressed. US 2008/0155712 A1 discloses processes for identifying in a plant, in particular maize, sequences responsible for apomictic development, in particular by genome mapping. WO 99/35258 A1 discloses nucleic acid markers for an apospory specific genomic region from the genus *Pennisetum*. U.S. Pat. No. 7,541,514 B2 discloses methods for producing apomictic plants from sexual plants by selecting, collecting and breeding specific plant lines.

None of said disclosures provide means, in particular polynucleotides, which can easily be used in gene transfer methods to obtain in a controllable and inexpensive way apomixis in plants.

The technical problem underlying the present invention is therefore to provide means and methods to overcome the above-identified problems, in particular to provide means and methods to introduce apomixis into a plant for instance by means of recombinant gene technology, in particular by means of recombinant DNA transfer technology, in particular to provide means and methods to induce apomixis in plants, in particular in a controllable, foreseeable, reliable, easy and cost-effective way.

The present invention solves its underlying problem by the provision of the teaching of the independent claims, in particular by the provision of nucleic acid molecules, in particular isolated nucleic acid molecules, useful for inducing apomixis in plants, plant cells and plant parts containing said sequence as well as methods to induce apomixis in plants, methods to produce apomictic plants and uses thereof. In particular, the present invention solves its underlying technical problem by the provision of an isolated nucleic acid molecule for use in inducing apomixis in a plant comprising a polynucleotide which is selected from the group consisting of a) the polynucleotide defined in any one of SEQ ID No. 22 to 62, or a fully complementary strand thereof, b) a polynucleotide encoding a polypeptide with the amino acid sequence defined in any one of SEQ ID No. 1 to 21, or a fully complementary strand thereof, and c) a polynucleotide variant having a degree of sequence identity of more than 70% to the nucleic acid sequence defined in a) or b), or a fully complementary strand thereof, preferably wherein the sequence identity is based on the entire sequence. Preferably, the sequence identity is determined by BLAST analysis, preferably in the NCBI database, in particular by GAP analysis using Gap Weight of 50 and Length Weight of 3.

The present invention relates in a particularly preferred embodiment to an isolated nucleic acid molecule which comprises a polynucleotide coding for a protein capable of inducing apomixis in a plant, preferably in a plant ovule, preferably exhibiting an exonuclease activity in a plant ovule, which is selected from the group consisting of a1) the polynucleotide defined in any one of SEQ ID No. 22 to 62, in particular 23, 25, 27, 28, 29, 30, 33, 35, 37, 38, 40, 41, 43, 44, 47, 50 or 53, or a fully complementary strand thereof, b1) a polynucleotide encoding a polypeptide with the amino acid sequence defined in any one of SEQ ID No. 1 to 21, preferably SEQ ID No. 4 to 9, SEQ ID No. 13 to 15 or SEQ ID No. 19 to 21, or a fully complementary strand thereof, and c1) a polynucleotide variant having a degree of sequence identity of more than 30%, 40%, 50% or, preferably 70% to the nucleic acid sequence defined in a1) or b1), or a fully complementary strand thereof, preferably wherein the sequence identity is based on the entire sequence. Preferably, the sequence identity is determined by BLAST analysis, preferably in the NCBI database, in particular by GAP analysis using Gap Weight of 50 and Length Weight of 3 or any other suitable analysis.

The nucleic acid molecules of the present invention represent the so-called apollo gene, which means "Apomixis linked locus", or are essential and specific parts thereof. Said gene, in particular its coding sequence, codes for the apollo protein which upon expression in the plant ovule leads to the production of apomictic seed.

The present invention also relates in a preferred embodiment to the above-identified protein-coding polynucleotide which is in particular characterised by the presence of at least one specific duplicated marker sequence in an exon, namely the fifth exon, of said sequence and which represents a nucleotide stretch duplication. Preferably, said duplicated marker nucleotide sequence is given in SEQ ID No. 64 and its corresponding amino acid sequence in SEQ ID No. 63.

Accordingly, the present invention also relates to an isolated nucleic acid molecule, which comprises a polynucleotide coding for a protein capable of inducing apomixis in a plant, preferably in a plant ovule, preferably exhibiting an exonuclease activity in a plant ovule, wherein the polynucleotide comprises a nucleic acid sequence selected from the group consisting of a2) the polynucleotide defined in any one of SEQ ID No. 22, 23, 27, 28, 32 or 33, preferably 23, 28 or 33, or a fully complementary strand thereof, b2) a polynucleotide encoding a polypeptide with the amino acid sequence defined in any one of SEQ ID No. 4, 5 or 6 or a fully complementary strand thereof, and c2) a polynucleotide variant having a degree of sequence identity of more than 30%, 40%, 50% or, preferably 70% to the nucleic acid sequence defined in a2) or b2), or a fully complementary strand thereof, preferably wherein the sequence identity is based on the entire sequence. Preferably, the sequence identity is determined by BLAST analysis, preferably in the NCBI database, in particular by GAP analysis using Gap Weight of 50 and Length Weight of 3 or any other suitable analysis.

The present invention advantageously provides polynucleotides, in particular polynucleotides coding for a protein capable of inducing apomixis in a plant, namely the apollo protein, and polynucleotides capable of functioning as regulatory elements for said coding sequence, in isolated and purified form. Furthermore, the present invention provides the teaching that plants, in particular their genome, comprise endogenously nucleotide sequences, hereinafter also called "polynucleotide" or "polynucleotide sequence", coding said apollo protein capable of inducing apomixis and its regulatory elements, hereinafter also called "endogenously present polynucleotide coding a protein capable of inducing apomixis in a plant". Thus, both the coding and the regulatory sequences as specified for instance in SEQ ID No. 37, 40, 43, 46, 49 or 52 are usually endogenously present in various allelic states in their natural and original genome environment in a plant, particularly in Brassicaceae, preferably Boechera, and are responsible for the development of a sexual or apomictic phenotype in the plant. According to the findings of the present invention in the naturally occurring sexually propagating plant, said nucleotide sequences in their sexual allelic state, such as in SEQ ID No. 46, 49 or 52, however, are in the ovule of said plant repressed, that means not expressed, thereby preventing apomixis. In contrast, said polynucleotide in its apomictic allelic state, such as in SEQ ID No. 37, 40 or 43 is induced, that means is expressed in the ovule of a plant propagating asexually, that means an apomictic plant.

In particular, the invention is based on the teaching that in a plant ovule of a sexually propagating plant the endogenously present gene coding for the apollo protein with an apomixis-inducing capacity is suppressed or inactivated in said tissue and therefore needs to be activated in order to produce an apomictic plant. Both in sexually and apomictic plants the coding regions of the apollo gene in its apomictic and sexual allelic form, are functionally equivalent. Differences in their expression are due to their different regulatory elements preferably as specified in SEQ ID No. 57 to 62 and 65. In particular, apomictic regulatory elements, preferably those as identified in SEQ ID No. 55, 57, 58 and 59, are in particular characterised by the presence of a 20 base pair promoter insertion, in particular that of SEQ ID No. 65, which leads to an ovule expression, i.e. expression in the ovule, of a coding element linked to said regulatory element. The sexual regulatory element of the present invention is in particular characterised by the absence of such a promoter insert of SEQ ID No. 65 and is represented in particular by a regulatory element as given in SEQ ID No. 56, 60, 61 or 62 and provides a somatic gene expression, but not an expression in the ovule, possibly due to being suppressed in said tissue.

In particular, the invention therefore provides the teaching to modify, in particular activate or induce, that means to get said sequences expressed in order to achieve a plant of a desired phenotype, in particular an apomictic phenotype. This can preferably be achieved by either transforming a plant with expressible coding sequences for the apollo protein of the present invention for its expression in the plant, in particular a plant ovule, so as to provide the apomictic phenotype to said plant and its progeny or by transforming a plant with regulatory sequences of the present invention inducing the expression of the endogenously present polynucleotide coding for the present protein capable of inducing apomixis, that means the apollo protein in said plant. Furthermore, the present invention achieves its aim of providing an apomictic plant by transforming a plant with any nucleotide sequence, in particular any DNA molecule, which structurally interferes with the repressed regulatory element of an endogenously present apollo gene, in particular polynucleotide sequence, capable of expressing a protein capable of inducing apomixis in the plant, thereby derepressing said apollo gene and allowing its expression in a plant ovule so as to produce an apomictic plant.

Thus, the present invention foresees to introduce an exogenous polynucleotide, in particular transgenic, coding sequence for the apollo protein into a plant, so as to express said coding sequence in the plant ovule. The invention also foresees in an alternative embodiment to activate, that means to induce the expression of an endogenously present apollo gene, in particular polynucleotide coding for the apollo protein capable of inducing apomixis, that means to induce the endogenously present apollo gene in the plant.

In the context of the present invention, the term "inducing the expression of a gene—or polynucleotide—coding for protein capable of inducing apomixis" therefore refers to the activation, hereinafter also termed derepression, of a regulatory element governing the expression of said coding sequence, that means refers to the activation of expression allowing the production of a functional apollo protein in the plant ovule.

Thus, the present invention provides advantageous means and methods to induce apomixis in a plant. The polynucleotides of the present invention, in particular those which code for a protein capable of inducing apomixis, can be used to be transformed in a plant cell so as to produce a plant which comprises said exogenously introduced polynucleotide, expresses said polynucleotide in a plant ovule and thereby produces an apomictic phenotype and apomictic plant. This can in a particularly preferred embodiment be achieved by using the polynucleotides of the present invention, preferably defined in any one of SEQ ID No. 22 to 54, preferably 23, 25, 27, 28, 29, 30, 33, 35, 37, 38, 40, 41, 43, 44, 47, 50 or 53, in particular 23, 25, 28, 30, 33, 35, 38, 41, 44, 47, 50 or 53, coding for a protein capable of inducing apomixis in a plant ovule, preferably defined in any one of SEQ ID No. 4 to 21, preferably SEQ ID No. 4 to 9, SEQ ID No. 13 to 15 or SEQ ID No. 19 to 21, under control of a constitutively expressing promoter or a promoter providing an ovule-specific expression in the ovule.

Thus, in one preferred aspect of the present invention the isolated nucleic acid molecules comprise polynucleotides, in particular polynucleotides as specifically disclosed herein or polynucleotide variants, for use in inducing apomixis, which code for a protein capable of inducing apomixis in a plant, in particular in a plant ovule, in particular code for a protein with a specific exonuclease activity capable of inducing apomixis, in particular apomeiosis, in a plant ovule, and wherein said specific polynucleotides or variants thereof can advantageously be used to be transferred into a plant, in particular plant cell, be stably integrated in its genome and can preferably be expressed, in particular and most preferably in a constitutive manner, in the ovule of the obtained transformed plant in order to produce a transgenic apomictic plant, in particular transgenic plant, which produces apomictic seed. In a preferred embodiment of the present invention it is foreseen to transfer a polynucleotide of the present invention encoding a protein capable of inducing apomixis in a plant and being specified in any one of the consensus SEQ ID No. 1 to 9, preferably SEQ ID No. 4 to 9, most preferably SEQ ID No. 4 or 7, most preferably SEQ ID No. 5 or 8, most preferably SEQ ID No. 6 or 9 and in particular as specified in any one of the specific SEQ ID No. 10 to 21, preferably SEQ ID No. 13 to 15 or 19 to 21, into a plant so as to allow expression of said polynucleotide, preferably being under control of a constitutively or ovule-specific promoter, thereby producing the desired apollo protein in the ovule.

The present invention also provides polynucleotides which are capable of functioning as a regulatory element and which can be used to transform plant cells and whereby said polynucleotides capable of functioning as regulatory elements structurally modify the regulatory elements of the endogenously present genes which code for proteins capable of inducing apomixis so as to derepress, that means activate, the endogenously present regulatory elements of said genes thereby allowing the expression of the protein capable of inducing apomixis and producing plants with an apomictic phenotype. This particular approach is based on the findings of the present invention that the gene coding for the protein capable of inducing apomixis is present also in wild type plants, but is, however, not activated, that means is not induced and therefore is not expressed in the ovule of a sexually propagating plant. Without being bound by theory, in wild type sexually propagating plants the expression of the endogenously present gene coding for a protein capable of inducing apomixis is suppressed or inactivated, most likely due to suppressed regulatory elements of the protein-coding regions. Thus, the present invention foresees in one embodiment the introduction of regulatory elements which structurally interfere with the endogenously present and suppressed regulatory elements of a nucleotide sequence region coding for a protein capable of inducing apomixis in a plant ovule allows the reversion of the suppression of the regulatory elements and induces the expression of the coding sequence.

Accordingly, in a preferred embodiment a polynucleotide, in particular a specifically disclosed polynucleotide or polynucleotide variant of the present invention, in particular a regulatory element as specified in any one of SEQ ID No. 55 to 62 or 65, is transformed into a plant so as to modify the endogenously present regulatory element having a sequence as given in the sexual promoter given in any one of SEQ ID No. 56, 60, 61 or 62 of an endogenously present gene encoding the apollo protein capable of inducing apomixis in a plant so as to enable the expression of the endogenously present polynucleotide encoding the polypeptide capable of inducing apomixis in the plant, in particular the ovule.

Accordingly, the present invention provides isolated nucleic acid molecules, which comprise polynucleotides, that means the polynucleotides specifically disclosed herein or polynucleotide variants, for use in inducing apomixis, wherein the specific polynucleotides or polynucleotide variants are regulatory elements and are useful for inducing apomixis in a plant in so far as they allow a regulatable expression of coding sequences operably linked thereto in the plant ovule, in particular during ovule development in a plant. Thus, these regulatory elements provide an ovule non-suppressability to a coding sequence and provide the advantage of being capable to direct expression of coding sequences in the ovule of plants.

Thus, in a particularly preferred embodiment an induced mutation, for instance a recombination, duplication, deletion, insertion or inversion, of all or part of the endogenously present regulatory element for the coding sequence of the polypeptide capable of inducing apomixis in a plant ovule allows the expression of said polynucleotide consequently leading to apomixis in the plant.

The present invention also allows and enables the induction of apomixis in a plant by modifying, in particular inducing, hereinafter also called activating, the expression of the endogenously present regulatory elements of the endogenously present nucleotide sequence encoding a protein capable of inducing apomixis in a plant by structurally modifying said endogenously present regulatory elements for instance by mutating, in particular by insertion, deletion, duplication or inversion of said regulatory element. Said structural modification may preferably be achieved by any means for mutation, for instance radiation, use of chemical agents or of nucleotide sequences, in particular a DNA molecule, introduced into a plant cell, which means, in particular sequence, is capable of structurally interfering with said regulatory element and which sequence may be a transposon or any other sequence being able to interfere, for instance recombine or insert into said regulatory element in the ovule of a sexually propagating plant.

In a further embodiment, the present invention provides specific polynucleotides and polynucleotide variants which are capable of acting as regulatory elements, in particular promoters, which very specifically act in a regulatory manner in the ovule. In particular, in one preferred embodiment of such a regulatory element, hereinafter also called sexual promoter, said regulatory element is capable of being expressed in all somatic tissue of a transformed transgenic plant, but specifically not in the ovule of said plant. In another embodiment of such a regulatory element, hereinafter also called apo-promoter, of the present invention, said regulatory element is expressed in the somatic tissue of a transformed transgenic plant and is also expressed in the ovule of said plant. Thus, the present invention provides polynucleotides which in one embodiment allow a somatic gene expression excluding the ovule tissue, while in another embodiment an ovule gene expression is allowed. Said latter embodiment, namely the ovule expressing embodiment, being specified in any one of SEQ ID No. 55, 57, 58 or 59 is primarily characterised by a nucleotide sequence comprising a regulatory insert of twenty nucleotides with SEQ ID No. 65 in comparison to the firstly mentioned embodiment, namely the non-ovule expressing embodiment, lacking said insert and being specified in SEQ ID No. 56, 60, 61 or 62. Thus, in a particularly preferred embodiment the regulatory element of the present invention allowing expression in somatic tissue, but not in the ovule, that means the sexual promoter, is characterised by any one of SEQ ID No. 56, 60, 61 or 62. In a furthermore preferred embodiment of the present invention the regulatory element capable of being expressed in the ovule, in particular by being not suppressible or not suppressed, that means the apo-promoter, is characterised by SEQ ID No. 55, 57, 58 or 59.

Thus, the present invention relates in a further preferred embodiment to an isolated nucleic acid molecule, which comprises a polynucleotide, which polynucleotide is able to act as a regulatory element and is selected from the group consisting of a3) the polynucleotide defined in any one of SEQ ID No. 55 to 62 or 65, or a fully complementary strand thereof and b3) a polynucleotide variant having a degree of sequence identity of more than 30%, 40%, 50%, 60%, preferably 70% to the nucleic acid sequence defined in a3), or a fully complementary strand thereof, preferably wherein the sequence identity is based on the entire sequence. Preferably, the sequence identity is determined by BLAST analysis, preferably in the NCBI database, in particular by GAP analysis using Gap Weight of 50 and Length Weight of 3 or any other suitable analysis.

Thus, the present invention very advantageously allows the vegetative production of seed identical to the parent. In particular and preferably, the present nucleotide acid molecules can be transformed into a desired plant, for instance high yielding hybrids, in order to change their reproductive mode into apomictic seed production. Thus, high yielding hybrids can according to the present invention be used in seed production to multiply identical copies of said high yielding hybrid seed which would greatly reduce the cost for the seed production and in turn increases the number of genotypes which could commercially be offered. Further on, genes can be evaluated directly in commercial hybrids, since the progeny would not segregate saving the cumbersome backcrossing procedures. Apomixis can be used to stabilise desirable phenotypes even with complex traits such as hybrid vigor. Such traits can be maintained very easily and be multiplied via apomixis indefinitive. Further, the present invention provides the possibility to combine it with male sterility, advantageously preventing genetically engineered stabilised traits from being hybridised with undesired relatives.

The present invention provides a solution to the above-identified technical problem by providing specific isolated nucleic acid molecules which can be used for inducing apomixis in a plant, in particular in a plant ovule, preferably for inducing apomeiosis and/or parthenogenesis in a plant, preferably in a plant ovule.

These nucleic acid molecules of the present invention comprise in one preferred embodiment specific polynucleotides characterised by their ability to induce apomixis in a plant and by the presence of specific consensus nucleotide sequence patterns according to any one of SEQ ID No. 27, 28, 29, 30 or 31, in particular 27, 28, 29, 30, preferably 27 or 29, which represent nucleotide patterns present in all specifically disclosed apomixis-inducing alleles of the present invention.

In a further preferred embodiment the specific polynucleotides are the various apomixis-inducing alleles, which are specifically identified, isolated and characterised according to the present invention and are characterised in any one of SEQ ID No. 37 to 45.

The present invention is preferably characterised by providing polynucleotides and polypeptides in specific and in consensus forms. The consensus forms are generalised sequence motifs, that means patterns, being in one embodiment found in all of the polymorphic apollo genes identified and isolated according to the present invention, in particular are common to the coding sequence of all the different polymorphic forms including the apomictic and sexual forms. The consensus sequences are also given as generalised sequence motifs solely found in the apomictic polymorphic alleles or, in another embodiment, are solely found in the sexual polymorphic allelic forms isolated according to the present invention. The apomictic and sexual alleles can be classified by different consensus sequences for their regulatory elements and share the same consensus sequence for their coding regions. In the consensus sequence "Xaa" stands for any naturally occurring amino acid and "n" for any one of the nucleotides a, t, g or c.

The specific polynucleotides and polypeptides provided in the present invention are specifically isolated and analysed and display the consensus sequence pattern in exemplified form.

In a particularly preferred embodiment the present invention therefore relates to consensus and specific polynucleotides and polypeptides characterised in the following tables I to III.

TABLE I

Apollo-amino acid sequences (polypeptides)

| SEQ ID No. | type | subtype | characterisation | coded by SEQ ID No. |
|---|---|---|---|---|
| 1 | consensus | Global | Exonuclease domain | 26 |
| 2 | consensus | Apo | Exonuclease domain | 31 |
| 3 | consensus | Sex | Exonuclease domain | 36 |
| 4 | consensus | Global | protein with duplication | 22, 23 |
| 5 | consensus | Apo | protein with duplication | 27, 28 |
| 6 | consensus | Sex | protein with duplication | 32, 33 |
| 7 | consensus | Global | protein without duplication | 24, 25 |
| 8 | consensus | Apo | protein without duplication | 29, 30 |
| 9 | consensus | Sex | protein without duplication | 34, 35 |
| 10 | specific | Apo | A011a Exonuclease domain | 39 |
| 11 | specific | Apo | A043a Exonuclease domain | 42 |
| 12 | specific | Apo | A081a Exonuclease domain | 45 |
| 13 | specific | Apo | A011a Protein | 37, 38 |
| 14 | specific | Apo | A043a Protein | 40, 41 |
| 15 | specific | Apo | A081a Protein | 43, 44 |
| 16 | specific | Sex | S011a Exonuclease domain | 48 |
| 17 | specific | Sex | S355a Exonuclease domain | 51 |
| 18 | specific | Sex | S390a Exonuclease domain | 54 |

TABLE I-continued

Apollo-amino acid sequences (polypeptides)

| SEQ ID No. | type | subtype | characterisation | coded by SEQ ID No. |
|---|---|---|---|---|
| 19 | specific | Sex | S011a Protein | 46, 47 |
| 20 | specific | Sex | S355a Protein | 49, 50 |
| 21 | specific | Sex | S390a Protein | 52, 53 | legend:
A011a, A043a, A081a: apomictic *Boechera holboellii* alleles;
S011a, S355a,
S390a: sexual *Boechera holboellii* alleles "consensus" means consensus sequence, that means a general sequence motif present in more than one specific allele of the apollo gene with specifically identified positions for observed sequence deviations, namely nucleotide/amino acid polymorphisms. In amino acid sequences "Xaa" can be any naturally occurring amino acid. In nucleotide sequences "n" can be any of a, g, t or c, in introns "n" can additionally designate a missing nucleotide.

"specific" means a specifically isolated polymorphic allele with sequenced or deduced nucleotide and amino acid sequence.

"Global" means a consensus sequence both for apomictic and sexual apollo gene or protein.

"Apo" means apomictic apollo gene or protein.

"Sex" means sexual apollo gene or protein.

"protein" means apollo protein.

"Exonuclease domain" means the fragment of the apollo protein in which the specific biologically active DEDDh 3'-5' exonuclease activity is located.

"duplication" means a duplicated marker sequence optionally present in the coding region of the apomictic and sexual allele of the apollo gene and specified in SEQ ID No. 63 (amino acid) and 64 (nucleotide).

TABLE II

Apollo-protein coding polynucleotides

| SEQ ID No. | type | subtype | characterisation |
|---|---|---|---|
| 22 | consensus | Global | genomic with duplication |
| 23 | consensus | Global | coding with duplication |
| 24 | consensus | Global | genomic without duplication |
| 25 | consensus | Global | coding without duplication |
| 26 | consensus | Global | Exonuclease domain |
| 27 | consensus | Apo | genomic with duplication |
| 28 | consensus | Apo | coding with duplication |
| 29 | consensus | Apo | genomic without duplication |
| 30 | consensus | Apo | coding without duplication |
| 31 | consensus | Apo | Exonuclease domain |
| 32 | consensus | Sex | genomic with duplication |
| 33 | consensus | Sex | coding with duplication |
| 34 | consensus | Sex | genomic without duplication |
| 35 | consensus | Sex | coding without duplication |
| 36 | consensus | Sex | Exonuclease domain |
| 37 | specific | Apo | A011a genomic |
| 38 | specific | Apo | A011a coding |
| 39 | specific | Apo | A011a Exonuclease domain |
| 40 | specific | Apo | A043a genomic |
| 41 | specific | Apo | A043a coding |
| 42 | specific | Apo | A043a Exonuclease domain |
| 43 | specific | Apo | A081a genomic |
| 44 | specific | Apo | A081a coding |
| 45 | specific | Apo | A081a Exonuclease domain |
| 46 | specific | Sex | S011a genomic |
| 47 | specific | Sex | S011a coding |
| 48 | specific | Sex | S011a Exonuclease domain |
| 49 | specific | Sex | S355a genomic |
| 50 | specific | Sex | S355a coding |
| 51 | specific | Sex | S355a Exonuclease domain |

TABLE II-continued

Apollo-protein coding polynucleotides

| SEQ ID No. | type | subtype | characterisation |
|---|---|---|---|
| 52 | specific | Sex | S390a genomic |
| 53 | specific | Sex | S390a coding |
| 54 | specific | Sex | S390a Exonuclease domain | legend:
see table I;
"genomic" means genomic DNA sequence, preferably including regulatory elements, exons and introns.
"coding" means solely the coding DNA sequence which codes the full length apollo protein.

TABLE III

Apollo-regulatory polynucleotides, peptides and inserts

| SEQ ID No. | type | subtype | characterisation |
|---|---|---|---|
| 55 | consensus | Apo | Promoter |
| 56 | consensus | Sex | Promoter |
| 57 | specific | Apo | A011a promoter |
| 58 | specific | Apo | A043a promoter |
| 59 | specific | Apo | A081a promoter |
| 60 | specific | Sex | S011a promoter |
| 61 | specific | Sex | S355a promoter |
| 62 | specific | Sex | S390a promoter |
| 63 | specific | Apo/Sex | duplication, amino acids |
| 64 | specific | Apo/Sex | duplication, DNA |
| 65 | specific | Apo | promoter insert | legend:
see table I;
"promoter insert": regulatory insertion of 20 bp found in apo-promoters The present invention provides in one embodiment global consensus genomic sequences, in particular those of SEQ ID No. 22 and 24 which represent nucleotide sequence patterns found in the apomictic and sexual alleles of the present invention in so far as the nucleotide sequences given are to be found in both types of alleles.

Thus, in a particularly preferred embodiment of the present invention polynucleotides coding for the apollo protein are provided which are characterised by any one of the polynucleotide sequences given in SEQ ID No. 23, 25 to 31, 33, 35 to 45, 47, 48, 50, 51, 53 or 54 which are consensus and specific sequences found in apomictic and sexual alleles and which code for the consensus or specific apollo protein of the present invention of any one of SEQ ID No. 1 to 21, preferably of SEQ ID No. 4 to 9, 13 to 15 or 19 to 21 or an essential part thereof, namely the exonuclease domain of SEQ ID No. 1 to 3, 10 to 12 or 16 to 18. Most preferred are polynucleotides identified in Table I coding for the consensus apollo proteins or essential parts thereof, namely any one of SEQ ID No. 1 to 21, preferably 4, 5, 6, 7, 8, 9, 13, 14, 15, 19, 20 or 21, in particular 4, 5, 6, 7, 8 or 9. In a preferred embodiment polynucleotides comprising any one of SEQ ID No. 23 or 25, 26, 27, 28, 29, 30, 31, 33, 35, 36, 37, 38, 39, 40, 41, 42, 43, 44, 45, 47, 48, 50, 51, 53 or 54 are preferred all of them comprising coding sequences for the apollo protein, but no sexual-specific regulatory elements being suppressible in a plant ovule. Thus, these sequences do not comprise the sexual promoters with SEQ ID No. 56 or any one of 60, 61 and 62, which are in particular lacking the promoter insert of SEQ ID No. 65.

However, also the polynucleotide sequences comprising sexual regulatory elements such as the polynucleotides of SEQ ID No. 32, 34, 46, 49, 52, 56, 60, 61 or 62 are preferred as comprising regulatory elements useful for providing suppressibility in plant ovule expression or for mutating endogenously present apollo genes so as to induce apomixis. These polynucleotides can, in a preferred embodiment, be modified, in particular to contain the apomictic promoter insert of SEQ ID No. 65 thereby resulting in a regulatory element being expressed in the ovule thereby not being suppressed anymore in the ovule of a plant.

The present invention also provides functionally equivalent polynucleotides for use in inducing apomixis in a plant, in particular in a plant ovule, preferably for inducing apomeiosis and/or parthenogenesis in a plant, preferably in a plant ovule, which do not exactly show the specific nucleotide sequence of said specific nucleotide sequence patterns or apomixis-inducing alleles and in particular given in the sequence identity protocols given herein, but which do exhibit slight deviations therefrom and which are in the context of the present invention termed "polynucleotide variants". Such polynucleotide variants are allelic, polymorphic, mutated, truncated or prolonged variants of the polynucleotides defined in the present sequence identity protocols and which therefore show deletions, insertions, inversions or additions of nucleotides in comparison to the polynucleotides defined in the present sequence identity protocol. Thus, polynucleotide or polypeptide variants of the present invention, hereinafter also termed "functional equivalents" of a polynucleotide or polypeptide, have a structure and a sufficient length to provide the same biological activity, that means the same capability to induce apomixis in the plant as the specifically disclosed polynucleotides or polypeptides of the present invention.

A polypeptide coded by a polynucleotide variant of the present invention is—in case its amino acid sequence is altered in comparison to the amino acid sequence of the polypeptide coded by the polynucleotide of the present invention—termed a polypeptide variant. However, due to the degeneracy of the genetic code a polynucleotide variant not necessarily codes in any case for a polypeptide variant but may also code a polypeptide of the present invention.

The term "variant" refers to a substantially similar sequence of the specifically disclosed polynucleotides or polypeptides of the present invention. Generally, polynucleotide variants of the invention will have at least 30%, 40%, 50%, 60%, 65%, or 70%, preferably 75%, 80% or 90%, more preferably at least 91%, preferably at least 92%, preferably at least 93%, preferably at least 94%, preferably at least 95%, preferably at least 96%, preferably at least 97% and most preferably at least 98% or at least 99% sequence identity to the present polynucleotides, in particular those representing the present apomixis-inducing alleles, in particular its coding sequence, wherein the % sequence identity is based on the entire sequence. Preferably, the sequence identity is determined by BLAST analysis, preferably in the NCBI database, in particular by GAP analysis using Gap Weight of 50 and Length Weight of 3 or any other suitable analysis.

Generally, polypeptide sequence variants of the invention will have at least about 30%, 40%, 50%, 55%, 60%, 65%, 70%, 75% or 80%, preferably at least about 85% or 90%, and more preferably at least about 91%, preferably at least 92%, preferably at least 93%, preferably at least 94%, preferably at least 95%, preferably at least 96%, preferably at least 97% and most preferably at least 98% or at least 99% sequence identity to the present protein capable of inducing apomixis, wherein the % sequence identity is based on the entire sequence. Preferably, the sequence identity is determined by BLAST analysis, preferably in the NCBI database, in particular by GAP analysis using Gap Weight of 12 and Length Weight of 4 or any other suitable analysis.

According to the present invention a number of amino acids of the present polypeptides can be replaced, inserted or deleted without altering a protein's function. The relationship between proteins is reflected by the degree of sequence identity between aligned amino acid sequences of individual proteins or aligned component sequences thereof.

For sequence alignments and the determination of sequence identities in the context of the present invention various programs and algorithms can be used, such as the Wilbur-Lipman (Wilbur W J, Lipman D J, (1983), Rapid similarity searches of nucleic acid and protein data banks. Proc Natl Acad Sci USA 80:726-730), the Lipman-Pearson (Lipman D J, Pearson W R (1985), Rapid and sensitive protein similarity searches. Science 227:1435-1441), the Martinez-NW (Needleman-Wunsch) algorithms (Martinez H (1983), An efficient method for finding repeats in molecular sequences. Nucleic Acids Res 11:4629-4634; Needleman S B and Wunsch C D (1970), A general method applicable to the search for similarities in the amino acid sequences of two proteins. J Mol Biol 48:444-453) or a combination thereof. The Wilbur-Lipman method is preferably used with the default ones provided by the program (ktuple=3; Gap Penalty=3; window=20). As the instructions of the program MegAlign describes, the Wilbur-Lipman method constructs tables of K-tuples to find regions of similarity between two DNA sequence pairs using the method of Wilbur and Lipman (1983). This method reads the sequences, builds case structures of the K-tuples, finds the diagonals and matches, and creates the finished alignment. The method of Martinez-NW uses two alignment methods in succession. An approach described by Martinez (Martinez H (1983), An efficient method for finding repeats in molecular sequences. Nucleic Acids Res 11:4629-4634) identifies regions of perfect match. The Needleman-Wunsch (Needleman S B and Wunsch C D (1970), A general method applicable to the search for similarities in the amino acid sequences of two proteins. J Mol Biol 48:444-453) method then optimizes the fit in between perfect matches. The conditions of the alignment were the default ones provided by the program (Minimum Match=9; Gap Penalty=1.10; Gap Length Penalty=0.33). The program preferably used for calculating the algorithms can be MegAlign (DNASTAR Lasergene version 9 Core Suite (DNASTAR, Inc., 3801 Regent Street, Madison, Wis. 53705, USA).

Dynamic programming algorithms yield different kinds of alignments. Algorithms as proposed by Needleman and Wunsch and by Sellers align the entire length of two sequences providing a global alignment of the sequences. The Smith-Waterman algorithm yields local alignments. A local alignment aligns the pair of regions within the sequences that are most similar given the choice of scoring matrix and gap penalties. This allows a database search to focus on the most highly conserved regions of the sequences. It also allows similar domains within sequences to be identified. To speed up alignments using the Smith-Waterman algorithm both BLAST (Basic Local Alignment Search Tool) and FASTA place additional restrictions on the alignments.

Within the context of the present invention alignments can be performed using BLAST, a set of similarity search programs designed to explore all of the available sequence databases regardless of whether the query is protein or DNA. Version BLAST 2.2 (Gapped BLAST) of this search tool has been made publicly available (currently on the world wide web at "ncbi.nlm.nih.gov/BLAST or internet at blast.ncbi.nlm.nih.gov. It uses a heuristic algorithm which seeks local as opposed to global alignments and is therefore able to detect relationships among sequences which share only isolated regions. The scores assigned in a BLAST search have a well-defined statistical interpretation. Particularly useful within the scope of the present invention are the blastp program allowing for the introduction of gaps in the local sequence alignments and the PSI-BLAST program, both programs comparing an amino acid query sequence against a protein sequence database, as well as a blastp variant program allowing local alignment of two sequences only.

Sequence alignments, preferably using BLAST, can also take into account whether the substitution of one amino acid for another is likely to conserve the physical and chemical properties necessary to maintain the structure and function of a protein or is more likely to disrupt essential structural and functional features. For example non-conservative replacements may occur at a low frequency and conservative replacements may be made between amino acids within the following groups: (i) serine and threonine; (ii) glutamic acid and aspartic acid; (iii) arginine and lysine; (iv) asparagine and glutamine; (v) isoleucine, leucine, valine and methionine; (vi) phenylalanine, tyrosine and tryptophan (vii) alanine and glycine.

Such sequence similarity is quantified in terms of percentage of positive amino acids, as compared to the percentage of identical amino acids.

The polynucleotide or polypeptide variants of the present invention, however, are in spite of their structural deviations also capable of exhibiting the same or essentially the same biological activity as the polynucleotides or polypeptides defined in the sequence identity protocols of the present invention.

In the context of the present invention the term "biological activity" refers to the capability of the polynucleotide or polypeptide of the present invention or their variants to induce apomixis in a plant. The term "to induce apomixis in a plant" refers to the capability of a polynucleotide or polypeptide or variant thereof to induce an asexual production of viable seed in a plant, in particular in the ovule of a plant, in particular the capability to induce apomeiosis or parthenogenesis or both apomeiosis and parthenogenesis in a plant ovule, in particular by coding or exerting an exonuclease activity in the ovule.

In one embodiment of the present invention a polynucleotide of the present invention is able to induce apomixis in a plant ovule by activating or derepressing, in particular by structurally changing, a regulatory element of an endogenously present gene coding for a protein with an ovule exonuclease activity, preferably ovule-specific exonuclease activity, capable of inducing apomixis in a plant. Such a gene is in particular characterised by having a polynucleotide sequence according to the present invention and thereby allowing, upon derepression, that means induction, the expression of said endogenously coded protein with an ovule exonuclease activity, preferably an ovule-specific exonuclease activity, capable of inducing apomixis in the plant.

In a particularly preferred embodiment the biological activity exerted by a polypeptide of the present invention, that means a protein capable of inducing apomixis in a plant, is a specific exonuclease activity characterised by expression at least in the ovule, preferably by an ovule specificity, in so far as its expression is activated in the ovule, preferably specifically in the ovule, of an apomictic plant and repressed or inactivated in a sexual plant.

In particular, the present protein, namely the apollo protein, which is capable of inducing apomixis in a plant, in particular a plant ovule and having a specific exonuclease activity appears to be, without being bound by theory, a DEDD 3→5' exonuclease, also termed a DNA Q protein, which preferably is characterised by four acidic residues, namely three aspartats (D) and glutamate (E) distributed in three separate sequence segments, namely exo I, exo II and exo III (Moser et al., Nucl. Acids. Res 25 (1997), 5110-5118). Furthermore, these proteins are characterised by either a tyrosine (y) or histidine (h) amino acid located at its active side determinative for being a DEDDy or DEDDh protein. In a preferred embodiment, the present polypeptide capable of inducing apomixis in a plant ovule is a DEDDh exonuclease, preferably comprising the amino acid sequence as given in any one of SEQ ID No. 1 to 3, 10 to 12 or 16 to 18, preferably catalysing the excision of nucleoside monophosphates at the DNA or RNA termini in the 3'-5' direction. In particular, the present exonuclease is a plant DEDDh exonuclease.

In a particularly preferred embodiment the specific biological activity performed by the polypeptide capable of inducing apomixis in the plant ovule in said plant ovule, that means the apollo protein, appears to be a meiosis-modifying, in particular meiosis-altering, changing or varying activity, in particular is a meiosis-inhibiting activity thereby preventing the reduction of chromosome number in the germ cells.

The isolated nucleic acid molecules of the present invention may be present in isolated form. The isolated nucleic acid molecules of the present invention may, however, also be combined with other nucleic acid molecules, for instance regulatory elements or vectors, thereby forming another molecule comprising not solely the nucleic acid molecule of the present invention. In this case the "nucleic acid molecule" of the present invention is also termed a "nucleic acid sequence" of the present invention.

In the context of the present invention the term "comprising" is understood to have the meaning of "including" or "containing" which means that one first entity contains a second entity, wherein said first entity may in addition to the second entity further contain a third entity. Thus, in particular, the term "a nucleic acid molecule comprising a polynucleotide" means that the nucleic acid molecule of the present invention contains a polynucleotide or a polynucleotide variant of the present invention, but may in addition contain other nucleotides or polynucleotides. In a particular preferred embodiment the term "comprising" as used herein is also understood to mean "consisting of" thereby excluding the presence of other elements besides the explicitly mentioned element. Thus, the present invention also relates to nucleic acid molecules which consist of polynucleotides or polynucleotide variants of the present invention, meaning that the nucleic acid molecule is only composed of the polynucleotide or polynucleotide variant of the present invention and does not comprise any further nucleotides, polynucleotides or other elements. According to this embodiment, the nucleic acid molecule of the present invention is the polynucleotide or polynucleotide variant of the present invention.

Both, the nucleic acid molecule of the present invention and the polynucleotide comprised therein do exhibit the desired biological activity of being capable of inducing apomixis.

The term "apomixis" refers to the replacement of the normal sexual reproduction by asexual reproduction, that means preferably reproduction without fertilisation of the egg cell, in particular that means only fertilisation of the central cell which is a pseudogamous event, in particular without any fertilisation, in particular the term refers to asexual reproduction through seeds, leading to apomictically produced off-springs or progeny genetically identical to the parent plant, in particular the female plant.

The term "gene" refers to a coding nucleotide sequence and associated regulatory nucleotide sequences. The coding sequence is transcribed into RNA, which depending on the specific gene, will be mRNA, rRNA, tRNA, snRNA, sense RNA or antisense RNA. Examples of regulatory sequences, hereinafter also termed regulatory elements, are promoter sequences, 5' and 3' untranslated sequences and termination sequences. Further elements that may be present are, for example, introns or enhancers. A structural gene may constitute an uninterrupted coding region or it may include one or more introns bounded by appropriate splice junctions. The structural gene may be a composite of segments derived from different sources, naturally occurring or synthetic.

The gene to be expressed may be modified in that known mRNA instability motifs or polyadenylation signals are removed or codons which are preferred by the plant into which the sequence is to be inserted may be used.

The present invention also relates to the present nucleic acid molecules, in particular a polynucleotide or polynucleotide variant of the present invention, in particular a DNA sequence, wherein said nucleic acid molecule or sequence encodes a polypeptide capable of inducing apomixis, in particular in a plant, preferably plant ovule, and having, preferably comprising, the amino acid sequence depicted in SEQ ID No. 1, 2, 3, 10, 11, 12, 16, 17 or 18, or a polypeptide variant thereof, that means a functional equivalent of a polypeptide of the present invention, preferably a polypeptide being in terms of biological activity similar thereto. The present invention, thus, also provides a polypeptide variant of the present invention, in particular having a length of at least 150, at least 200, at least 250, at least 300, at least 350, at least 400, at least 450, at least 500 amino acids which after alignment reveals at least 30% or 40% and preferably at least 50%, at least 60%, at least 70%, at least 80%, at least 90%, at least 95%, at least 99% or more sequence identity with the, preferably full-length, polypeptide of the present invention, in particular as characterised in any one of SEQ ID No. 1 to 21, preferably 4, 5, 6, 7, 8, 9, 13, 14, 15, 19, 20 or 21.

The terms "protein" and "polypeptide" are used interchangeably and refer to a molecule with a particular amino acid sequence comprising at least 20, 30, 40, 50 or 60 amino acid residues.

The term "polypeptide" thus means proteins of the present invention and variants thereof, in particular protein fragments, modified proteins, amino acid sequences and synthetic amino acid sequences. According to the present invention the polypeptide can be glycosylated or not.

A polypeptide variant of the present invention which is truncated is also termed a "fragment" of the present invention. Thus, the term "fragment" refers to a portion of a polynucleotide sequence or a portion of a polypeptide, that means an amino acid sequence of the present invention and hence polypeptide encoded thereby. Fragments of a polynucleotide sequence such as SEQ ID No. 26, 31, 36, 39, 42, 45, 48, 51 or 54, may encode polypeptide fragments that retain the biological activity of the polypeptide of the present invention, such as given in any one of SEQ ID No. 1, 2, 3, 10, 11, 12, 16, 17 or 18. Alternatively, fragments of a polynucleotide sequence that are useful as hybridization probes generally do not encode fragments of a polypeptide retaining biological activity. Fragments of a polynucleotide sequence are generally greater than 20, 30, 50, 100, 150, 200 or 300 nucleotides and up to the entire nucleotide sequence encoding the polypeptide of the present invention. Generally, the fragments have a length of less than 1000 nucleotides and preferably less than 500 nucleotides. Fragments of the invention include antisense sequences used to decrease expression of the present polynucleotides. Such antisense fragments may vary in length ranging from at least 20 nucleotides, 50 nucleotides, 100 nucleotides, up to and including the entire coding sequence.

The term "regulatory element" refers to a sequence, preferably a nucleotide sequence, located upstream (5'), within and/or downstream (3') to a nucleotide sequence, preferably a coding sequence, whose transcription and expression is controlled by the regulatory element, potentially in conjunction with the protein biosynthetic apparatus of the cell. "Regulation" or "regulate" refer to the modulation of the gene expression induced by DNA sequence elements located primarily, but not exclusively upstream (5') from the transcription start of the gene of interest. Regulation may result in an all or none response to a stimulation, or it may result in variations in the level of gene expression.

A regulatory element, in particular DNA sequence, such as a promoter is said to be "operably linked to" or "associated with" a DNA sequence that codes for a RNA or a protein, if the two sequences are situated and orientated such that the regulatory DNA sequence effects expression of the coding DNA sequence.

A "promoter" is a DNA sequence initiating transcription of an associated DNA sequence, in particular being located upstream (5') from the start of transcription and being involved in recognition and being of the RNA-polymerase. Depending on the specific promoter region it may also include elements that act as regulators of gene expression such as activators, enhancers, and/or repressors.

A "3' regulatory element" (or "3' end") refers to that portion of a gene comprising a DNA segment, excluding the 5' sequence which drives the initiation of transcription and the structural portion of the gene, that determines the correct termination site and contains a polyadenylation signal and any other regulatory signals capable of effecting messenger RNA (mRNA) processing or gene expression. The polyadenylation signal is usually characterised by effecting the addition of polyadenylic acid tracts to the 3' end of the mRNA precursor. Polyadenylation signals are often recognised by the presence of homology to the canonical form 5'-AATAAA-3'.

The term "coding sequence" refers to that portion of a gene encoding a protein, polypeptide, or a portion thereof, and excluding the regulatory sequences which drive the initiation or termination of transcription.

The gene, coding sequence or the regulatory element may be one normally found in the cell, in which case it is called "autologous", or it may be one not normally found in a cellular location, in which case it is termed "heterologous" or "transgenic".

A "heterologous" gene, coding sequence or regulatory element may also be autologous to the cell but is, however, arranged in an order and/or orientation or in a genomic position or environment not normally found or occurring in the cell in which it is transferred.

The term "vector" refers to a recombinant DNA construct which may be a plasmid, virus, autonomously replicating sequence, an artificial chromosome, such as the bacterial artificial chromosome BAC, phage or other nucleotide sequence, in which at least two nucleotide sequences, at least one of which is a nucleic acid molecule of the present invention, have been joined or recombined. A vector may be linear or circular. A vector may be composed of a single or double stranded DNA or RNA. A vector may be derived from any source. Such a vector is preferably capable of introducing the regulatory element, for instance a promoter fragment, and the nucleic acid molecule of the present invention, preferably a DNA sequence for inducing apomixis, in a plant, in sense or antisense orientation along with appropriate 3' untranslated sequence into a cell, in particular a plant cell.

The term "expression" refers to the transcription and/or translation of an endogenous gene or a transgene in plants.

"Marker genes" usually encode a selectable or screenable trait. Thus, expression of a "selectable marker gene" gives the cell a selective advantage which may be due to their ability to grow in the presence of a negative selective agent, such as an antibiotic or a herbicide compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell gives the cell both, a negative and a positive selective advantage. On the other hand a "screenable marker gene" does not confer a selective advantage to a transformed cell, but its expression makes the transformed cell phenotypically distinct from untransformed cells.

The term "expression in the vicinity of the embryo sac" refers to expression in carpel, integuments, ovule, ovule primordium, ovary wall, chalaza, nucellus, funicle or placenta. The term "integuments" refers to tissues which are derived therefrom, such as endothelium. The term "embryogenic" refers to the capability of cells to develop into an embryo under permissive conditions.

The term "plant" refers to any plant, but particularly seed plants.

The term "transgenic plant" or "transgenic plant cell" or "transgenic plant material" refers to a plant, plant cell or plant material which is characterised by the presence of a polynucleotide or polynucleotide variant of the present invention, which may—in case it is autologous to the plant—either be located at another place or in another orientation than usually found in the plant, plant cell or plant material or which is heterologous to the plant, plant cell or plant material. Preferably, the transgenic plant, plant cell or plant material expresses the polynucleotide or its variants such as to induce apomixis.

A transgenic plant, transgenic plant cell or transgenic plant material can be identified at the phenotypical level, for instance by observation of apomictic seed production, or at protein level, for instance by immunodetection or at the DNA or RNA level, for instance with polymerase chain reaction (PCR). Even in case the transgene in the transgenic plant, transgenic plant cell or transgenic plant material has a natural homologue therein with a very high similarity, PCR can be used to discriminate such a transgene by at least one nucleotide difference. In particular, SNP (single nucleotide polymorphism) existing between host alleles and transforming alleles can be used to detect transformed plants simply by PCR.

The term "plant cell" describes the structural and physiological unit of the plant, and comprises a protoplast and a cell wall. The plant cell may be in form of an isolated single cell, such as a stomatal guard cells or a cultured cell, or as a part of a higher organized unit such as, for example, a plant tissue, or a plant organ.

The term "plant material" includes plant parts, in particular plant cells, plant tissue, in particular plant propagation material, preferably leaves, stems, roots, emerged radicles, flowers or flower parts, petals, fruits, pollen, pollen tubes, anther filaments, ovules, embryo sacs, egg cells, ovaries, zygotes, embryos, zygotic embryos per se, somatic embryos, hypocotyl sections, apical meristems, vascular bundles, pericycles, seeds, roots, cuttings, cell or tissue cultures, or any other part or product of a plant.

Thus, the present invention also provides plant propagation material of the transgenic plants of the present invention. Said "plant propagation material" is understood to be any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants. Parts of plants, such as for example flowers, stems, fruits, leaves, roots originating in transgenic plants or their progeny previously transformed by means of the methods of the present invention and therefore consisting at least in part of transgenic cells, are also an object of the present invention. Especially preferred plant materials, in particular plant propagation materials, are apomictic seeds.

Particularly preferred plants are monocotyledonous or dicotyledonous plants. Particularly preferred are crop or agricultural plants, such as sunflower, peanut, corn, potato, sweet potato, bean, pea, chicory, lettuce, endive, cabbage, cauliflower, broccoli, turnip, radish, spinach, onion, garlic, eggplant, celery, carrot, squash, pumpkin, zucchini, cucumber, apple, pear, melon, strawberry, grape, raspberry, pineapple, soybean, *Cannabis, Humulus* (hop), tomato, sorghum, sugar cane, and non-fruit bearing trees such as poplar, rubber, *Paulownia*, pine, elm, *Lolium, Festuca, Dactylis*, alfalfa, safflower, tobacco, cassava, coffee, coconut, pineapple, citrus trees, cocoa, tea, banana, avocado, fig, guava, mango, olive, *papaya*, cashew, macadamia, almond, green beans, lima beans, peas, fir, hemlock, spruce, redwood, in particular maize, wheat, barley, sorghum, rye, oats, turf and forage grasses, millet, rice and sugar cane. Especially preferred are maize, wheat, sorghum, rye, oats, turf grasses and rice.

Particularly preferred are also ornamental plants such as ornamental flowers and ornamental crops, for instance *Begonia, Carnation, Chrysanthemum, Dahlia, Gardenia, Asparagus*, Geranium, Daisy, *Gladiolus, Petunia, Gypsophila, Lilium*, Hyacinth, Orchid, Rose, Tulip, Aphelandra, *Aspidistra, Aralia, Clivia, Coleus, Cordyline*, Cyclamen, Dracaena, Dieffnbachia, *Ficus*, Philodendron, Poinsettia, Fern, Ivy, Hydrangea, *Limonium*, Monstera, Palm, Datepalm, Potho, Singonio, Violet, Daffodil, Lavender, Lily, *Narcissus, Crocus, Iris*, Peonies, Zephyranthes, Anthurium, *Gloxinia, Azalea, Ageratum, Bamboo, Camellia, Dianthus, Impatien, Lobelia, Pelargonium*, Lilac, Lily of the Valley, Stephanotis, Hydrangea, Sunflower, Gerber daisy, Oxalis, Marigold and Hibiscus.

Among the dicotyledonous plants *Arabidopsis*, Boechera, soybean, cotton, sugar beet, oilseed rape, tobacco, pepper, melon, lettuce, *Brassica* vegetables, in particular *Brassica napus*, sugar beet, oilseed rape and sunflower are more preferred herein.

"Transformation", "transforming" and "transferring" refers to methods to transfer nucleic acid molecules, in particular DNA, into cells including, but not limited to, biolistic approaches such as particle bombardment, microinjection, permeabilising the cell membrane with various physical, for instance electroporation, or chemical treatments, for instance polyethylene glycol or PEG, treatments; the fusion of protoplasts or *Agrobacterium tumefaciens* or *rhizogenes* mediated trans-formation. For the injection and electroporation of DNA in plant cells there are no specific requirements for the plasmids used. Plasmids such as pUC derivatives can be used. If whole plants are to be regenerated from such transformed cells, the use of a selectable marker is preferred. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA have to be linked as flanking region to the genes to be introduced. Preferably, the transferred nucleic acid molecules are stably integrated in the genome or plastome of the recipient plant.

The expression "progeny" or "offspring" refers to both, "asexually" and "sexually" generated progeny of transgenic plants. This definition is also meant to include all mutants and variants obtainable by means of known processes, such as for example cell fusion or mutant selection and which still exhibit the characteristic properties of the initial transformed plant of the present invention, together with all crossing and fusion products of the transformed plant material. This also includes progeny plants that result from a backcrossing, as long as the said progeny plants still contain the polynucleotide and/or polypeptide according to the present invention.

The isolated nucleic acid molecule of the present invention is preferably a DNA, preferably a DNA from a plant, preferably from Brassicaceae, in particular Boechera, in particular Boechera holboellii, Boechera divaricarpa or Boechera stricta, in a particular genomic or cDNA sequence molecule. It may, however, also be a RNA, in particular mRNA.

The present invention also provides in a preferred embodiment a vector comprising the nucleic acid sequence according to the present invention. Both, the specific polynucleotide or the polynucleotide variant of the present invention can be contained in the vector in sense or antisense orientation to a regulatory element.

In a preferred embodiment the vector comprises the nucleic acid sequence of the present invention, in particular the specific polynucleotide or its variant coding the apomixis-inducing protein of the present invention, operably linked to at least one regulatory element, for instance a promoter, enhancer and/or polyadenylation signal.

In a preferred embodiment, said promoter is an inducible or constitutive promoter. The promoter may be a regulatable promoter. The promoter may also be an ovule-specific promoter, which is a promoter allowing the expression of an operably linked coding sequence in the plant ovule of a plant, but not in other plant tissues. In a preferred embodiment, the promoter is the Ubiquitin-, ocs-, mas-, actin-, ADH-, NOS- or CaMV355-promoter. In order to obtain expression of the present nucleic acid molecule in a regenerated plant, in particular the ovule thereof, in a tissue specific manner the polynucleotide or polynucleotide variant of the present invention is preferably under expression control a regulatory element, for instance of an inducible or developmentally regulated promoter.

In a furthermore preferred embodiment of the present invention the polynucleotide, in particular the specific polynucleotide or polynucleotide variant, coding for a protein with exonuclease activity is operably linked to a polynucleotide or polynucleotide variant of the present invention which is able to act as a regulatory element, in particular a promoter.

In a furthermore preferred embodiment of the present invention the vector comprises a polynucleotide, in particular the specific polynucleotide or polynucleotide variant of the present invention capable of acting as a regulatory element operably linked to a protein coding nucleic acid sequence desired to be expressed in a plant, in particular a plant ovule.

The present invention also provides in a preferred embodiment a host cell containing the vector of the present invention. Preferably, the host cell is not a human cell, preferably not a human stem cell, germinal cell or embryogenic cell.

The present invention also provides a transgenic plant, plant cell, plant material, in particular plant seed comprising at least one nucleic acid molecule according to the present invention or the vector of the present invention. The present invention also provides in a preferred embodiment a cell culture, preferably a plant cell culture comprising a cell according to the present invention.

In a particularly preferred embodiment the present invention provides a transgenic plant, plant cell, plant material, in particular plant seed, wherein the polynucleotide, the polypeptide or the variant thereof exhibit its biological function. In a particular embodiment of the present invention a plant or plant seed is provided which comprises the polynucleotide, polypeptide or variants thereof of the present invention and which show due to the presence of said polynucleotide or polypeptide or variant thereof apomixis.

The present invention also provides proteins, in particular polypeptides or polypeptides variants, that means functional equivalents to polypeptides of the present invention, that means polypeptides capable of inducing apomixis in a plant or in vitro, which are coded by the nucleic acid molecules of the present invention.

Thus, in a particularly preferred embodiment of the present invention the present proteins capable of inducing apomixis in a plant are apollo proteins, that means comprise an amino acid sequence as characterised by any one of SEQ ID No. 1 to 21, preferably 4, 5, 6, 7, 8, 9, 10, 11, 12, 13, 14, 15, 16, 17, 18, 19, 20 or 21, preferably 4, 5, 6, 7, 8, 9, 13, 14, 15, 19, 20 or 21, preferably 4, 5, 6, 7, 8 or 9. In a particularly preferred embodiment the present proteins capable of inducing apomixis in a plant have, preferably comprise, an amino acid sequence as set forth in any one of SEQ ID No. 10, 11, 12, 13, 14, 15, 16, 17, 18, 19, 20 or 21, preferably 13, 14, 15, 19, 20 or 21. Preferred are also proteins comprising the amino acid sequence as given in SEQ ID No. 1, 2 or 3.

The present invention also provides a method for inducing apomixis in a plant, wherein the expression of a nucleotide sequence encoding a protein capable of inducing apomixis in the plant, in particular the apollo protein, in particular in the ovule of the plant, is induced in said ovule. Most preferably, said protein has, preferably comprises, the amino acid sequence as specified in any one of SEQ ID No. 1 to 21, preferably 4, 5, 6, 7, 8, 9, 10, 11, 12, 13, 14, 15, 16, 17, 18, 19, 20 or 21, preferably 4 to 9, 13 to 15 or 19 to 21, preferably 10, 11, 12, 13, 14, 15, 16, 17, 18, 19, 20 or 21, most preferably 4, 5, 6, 7, 8 or 9, in particular 1, 2 or 3.

Thus, the present invention foresees a method according to which in a plant ovule the expression of the polynucleotides of the present invention, in particular the presence of the protein of the present invention capable of inducing apomixis, is provided in order to induce apomixis and whereby said polynucleotides either have been transformed in said plant in an expressible status, that means in a form capable of inducing apomixis, or are endogenously present and are activated, in particular their regulatory elements, by mutation, for instance by radiation, chemical agents or exogenously transformed polynucleotides. Thus, the present invention provides the teaching to induce the expression of polynucleotides of the present invention in the plant ovule so as to allow the induction of apomixis in the plant ovule.

In a particularly preferred embodiment of the present invention the present invention therefore foresees to induce expression of polynucleotides encoding polypeptides capable of inducing apomixis in a plant ovule by transforming a plant with polynucleotides of the present invention being under appropriate regulatory control, in particular under control of a promoter, which polynucleotide codes a protein capable of inducing apomixis in a plant, so as to allow and induce expression of the transformed polynucleotide in the plant ovule thereby inducing apomixis in the plant.

The present invention also provides a method for inducing apomixis in a plant by transforming a plant cell with the isolated nucleic acid molecule according to the present invention or the vector according to the present invention and regenerating the transformed plant cell into a transformed plant that contains, in particular contains and expresses, the at least one nucleic acid sequence of the present invention so as to induce apomixis in the plant.

The present invention also provides a method for inducing apomixis in a plant, wherein the regulation of endogenously present polynucleotides having the same DNA sequence as the presently isolated polynucleotides of the present invention are induced to be expressed in a plant ovule. Thus, in this preferred embodiment, the present invention teaches to induce the expression of endogenously present polynucleotides encoding proteins capable of inducing apomixis in a plant ovule, in particular by structurally altering the regulatory elements of said endogenously present polynucleotide sequence, in particular its promoter, so as to allow expression therefrom.

The present invention achieves said structurally altering of the regulatory elements of said endogenously present polynucleotide sequence coding a protein capable of inducing apomixis in the plant by transforming the plant with either any DNA sequence capable of structurally modifying the endogenously present regulatory elements of said polynucleotide capable of expressing a protein capable of inducing apomixis in a plant or by transforming the specific regulatory elements of the present invention so as to induce apomixis in the plant.

Thus, the present invention also relates to a method for the production of an apomictic plant by transforming a plant cell with the isolated nucleic acid molecule or the vector of the present invention and regenerating the transformed plant cell into a transformed plant that contains, in particular contains and expresses, the at least one nucleic acid sequence of the present invention so as to induce apomixis in the plant.

The present invention also provides a method of inducing vegetative reproduction via seeds in a plant generation comprising transforming a plant cell with the isolated nucleic acid molecule according to the present invention or the vector according to the present invention and regenerating the transformed plant cell into a transformed plant which contains, in particular contains and expresses, the at least one nucleic acid sequence so as to induce apomixis in the plant.

The present invention also provides a method for inducing apomixis, in particular for inducing vegetative reproduction of a new or further plant generation, comprising transgenically expressing a nucleic acid molecule, in particular nucleic acid sequence of the present invention, in particular in a plant or plant cell.

In a particularly preferred embodiment of the present invention the nucleic acid sequence of the present invention, in particular the transgenic polynucleotide or polynucleotide variant of the present invention, is transgenically expressed in the ovule, in particular vicinity of the embryo sac.

The present invention also provides in a preferred embodiment a method for isolating an apomixis-inducing nucleic acid molecule from a plant wherein the isolated nucleic acid molecule of the present invention is used to screen and isolate nucleic acid molecules derived from the plant. Thus, the present invention provides the teaching on the identity of a nucleic acid molecule for use in inducing apomixis in plants which allows the skilled person to design on the basis of said nucleic acid molecules one or more primer to identify similar sequence by PCR in a genome or a part thereof.

The present invention also relates in a preferred embodiment to a method for identifying, in particular screening, for an effector of apomixis, in particular an apomictic phenotype, wherein a transgenic plant, plant cell or plant material according to the present invention is used, in particular cultivated, preferably cultivated and analysed.

Apomixis effectors can be detected by different technologies, preferably depending upon the initial information available, for instance by protein or immunodetection.

Thus, the present invention also provides means and methods to identify and obtain further substances, in particular proteins or nucleic acid sequences, which are involved in the development of an apomictic phenotype, in particular which are associated, in particular relate to the development of an apomictic phenotype.

Whilst the present invention is particularly described by way of the production of apomictic seed by heterologous expression of a polynucleotide of the present invention, it will be recognized that variants of the present polynucleotides, the products of which have a similar structure and function may likewise be expressed with similar results. Moreover, although the example illustrates apomictic seed production in Boechera and *Arabidopsis*, the invention is, of course, not limited to the expression of apomictic seed-inducing genes solely in these plants. Moreover, the present disclosure also includes the possibility of expressing the inventive polynucleotides in transformed plant material in a constitutive, tissue non-specific manner, for example under transcriptional control of a Ubiquitin-, ocs-, mas-, actin-, ADH-, CaMV35S or NOS promoter.

The following embodiments represent particularly preferred variants of the present invention.

EMBODIMENT 1

A method for inducing apomixis in a plant, wherein a nucleotide sequence encoding a protein capable of inducing apomixis in a plant is induced to be expressed in the ovule of said plant and wherein said nucleotide sequence comprises a polynucleotide, which codes for a protein with exonuclease activity, which polynucleotide is selected from the group consisting of xa) the polynucleotide defined in any one of SEQ ID No. 22 to 54 or a fully complementary strand thereof,
xb) a polynucleotide encoding a polypeptide with the amino acid sequence defined in any one of SEQ ID No. 1 to 21 or a fully complementary strand thereof, and
xc) a polynucleotide variant having a degree of sequence identity of more than 30%, 40%, 50% or preferably 70% to the nucleic acid sequence defined in xa) or xb), or a fully complementary strand thereof.

EMBODIMENT 2

The method of embodiment 1, wherein the polynucleotide is selected from the group consisting of xa1) the polynucleotide defined in any one of SEQ ID No. 26, 31, 36, 39, 42, 45, 48, 51, 54 or a fully complementary strand thereof,
xb1) a polynucleotide encoding a polypeptide with the amino acid sequence defined in any one of SEQ ID No. 1, 2, 3, 10, 11, 12, 16, 17, 18 or a fully complementary strand thereof, and
xc1) a polynucleotide variant having a degree of sequence identity of more than 30%, 40%, 50% or, preferably 70% to the nucleic acid sequence defined in xa1) or xb1), or a fully complementary strand thereof.

EMBODIMENT 3

The method of embodiment 1, wherein the polynucleotide is selected from the group consisting of xa2) the polynucleotide defined in any one of SEQ ID No. 22, 23, 27, 28, 32, 33 or a fully complementary strand thereof,
xb2) a polynucleotide encoding a polypeptide with the amino acid sequence defined in any one of SEQ ID No. 4, 5, 6 or a fully complementary strand thereof, and
xc2) a polynucleotide variant having a degree of sequence identity of more than 70% to the nucleic acid sequence defined in xa2) or xb2), or a fully complementary strand thereof.

EMBODIMENT 4

An isolated nucleic acid molecule for use in inducing apomixis in a plant, which comprises a polynucleotide which polynucleotide is able to act as a regulatory element and is selected from the group consisting of a3) the polynucleotide defined in any one of SEQ ID No. 55 to 62 or 65 or a fully complementary strand thereof and
b3) a polynucleotide variant having a degree of sequence identity of more than 70% to the nucleic acid sequence defined in a3), or a fully complementary strand thereof.

EMBODIMENT 5

An isolated nucleic acid molecule for use in inducing apomixis in a plant, which comprises a polynucleotide coding for a protein with exonuclease activity, which polynucleotide is selected from the group consisting of xa4) the polynucleotide defined in any one of SEQ ID No. 26, 31, 36, 39, 42, 45, 48, 51, 54 or a fully complementary strand thereof,
xb4) a polynucleotide encoding a polypeptide with the amino acid sequence defined in any one of SEQ ID No. 1, 2, 3, 10, 11, 12, 16, 17, 18 or a fully complementary strand thereof, and
xc4) a polynucleotide variant having a degree of sequence identity of more than 98% to the nucleic acid sequence defined in xa4) or xb4), or a fully complementary strand thereof.

EMBODIMENT 6

An isolated nucleic acid molecule for use in inducing apomixis in a plant, which comprises a polynucleotide coding for a protein with exonuclease activity, which polynucleotide is selected from the group consisting of xa5) the polynucleotide defined in any one of SEQ ID No. 22, 23, 24, 25, 27, 28, 29, 30, 32, 33, 34, 35, 37, 38, 40, 41, 43, 44, 46, 47, 49, 50, 52, 53 or a fully complementary strand thereof, xb5) a polynucleotide encoding a polypeptide with the amino acid sequence defined in any one of SEQ ID No. 4, 5, 6, 7, 8, 9, 13, 14, 15, 19, 20, 21 or a fully complementary strand thereof, and xc5) a polynucleotide variant having a degree of sequence identity of more than 90% to the nucleic acid sequence defined in xa5) or xb5), or a fully complementary strand thereof.

EMBODIMENT 7

A vector comprising the nucleic acid molecule of any one of embodiments 4 to 6.

EMBODIMENT 8

A host cell containing the vector of embodiment 7.

EMBODIMENT 9

A protein encoded by a nucleotide acid sequence according to any one of embodiments 5 or 6.

EMBODIMENT 10

A transgenic plant, plant cell or plant material comprising at least one transgenic nucleic acid molecule of any one of embodiments 4 to 6 or the vector of embodiment 7.

EMBODIMENT 11

A cell culture, preferably a plant cell culture comprising a cell according to embodiment 8.

EMBODIMENT 12

The method for inducing apomixis in a plant according to any one of embodiments 1 to 3, wherein the expression is induced by transforming a plant cell with an isolated nucleic acid molecule comprising a polynucleotide which codes for a protein with exonuclease activity as defined in any one of embodiments 1 to 3, 5 or 6, with the isolated nucleic acid molecule of embodiment 4 or with the vector according to embodiment 7 and regenerating the transformed plant cell into a transformed plant that contains the transformed at least one nucleic acid sequence so as to induce apomixis in the plant.

EMBODIMENT 13

A method for the production of an apomictic plant, wherein a plant cell is transformed with a nucleic acid molecule capable of inducing the expression of a nucleotide sequence encoding a protein capable of inducing apomixis in a plant and regenerating the transformed plant cell into a transformed plant that contains the transformed nucleic acid molecule so as to induce apomixis in the plant, wherein the nucleotide sequence encoding the protein capable of inducing apomixis in the plant is a polynucleotide, which codes for a protein with exonuclease activity, which polynucleotide is selected from the group consisting of xa) the polynucleotide defined in any one of SEQ ID No. 22 to 54 or a fully complementary strand thereof, xb) a polynucleotide encoding a polypeptide with the amino acid sequence defined in any one of SEQ ID No. 1 to 21 or a fully complementary strand thereof, and xc) a polynucleotide variant having a degree of sequence identity of more than 70% to the nucleic acid sequence defined in xa) or xb), or a fully complementary strand thereof.

EMBODIMENT 14

The method for the production of an apomictic plant by transforming according to embodiment 13, wherein the plant cell is transformed with an isolated nucleic acid molecule comprising a polynucleotide, which codes for a protein with exonuclease activity, which polynucleotide is selected from the group consisting of xa) the polynucleotide defined in any one of SEQ ID No. 22 to 54 or a fully complementary strand thereof, xb) a polynucleotide encoding a polypeptide with the amino acid sequence defined in any one of SEQ ID No. 1 to 21 or a fully complementary strand thereof, and xc) a polynucleotide variant having a degree of sequence identity of more than 70% to the nucleic acid sequence defined in xa) or xb), or a fully complementary strand thereof or with the isolated nucleic acid molecule of embodiment 4 or with the vector of embodiment 7 and the transformed plant cell is regenerated into a transformed plant that contains the at least one nucleic acid sequence so as to induce apomixis in the plant.

EMBODIMENT 15

A method for isolating an apomixis inducing nucleic acid molecule from a plant, wherein an isolated nucleic acid molecule comprising a polynucleotide, which codes for a protein with exonuclease activity, which polynucleotide is selected from the group consisting of xa) the polynucleotide defined in any one of SEQ ID No. 22 to 54 or a fully complementary strand thereof, xb) a polynucleotide encoding a polypeptide with the amino acid sequence defined in any one of SEQ ID No. 1 to 21 or a fully complementary strand thereof, and xc) a polynucleotide variant having a degree of sequence identity of more than 70% to the nucleic acid sequence defined in xa) or xb), or a fully complementary strand thereof or the isolated nucleic acid molecule of embodiment 4 or the vector of embodiment 7 is used to screen and isolate nucleic acid sequences derived from the plant.

EMBODIMENT 16

A transgenic plant, plant cell or plant material comprising a cell according to any one of embodiment 8 or produced according to a method according to any one of embodiments 13 or 14 or progeny thereof.

EMBODIMENT 17

The transgenic plant, plant cell or plant material according to embodiment 16 transgenically expressing the nucleotide acid sequence of any one of embodiments 5 or 6.

EMBODIMENT 18

A method for identifying an effector for apomixis in a plant, wherein the transgenic plant, plant cell or plant material according to any one of embodiments 16 or 17 is cultivated.

Further preferred embodiments of the present invention are the subject matter of the subclaims.

The invention will now be illustrated by way of example.

EXAMPLE 1: SCREENING AND ISOLATION OF APOMIXIS-INDUCING GENE (APOLLO GENE)

1.a) Plant Material and Seed Screen Analysis

Plants were grown from seedlings onwards in a phytotron under controlled environmental conditions. The flow cytometric seed screen was used to analyse reproductive variability in 18 Boechera accessions (Table IV).

Table IV. Boechera accessions used in Microarrays and RT-PCR analyses.

TABLE IV

Boechera accessions used in Microarrays and RT-PCR analyses.

| Accession | Apomeiosis frequency | Collection locality |
|---|---|---|
| B08-1 | 1 | Birch Creek, Montana |
| B08-11 | 1 | Sliderock, Ranch Creek, Granite, Montana |
| B08-33 | 1 | Mule Ranch, Montana |
| B08-111 | 1 | Morgan Switch Back, Idaho |
| B08-81 | 1 | Vipond Park, Beaverhead, Montana |
| B08-168 | 1 | Vipond Park, Beaverhead, Montana |
| B08-43 | 1 | Mule Ranch, Montana |
| B08-66 | 1 | Highwood Mtns, Montana |
| B08-104 | 1 | Lost Trail Meadow |
| B08-215 | 1 | Blue Lakes road, California |
| B08-369 | 0 | Twin Saddle, Idaho |
| B08-376 | 0 | Sagebrush Meadow, Montana |
| B08-380 | 0 | Buffalo Pass, Colorado |
| B08-355 | 0 | Gold Creek, Colorado |
| B08-329 | 0 | Big Hole Pass, Montana |
| B08-385 | 0 | Parker Meadow, Idaho |
| B08-344 | 0 | Bandy Ranch, Montana |
| B08-390 | 0 | Panther Creek |

Single seeds were ground individually with three 2.3 mm stainless steel beads in each well of 96-well plate (PP-Master-block 128.0/85 MM, 1.0 ml 96 well plate by Greiner bio-one, on the world wide web at "gbo.com") containing 50 µl extraction-nuclei isolation buffer (see below) using a Geno-Grinder 2000 (SPEX CertiPrep) at rate of 150 strokes/minute for 90 seconds.

A two-step procedure consisting of an isolation and staining buffer was used: (a) isolation buffer I—0.1M Citric acid monohydrate and 0.5% v/v Tween 20 dissolved in $H_2O$ and adjusted to pH 2.5); and (b) staining buffer II—0.4M $Na_2HPO_4.12H_2O$ dissolved in $H_2O$ plus 4 µg/ml 4',6-Diamidinophenyl-indole (DAPI) and adjusted to pH 8.5. 50 µl of isolation buffer I was added to each seed per well in a 96-well plate before grinding, and a further 160 µl buffer I was added after grinding to recover enough volume through filtration (using Partec 30 µm mesh-width nylon filters). 100 µl of staining buffer II was then added to 50 µl of the resultant suspension (isolated nuclei), and incubated on ice for 10 minutes before flow cytometric analysis. To avoid sample degradation over the 2-hour period required for the analysis of 96 samples, the sample plate was sealed with aluminum sealing tape.

All sample plates were analysed on a 4° C. cooled Robby-Well autosampler hooked up to a Partec PAII flow Cytometer (Partec GmbH, Münster, Germany). Two single seeds from SAD 12, a known sexual self-fertile Boechera were always included as an external reference at well positions 1 and 96 in order to normalize other peaks and correct peak shifts over the analysis period. SAD 12 seeds were composed exclusively of 2C embryo to 3C endosperm ratio, which reflected an embryo composition of C (C denotes monoploid DNA content) maternal (Cm) genomes+C paternal (Cp)=2C genomes, and an endosperm composition of 2Cm+Cp=3C.

Based upon the present high-throughput flow-cytometric seed screen data, all apomictic accessions were shown to be characterized by 100% apomictic seed production.

1.b) Ovule Micro-Dissection

Ovules at megasporogenesis between stages 2-II to 2-IV were selected where megaspore mother cell is differentiated, inner and outer integument initiated in order to examine changes in gene expression associated with meiosis and apomeiosis. The gynoecia of sexual and apomictic Boechera were dissected out from nonpollinated flowers at the stage of megasporogenesis in 0.55 M sterile mannitol solution, at a standardized time (between 8 and 9 a.m.) over multiple days. Microdissections were done in a sterile laminar air flow cabinet using a stereoscopic Microscope (1000 Stemi, Carl Zeiss, Jena, Germany) under 2× magnification. The gynoecium was held with forceps while a sterile scalpel was used to cut longitudinally such that the halves of the silique along with the ovules were immediately exposed to the mannitol. Individual live ovules were subsequently collected under an inverted Microscope (Axiovert 200M, Carl Zeiss) in sterile conditions, using sterile glass needles (self-made using a Narishige PC-10 puller, and bent to an angle of about 100°) to isolate the ovules from placental tissue. Using a glass capillary (with an opening of 150 µm interior diameter) interfaced to an Eppendorf Cell Tram Vario, the ovules were collected in sterile Eppendorf tubes containing 100 µl of RNA stabilizing buffer (RNAlater, Sigma). Between 20 and 40 ovules per accession were collected in this way, frozen directly in liquid nitrogen and stored at −80° C.

1.c) Ovule RNA Isolation

Total RNA extractions were carried out using PicoPure RNA isolation kit (Arcturus Bioscience, CA). RNA integrity and quantity was verified on an Agilent 2100 Bioanalyzer using the RNA Pico chips (Agilent Technologies, Palo Alto, Calif.).

1.d) Microarray 1.d.i) Microarray Design

The 454 (FLX) technology was used to sequence the complete transcriptomes of 3 sexual and 3 apomictic Boechera accessions, as a first step in the design of high-density Boechera-specific microarrays for use in comparisons of gene expression and copy number variation. The goal of transcriptome sequencing was thus to identify all genes which can be expressed during flower development, followed by the spotting of all identified genes onto an (Agilent) microarray.

This was accomplished by pooling flowers at multiple developmental stages separately for sexual and apomictic plants, followed by a cDNA normalization procedure in order to balance out transcript levels to increase the chance that all observable mRNA species are sequenced. Furthermore, a 3'-UTR (untranslated region) anchored 454 procedure was employed such that mRNA sequences were biased towards their 3'-UTRs, regions which demonstrate relatively high (but not random) levels of variability, to enable the identification of allelic variation.

The 454 sequences were assembled using the CLC Genomics workbench using standard assembly parameters for long-read high-throughput sequences, after trimming of all reads using internal sequence quality scores. In doing so, 36 289 contig sequences and 154 468 non-assembled singleton sequences were obtained. This data was provided to ImaGenes (GmbH, Germany) for microarray development using their Pre-selection strategy (PSS) service.

The PSS service worked as follows: 14 different oligonucleotides (each 60 bp in length) per contig and 8 oligonucleotides per singleton, including the "antisense" sequence of each oligo, were bioinformatically designed and spotted onto two 1 million-spot test arrays. These test-arrays were probed using (1) a "complex cRNA mixture" (obtained by pooling tissues and harvesting all RNA from them), and (2) genomic DNA extracted from leaf tissue pooled from a sexual and an apomictic individual. Based upon the separate hybridization results from the cRNA and genomic DNA samples, and after all quality tests, a final 2×105 000 spot array was designed. This array should contain multiple oligonucleotides (i.e. technical replicates) of every gene expressed during Boechera flower development.

1.d.ii) Hybridization cRNA was prepared and labelled using the Quick-Amp One-Color Labeling Kit (Agilent Technologies, CA) and hybridized to the Agilent custom Boechera arrays (8 and 10 biological replicates were hybridized for sexual and apomictic genotypes respectively).

1.d.iii) Statistical Analysis

Analyses were performed using GeneSpring GX Software (version 10) and candidate probes significantly differentially expressed (p 0.05) between apomictic and sexual plants were selected based on the following parameters: (a) percentile shift 75 normalization, median as baseline, reproductive mode (apomictic or sexual) as interpretation (1st level), T-test unpaired as statistical analysis and Bonferroni FWER multiple test corrections. Using the highest level of significance cutoff led to the identification of 4 different spots on the microarray ($p<0.01$ for the first three and $p<0.05$ for the fourth). Importantly, when the oligonucleotide sequences of these 4 spots were BLASTed to a 454 cDNA sequence database, all 4 blasted to the same Boechera transcript. Thus, not only has the present experiment been corrected for biological noise, furthermore a single differentially-expressed transcript between the microdissected ovules of all sexual and apomictic genotypes, with 4 technical replicates for the specific gene on the microarray was detected. This gene is expressed to a similar fashion when comparing both diploid and triploid apomictic ovules to those of sexuals, and hence its expression behavior is apparently not influenced by ploidy. Finally, a search for homologues to this Boechera transcript demonstrated that it is involved with the cell cycle in other species, thus supporting evidence regarding deregulation of the sexual pathway as a means to produce apomixis.

EXAMPLE 2: CHARACTERISATION OF APOMIXIS-INDUCING GENE 2.a) Candidate Gene Characterization
2.a.i) Genome Level
2.a.i.1) Cloning The full-length transcript from all 18 accessions was cloned and sequenced (TOPO-TA Cloning kit, Invitrogen) using proofreading polymerase (Accuprime). The transcript is highly polymorphic, and is characterized by comparable levels of single nucleotide polymorphisms between sexual and apomicts. Nevertheless, a single "apomixis polymorphism" is found in all 10 apomictic accessions, but not in any sexual accession. SEQ ID No. 46 to 54 show the genomic and the coding sequence of three sexual alleles, namely S011a, S355a and S390a. SEQ ID No. 37 to 45 show the genomic and the coding sequence of three apomictic alleles, namely A011a, A043a and A081a. Considering that the geographic collection points of all accessions range from California to the American mid-west (i.e. 1000's of kilometers), the sharing of this polymorphism in all apomicts is highly significant. Finally, the SNP polymorphism spectrum surrounding the "apomixis polymorphism" reflects that found in all other alleles in both sexual and apomictic accessions. Hence the "apomixis polymorphism" appears to have undergone recombination during the evolution of Boechera, but which is nonetheless shared by all apomicts, regardless of different genetic, ploidy or geographic backgrounds.

2.a.i.2) BAC

Pooled DNA of all tissues accessions was used as a template for hybridization probes generation. Two probes of different size (1.6 and 2.3 kb) were prepared by PCR amplification using two pairs of specific primers of the candidate gene genomic sequence. Both probes were labeled and used for hybridization on a apomictic Boechera BAC library. There were 8 positive hybridizations. The respective isolated BACs (PureLink Plasmid DNA Purification kit) were named 1, 2a, 2b, 3, 4, 5, 6 and 7. Selected BACs were retested using specific primers for the candidate gene. All BACs were confirmed except the BAC-3. The other seven BACs were fingerprinted by restriction enzyme digestion. BAC-1 and BAC-2a seemed to be redundant with the other BACs. The BACs: 2b, 4, 5, 6 and 7 were sequenced.

BAC sequences could be assembled together for the pairs 2b_4 and 5_7, whereas BAC-6 remained alone.

BAC sequences were characterized by comparison with other plant sequences.

2.a.ii) Transcriptome Level

RACE experiments (SMARTer RACE cDNA Amplification Kit) were performed.

The results revealed that mRNA corresponding to apomictic accessions has a truncated 5' extreme upstream the "apomixis polymorphism" whereas sexual accessions have ~200 bp of additional length.

Once 5' and 3' mRNA extremes were known, further PCRs over all tissues cDNA were performed for complete splicing profile characterization.

2.b) Validation
2.b.i) QRT-PCR

An allele-specific qRT-PCR analysis of the candidate gene on the microdissected live ovules (megaspore mother cell stage) from 6 sexual and 10 diploid apomictic Boechera accessions (3 technical replicates per accession) was completed. Using two different forward PCR primers which spanned the apomixis-specific polymorphism which was identified from the gene sequences, it was possible to measure transcript abundance for both the sexual and apomictic alleles separately.

cDNA was prepared using RevertAid H Minus reverse transcriptase.

For the real-time PCR reactions the SYBR® Green PCR Master Mix (Applied Biosystems, Foster City, Calif.) was used. QRT-PCR amplifications were carried out in a 7900HT Fast RT-PCR System machine (Applied Biosystems) with the following temperature profile for SYBRgreen assays:

initial denaturation at 90° C. for 10 min, followed by 40 cycles of 95° C. for 15 sec. and 60° C. for 1 min. For checking amplicon quality, a melting curve gradient was obtained from the product at the end of the amplification. The Ct, defined as the PCR cycle at which a statistically significant increase of reporter fluorescence is first detected, was used as a measure for the starting copy numbers of the target gene. The mean expression level and standard deviation for each set of three technical replicates for each cDNA was calculated. Relative quantitation and normalization of the amplified targets were performed by the comparative ΔΔCt method using a calibrator sample in reference to the expression levels of the house-keeping gene UBQ10.

The results are conclusive: the apomictic allele is exclusively expressed in the microdissected ovules of all apomictic accessions, while the sexual allele is never expressed in any, which means sexual or apomictic, ovule. Both alleles are expressed in other tissues, namely somatic tissue. Hence, it appears very reasonable to assume that the sexual allele is inactive/silenced during normal sexual ovule development, while the expression of the apomictic allele is correlated with apomeiotic ovule development.

EXAMPLE 3: CONSTRUCTION OF TRANSFORMATION VECTORS AND TRANSFORMATION OF ARABIDOPSIS THALIANA WITH APOMIXIS-INDUCING GENE

Plant Transformation

Transformations of *Arabidopsis thaliana* (sex) (hybrids F1) and Boechera (sex) with the gene of the present invention are able to show a change of their reproductive mode into apomictic seed production. For this, the complete genomic allele (including complete promoter) has been cloned in pNOS-ABM.

In addition, different constructs are used to characterize the role of the present regulatory elements, in particular the promoter of the present invention, in its expression. For this, both apo and sex promoters have been exactly connected to the ATG in front of gus in pGUS-ABM.

Complete BAC-4 is as well used for transformations.

The invention claimed is:

1. A vector comprising a recombinant polynucleotide that comprises promoter and 5' untranslated region of SEQ ID NO: 55 that is operably linked to a polynucleotide encoding a DEDD exonuclease protein, wherein the protein exhibits 3'-5' exonuclease activity and has at least 95% sequence identity over the full length of SEQ ID NO:14, wherein the promoter and the polynucleotide encoding the DEDD exonuclease protein are heterologous to one another and wherein the vector is capable of introducing the recombinant polynucleotide into a plant.

2. The vector of claim 1, wherein the protein comprises the exonuclease domain of SEQ ID NO: 2.

3. The vector of claim 2, wherein the exonuclease domain comprises the exonuclease domain of SEQ ID NO: 10, SEQ ID NO: 11, SEQ ID NO: 12, SEQ ID NO: 16, SEQ ID NO: 17, or SEQ ID NO: 18.

4. The vector of claim 1, wherein the protein contains the amino acid sequence DAADEAKTVR (SEQ ID NO: 63).

5. The vector of claim 4, wherein the protein further comprises a duplication of the amino acid sequence of SEQ ID NO: 63.

6. The vector of claim 1, wherein the protein has at least 97% or 99% sequence identity over the full length of SEQ ID NO:14.

7. The vector of claim 6, wherein the protein comprises the amino acid sequence of SEQ ID NO: 13, SEQ ID NO: 14, SEQ ID NO: 15, SEQ ID NO: 19, SEQ ID NO: 20, or SEQ ID NO: 21.

8. The vector of claim 1, wherein the promoter and 5' untranslated region comprises a polynucleotide having the nucleotide sequence of SEQ ID NO: 57.

9. A host cell comprising the vector of claim 1.

10. A transgenic plant cell comprising a recombinant polynucleotide that comprises promoter and 5' untranslated region of SEQ ID NO: 55 that is operably linked to a polynucleotide encoding a DEDD exonuclease protein, wherein the protein exhibits 3'-5' exonuclease activity and has at least 95% sequence identity over the full length of SEQ ID NO:14, and wherein the promoter and the polynucleotide encoding the DEDD exonuclease protein are heterologous to one another.

11. The transgenic plant cell of claim 10, wherein the plant cell is a soybean, cotton, sugar beet, tobacco, pepper, melon, lettuce, *Brassica napus*, citrus, pea, pine, tomato, *Cannabis*, or sunflower plant cell.

12. The transgenic plant cell of claim 10, wherein the plant cell is a maize, wheat, sorghum, rye, oat, turf grass, sugar cane, banana, or rice plant cell.

13. A method for the production of an apomictic plant comprising the steps of transforming a plant cell with the vector according to claim 1 and regenerating the transformed plant cell into a transformed plant that contains the recombinant polynucleotide that comprises promoter and 5' untranslated region of SEQ ID NO: 55 that is operably linked to a polynucleotide encoding a DEDD exonuclease protein, wherein the protein exhibits 3'-5' exonuclease activity and has at least 95% sequence identity over the full length of SEQ ID NO:14, and wherein the promoter and the polynucleotide encoding the DEDD exonuclease protein are heterologous to one another, so as to induce apomixis in the plant, thereby producing an apomictic plant.

14. The method of claim 13, wherein transforming is achieved by particle bombardment, microinjection, electroporation, chemical treatments, protoplast fusion, *Agrobacterium tumefaciens*, or *Agrobacterium rhizogenes* mediated transformation.

15. The method of claim 13, wherein the vector comprises a selectable marker or a screenable marker.

16. The method of claim 15, wherein the vector comprises a selectable marker and the transformed plant cell is selected for the presence of the selectable marker with a negative selective agent.

17. The method of claim 13, wherein the protein has at least 97% or 99% sequence identity over the full length of SEQ ID NO:14 and/or contains the amino acid sequence DAADEAKTVR (SEQ ID NO: 63).

18. The method of claim 13, wherein the protein comprises the exonuclease domain of SEQ ID NO: 2, SEQ ID NO: 10, SEQ ID NO: 11, SEQ ID NO: 12, SEQ ID NO: 16, SEQ ID NO: 17, or SEQ ID NO: 18.

19. The method of claim 13, wherein the plant cell is a soybean, cotton, sugar beet, tobacco, pepper, melon, lettuce, *Brassica napus*, citrus, pea, pine, tomato, *Cannabis*, or sunflower plant cell.

20. The method of claim 13, wherein the plant cell is a maize, wheat, sorghum, rye, oat, turf grass, sugar cane, banana, or rice plant cell.

\* \* \* \* \*